US012760340B2

(12) United States Patent
Awasthi et al.

(10) Patent No.: US 12,760,340 B2
(45) Date of Patent: Oct. 13, 2026

(54) METHODS AND COMPOSITIONS FOR THE PRODUCTION OF RHAMNOLIPID

(71) Applicant: THE REGENTS OF THE UNIVERSITY OF CALIFORNIA, Oakland, CA (US)

(72) Inventors: Deepika Awasthi, Emeryville, CA (US); Steven W. Singer, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 434 days.

(21) Appl. No.: 18/324,283

(22) Filed: May 26, 2023

(65) Prior Publication Data

US 2023/0399666 A1 Dec. 14, 2023

Related U.S. Application Data

(60) Provisional application No. 63/346,788, filed on May 27, 2022.

(51) Int. Cl.
*C12P 7/6409* (2022.01)
*C12N 9/10* (2006.01)
*C12N 9/88* (2006.01)

(52) U.S. Cl.
CPC .......... *C12P 7/6409* (2013.01); *C12N 9/1029* (2013.01); *C12N 9/1051* (2013.01); *C12N 9/88* (2013.01); *C12Y 203/01191* (2013.01); *C12Y 204/01* (2013.01); *C12Y 402/01055* (2013.01)

(58) Field of Classification Search
CPC ...... C12P 7/6409; C12P 19/44; C12N 9/1029; C12N 9/1051; C12N 9/88; C12Y 203/01191; C12Y 204/01; C12Y 402/01055
See application file for complete search history.

(56) References Cited

PUBLICATIONS

Awasthi et al., Adaptive evolution of Methylotuvimicrobium alcaliphilum to grow in the presence of rhamnolipids improves fatty acid and rhamnolipid production from CH4 . J. Indus. Microbiol. Biotechnol., 2022, vol. 49, kuac002; pp. 1-12. (Year: 2022).*
Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Hauser, G., et al.(1957). "Rhamnose and rhamnolipid biosynthesis by Pseudomonas aeruginosa." J. Biol. Chem 224: 91-105.
Jarvis, F. G., et al. (1949). "A glycolipid produced by Pseudomonas aeruginosa." J. Am. Chem. Soc., 71:4124-4126.
Burger, M. M., et al. (1963) "The enzymatic synthesis of a rhamnose-containing glycolipid by extracts of Pseudomonas aeruginosa." J. Biol. Chem, 238(8)2595-2602.
Lequette, Y. et al. (2005). "Timing and localization of rhamnolipid synthesis gene expression in Pseudomonas aeruginosa biofilms." J Bacteriol , 187:37-44.
Abdel-Mawgoud, A. M., et al. "A stereospecific pathway diverts beta-oxidation intermediates to the biosynthesis of rhamnolipid biosurfactants." Chem Biol, 21:156-164, (2014).
Geraud, M-F. et al. "The Rhamnose Pathway." Current Opinion in Structural Biology. 10:687-696 (2000).
Bazire, A. et al. "The Pseudomonas aeruginosa rhIG and rhIAB genes are inversely regulated and RhIG is not required for rhamnolipid synthesis." BMC Microbiology, 14:60-169 (2014).
Abdel-Mawgoud, A. M., et al. "Rhamnolipids: diversity of structures, microbial origins and roles." Appl Microbiol Biotechnol, 8:1323-1336, (2010).
Trummler, K., et al. "An integrated microbial/enzymatic process for production of rhamnolipids and I-(+)-rhamnose from rapeseed oil with *Pseudomonas* sp. DSM 2874." European Journal of Lipid Science and Technology, 105:563-571, (2003).
Wei, Y.-H., et al. "Rhamnolipid production by indigenous Pseudomonas aeruginosa J4 originating from petroChem. Wastewater," Biochemical Engineering Journal. 27:46 (2005).
Lovaglio, R. B., et al. "Effect of C/N ratio and physicoChem. conditions on the production of rhamnolipids by Pseudomonas aeruginosa LBI." Research Journal of Biotechnology, 19-24 (2010).
Irorere, V. U., et al. "Microbial rhamnolipid production: a critical re-evaluation of published data and suggested future publication criteria." Appl Microbiol Biotechnol, 101:3941-3951, (2017).

(Continued)

*Primary Examiner* — Ganapathirama Raghu
(74) *Attorney, Agent, or Firm* — Robin C. Chiang; LAWRENCE BERKELEY NATIONAL LABORATORY

(57) ABSTRACT

The present invention provides for a method for producing a rhamnolipid, the method comprising: (a) providing a genetically modified host cell comprising one or more of RhlYZAB capable of expression in the host cell in a growth or culture medium; (b) growing or culturing the host cell such that the one or more of RhlYZAB are expressed and a rhamnolipid is produced; and (c) optionally recovering the rhamnolipid from the host cell or from the growth or culture medium. In some embodiments, the host cell is a methanotroph.

9 Claims, 13 Drawing Sheets

Specification includes a Sequence Listing.

(56) References Cited

PUBLICATIONS

Dubeau, D., et al. "Burkholderia thailandensis harbors two identical rhl gene clusters responsible for the biosynthesis of rhamnolipids." BMC Microbiology, 9:263 (2009).

Costa S., et al. "Characterization of rhamnolipid production by Burkholderia glumae." Lett Appl Microbiol ,53:620-627 (2011).

Hörmann, B., et al. "Rhamnolipid production by Burkholderia plantarii DSM9509T." European Journal of Lipid Science and Technology, 112:674-680 (2010).

Beuker J, et a. "High titer heterologous rhamnolipid production." AMB Express, 6:124 (2016).

Wittgens A, et al. "Growth independent rhamnolipid production from glucose using the non-pathogenic Pseudomonas putida KT2440." Microb Cell Factories, 10:80 (2011).

Lotfabad T.B, et al. "Evaluation of a recycling bioreactor for biosurfactant production by Pseudomonas aeruginosa MR01 using soybean oil waste." J Chem Technol Biotechnol, 91:1368-1377 (2016).

Henard, C. A., et al. "Phosphoketolase overexpression increases biomass and lipid yield from methane in an obligate methanotrophic biocatalyst." Metab Eng, 41:152-158, (2017).

Henard, C. A., et al. "Muconic acid production from methane using rationally-engineered methanotrophic biocatalysts." Green Chemistry, 21:6731-6737, (2019).

Rozova, O. N., et al. "Characterization of recombinant pyrophosphate-dependent 6-phosphofructokinase from halotolerant methanotroph Methylomicrobium alcaliphilum 20Z." Res Microbiol, 161:861-868, (2010).

Akberdin, I. R. et al. "Methane utilization in Methylomicrobium alcaliphilum 20Z(R): a systems approach." Sci Rep, 8:2512, (2018).

Ojala, D. S., et al. "Genetic systems for moderatly halo (alkali) philic bacteria of the genus *Methylomicrobium*." Methods in Enzymology, 495(Chapter 7):99-118, (2011).

Kalyuzhnaya, M. G. et al. Highly efficient methane biocatalysis revealed in a methanotrophic bacterium. Nat Commun, 4:2785, (2013).

Kalyuzhnaya, M. G., et al. "Metabolic engineering in methanotrophic bacteria." Metab Eng, 29:142-152, (2015).

Bowman, J.P. ,et al. "Phospholipid fatty acid and lipopolysaccharide fatty acid signature lipids in methane-utilizing bacteria." FEMS Microbiology Ecology, 85:15-22 (1991).

Costello, A. M., et al. "Estimation of methanotroph abundance in lake." Environmental Microbiology, 4:443-450 (2002).

Parsons, J. B. & Rock, C. O. Bacterial lipids: metabolism and membrane homeostasis. Prog Lipid Res 52, 249-276, (2013).

Pfleger, R. M. L. a. B. F. Microbial production of fatty acid-derived fuels and chemicals. Current Opinion in Biotechnology 24, 1044-1053 (2013).

Lorra K. Fuhrman , A. W., Kenneth W. Nickerson and Tyrrell Conway Rapid accumulation of intracellular 2-keto-3-deoxy-6-phosphogluconate in an Entner-Doudoroff aldolase mutant results in bacteriostasis. FEMS Microbiology Letters 159, 261-266 (1998).

But, S. Y. et al. Sucrose metabolism in halotolerant methanotroph Methylomicrobium alcaliphilum 20Z. Arch Microbiol 197, 471-480, (2015).

Mustakhimov, II et al. Identification and characterization of EctR1, a new transcriptional regulator of the ectoine biosynthesis genes in the halotolerant methanotroph Methylomicrobium alcaliphilum 20Z. J Bacteriol 192, 410-417, doi:10.1128/JB.00553-09 (2010).

Demidenko, A., Akberdin, I. R., Allemann, M., Allen, E. E. & Kalyuzhnaya, M. G. Fatty Acid Biosynthesis Pathways in Methylomicrobium buryatense 5G(B1). Front Microbiol 7, 2167, (2016).

Yu, W. J., Lee, J. W., Nguyen, N. L., Rhee, S. K. & Park, S. J. The characteristics and comparative analysis of methanotrophs reveal genomic insights into *Methylomicrobium* sp. enriched from marine sediments. Syst Appl Microbiol 41, 415-426, (2018).

Nguyen, A. D. et al. Systematic metabolic engineering of Methylomicrobium alcaliphilum 20Z for 2,3-butanediol production from methane. Metab Eng 47, 323-333, (2018).

Henard, C. A., Akberdin, I. R., Kalyuzhnaya, M. G. & Guarnieri, M. T. Muconic acid production from methane using rationally-engineered methanotrophic biocatalysts. Green Chemistry 21, 6731-6737, (2019).

Fei, Q. et al. Bioconversion of natural gas to liquid fuel: opportunities and challenges. Biotechnol Adv 32, 596-614, (2014).

* cited by examiner

C
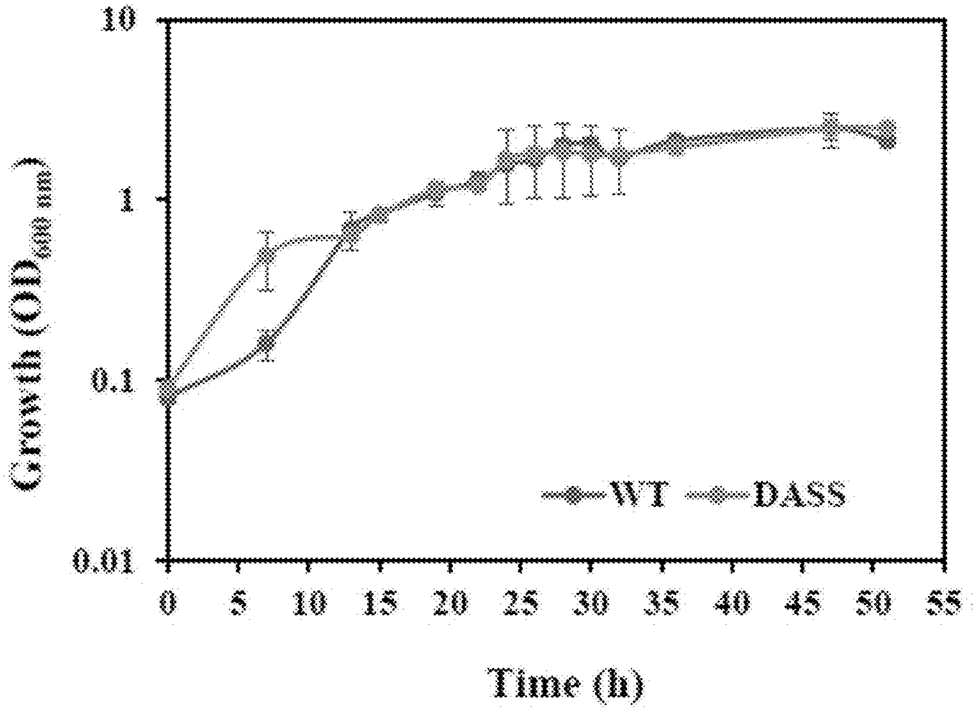
D
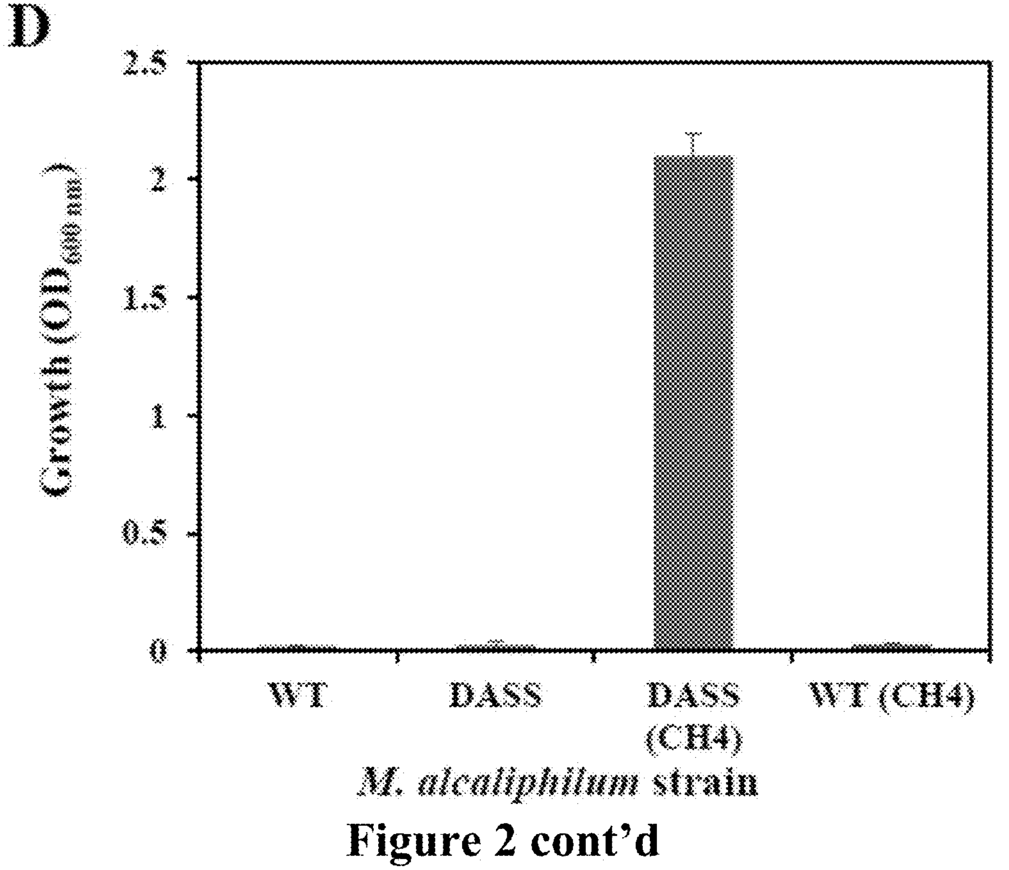
Figure 2 cont'd

| Fold Change | Gene name | Function |
|---|---|---|
| | accB | Fatty acid metabolism |
| | MEALZ_3011 | UC |
| | ssb | DNA Replication/repair |
| | rpsN | Ribosomal small subunit assembly |
| | rpoX | Translation regulation |
| | MEALZ_1142 | Exosortase system |
| | MEALZ_2580 | Stess Response: Csb domain containing |
| | MEALZ_3035 | Putative GGDEF/EALdomain-containing protein: second messanger |
| | MEALZ_0811 | UC |
| | secD | Protein export |
| | MEALZ_1779 | Heat shock protein |
| | mxaK | Methanol oxidation |
| | guaB | Purine metabolism: Inosine-5'-monophosphate dehydrogenase |
| | rpsF | 30S small ribosomal subunit |
| | MEALZ_1888 | UC |
| | csp | Cold shock proein: RNA helicase co-factor |
| | purA | Purine (AMP) biosynthesis: Adenylosuccinate synthetase |
| | MEALZ_3437 | UC |
| | MEALZ_1111 | UC (transmembrane) |
| | fimV | Pilus assembly protein |
| | fae2 | Carbohydrate metabolism: Formaldehyde-activating enzyme |
| | MEALZ_0810 | UC |
| | rpsJ | Translation: 30S ribosomal protein S10 |
| | accA | Fatty acid metabolism: Acetyl-coenzyme A carboxylase |
| | greA | Transcription elongation factor |
| | mxaI | Crabohydrate metabolism: Methanol dehydrogenase |
| | ppe | PPP: Ribulose-phosphate 3-epimerase |
| | frr | Efficient Translation: ribosome-recycling factor |
| | pma | Export across plasma membrane: Cation-transporting ATPase |
| | MEALZ_0967 | UC |
| | MEALZ_0447 | UC |
| | MEALZ_0170 | UC |
| | MEALZ_0519 | UC (transmembrane) |
| | rplL | Translation: 50S ribosomal protein L7/L12 |
| | MEALZ_2458 | UC (transmembrane) |
| | prlC | Protein quality control: oligopeptidase A |
| | atpG | ATP synthesis via transmembrane proton transport: ATP synthase |
| | nqrC | Na+ translocatng oxidoreductase-repiratory chain |
| | infC | Translation: Translation initiation factor IF-3 |
| | MEALZ_1128 | Heat shock chaperone network: DnaK-related protein |
| | corA | Cu and divalent cation transport |
| | oadA | Na+transport decarboxylase: oxaloacetate decarboxylase |
| | MEALZ_0106 | Cu detoxification/metal ion homeostatsis: multicopper oxidase type 2 |
| | orn | c-di-GMP homeostasis: oligoribonuclease |
| | MEALZ_0586 | OmpA-like domain-containing protein |
| | groS | groS (chaperonin) |
| | MEALZ_0243 | Putative membrane protein |
| | hupB | DNA-binding protein HU-beta (NS1) (HU-1) |

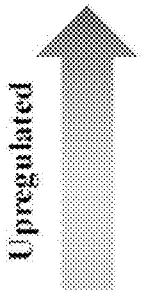

Figure 3

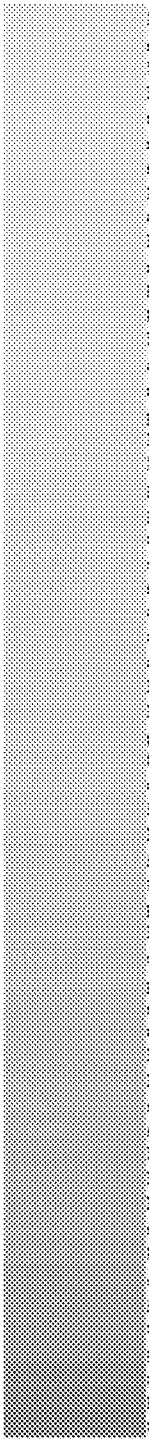

| | |
|---|---|
| MEALZ_3125 | Outer membrane chaperone Skp (OmpH) |
| ndk | Nucleoside diphosphate kinase |
| MEALZ_0090 | Uncharacterized protein |
| MEALZ_1822 | Cytochrome c family protein-ETS |
| tpiA | Glycolysis/Gluconeogenesis: triosephosphate isomerase |
| rpsC | Ribosomal small subunit assembly:30S ribosomal protein S3 |
| rpmC | Ribosomal large subunit assembly:50S ribosomal protein L29 |
| MEALZ_2869 | Putative chemotaxis protein CheY |
| erpA | Iron-sulfur cluster insertion protein |
| PPDK | Glycolysis: pyruvate, phosphate dikinase |
| manB | GDP-mannose biosynthetic process |
| hslU | Protein degradation: ATP-dependent protease |
| hisA | L-histidine biosynthesis |
| MEALZ_0971 | UC |
| cynS | Cyanate catabolic process |
| rplR | Translation: 50S ribosomal protein L18 |
| petA | Respiration: ubiquinol-cytochrome c reductase |
| MEALZ_2806 | TPR region domain-containing protein |
| MEALZ_1478 | UC |
| grxD | 2Fe-2S synthesis: Glutaredoxin |
| glnA | Glutamine biosynthesis:glutamine synthetase |
| ask | Branched chain amino acid biosynthesis: Aspartokinase |
| sgaA | Serine pathway assimilation:serine-glyoxylate transaminase activity |
| mxaR | Methanol metabolic process |
| acnB | TCA: aconitate hydratase B |
| acpP | Fatty acid biosynthetic process: acyl carrier protein |
| adk | Energy homeostasis ADP biosynthetic process: adenylate kinase |
| MEALZ_0589 | UC |
| MEALZ_1932 | Quorum sensing: Type VI secretion protein, EvpB/VC |
| pgk | Glycolysis/Gluconeogenesis: phosphoglycerate kinase |
| htpG | Molecular chaperone heat shock protein |
| clpB | Part of heat induced multi-chaperone system |
| ftsZ | Cell division initiation |
| MEALZ_0659 | Toxic anion resistance family protein |
| gap | Glycolysis/Gluconeogenesis: Glyceraldehyde-3-phosphate dehydrogenase |
| ffh | Protein export, signal recognition |
| purL | IMP biosynthetic process:phosphoribosylformylglycinamidine synthase |
| MEALZ_1491 | UC |
| clpX | Protein degradation: ATP-dependent protease |
| pdhD | Glycolysis/Gluconeogenesis: Dihydrolipoyl dehydrogenase |
| nusA | Transcription elongation factor |
| mtdB | Carbohydrate metabolism: NAD(P)-dependent methylene tetrahydromethanopterin dehydrogenase |
| MEALZ_3939 | Glycolysis/Gluconeogenesis: putative oxidoreductase 4Fe-FS cluster binding |
| MEALZ_2872 | Transmembrane signaling receptor: methyl-accepting chemotaxis |
| ilvI | Isoleucine biosynthetic process: acetolactate synthase |
| icd | TCA: Isocitrate dehydrogenase |
| MEALZ_0830 | Putative stringent starvation protein A |
| MEALZ_3005 | Putative nitrogen regulatory protein P-II |
| MEALZ_3400 | UC |
| infB | Translation initiation factor IF-2 |
| leuB | Branched amino acid synthesis: 3-isopropylmalate dehydrogenase |
| argG | Arginine biosynthesis: argininosuccinate synthase |
| glt | Glutamate biosynthesis: glutamate synthase (NADPH) |
| ftsH | Protein quality control |
| glgA2 | Glycogen biosynthesis: glycogen synthase |
| galU | Glycogen biosynthesis: UTP-glucose-1-phosphate uridylyltransferase |
| lon | ATP-dependent protease: Lon protease |
| ffsA | Formaldehyde catabolic process: Formylmethanofuran-tetrahydromethanopterin formyltransferase |

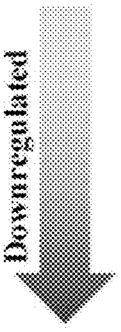

Figure 3 cont'd

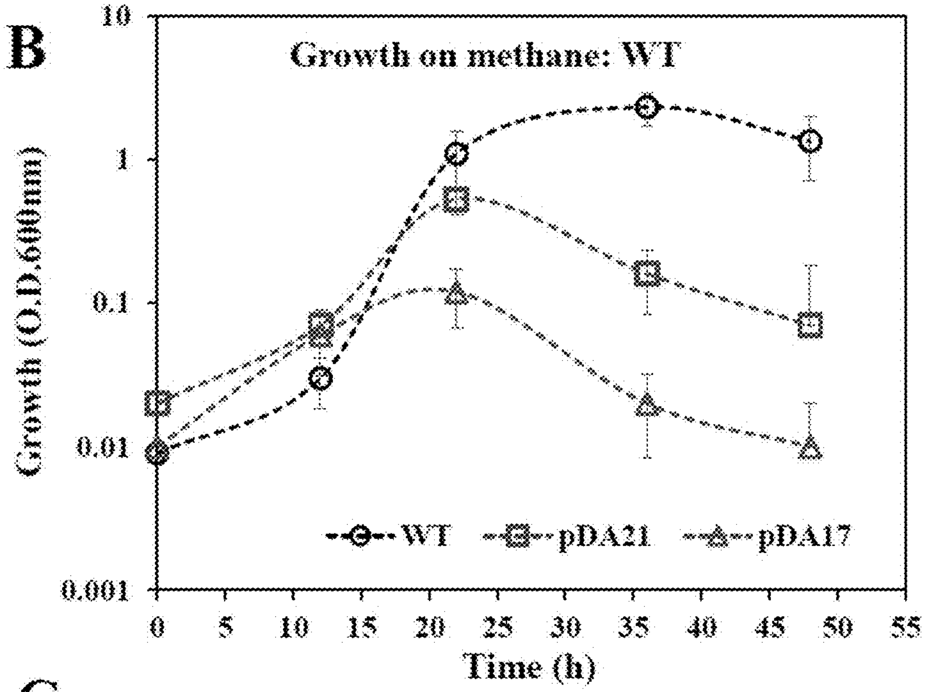
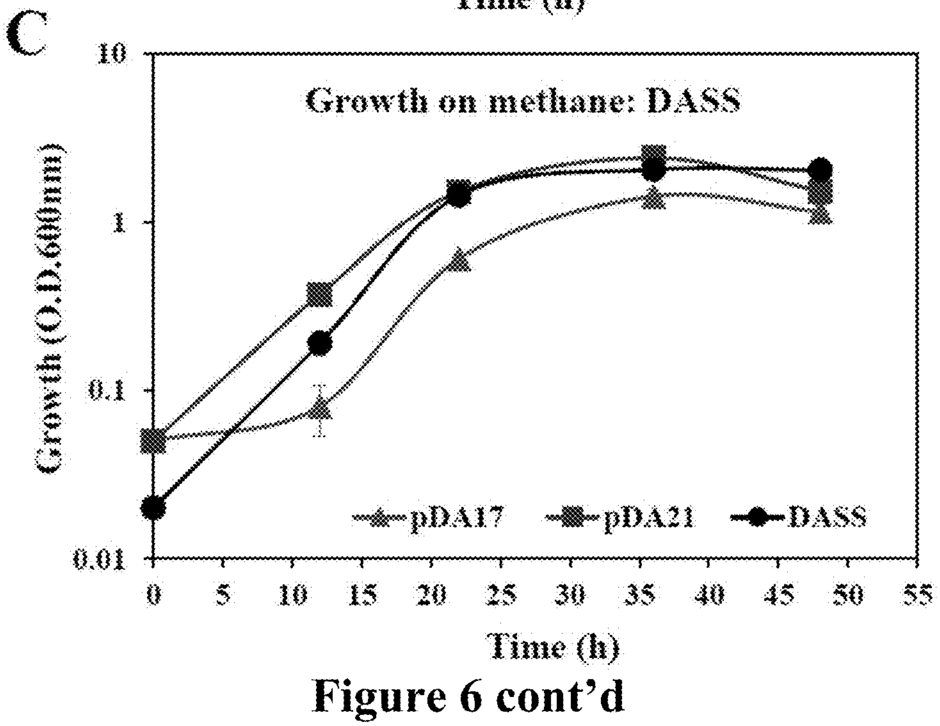
Figure 6 cont'd

| Fold Change | Gene name | Function/ Pathway |
|---|---|---|
| | secY | Protein transmembrane transport |
| | MEALZ_2553 | DUF2383 domain-containing protein |
| | mxaK | Component of methanol dehydorgenase |
| | nusA | Transcription elongation factor |
| | MEALZ_0105 | UC |
| | ftsH | Protein quality control |
| | ftsH | Protein quality control |
| | rplL | Translation (50S ribosomal protein) |
| | secG | Protein transmembrane transport |
| | ilvH | Isoleucine biosynthetic process |
| | MEALZ_3035 | EAL domain-containing protein |
| | adh | Acetaldehyde catabolic process |
| | corA | Cu and divalent cation transport |
| | MEALZ_1244 | UC |
| | MEALZ_2580 | Stress Response |
| | pma | Cation transport across plasma membrane |
| | MEALZ_0695 | UC |
| | guaB | Regulation of cell growth |
| | MEALZ_1822 | Electron transport Chain |
| | ppe | PPP (Ribulose-phosphate 3-epimerase) |
| | MEALZ_0447 | UC |
| | MEALZ_0439 | Peptidase: degradation of incorrectly synthesized proteins |
| | infC | Cold Shock response:translation initiation factor3 |
| | MEALZ_0811 | UC |
| | MEALZ_0967 | Putative: Calcium ion binding |
| | MEALZ_0170 | UC |
| | MEALZ_0519 | UC |
| | MEALZ_0244 | Putative membrane protein |
| | mdh | TCA: malate dehydrogenase |
| | rpsN | Translation: ribosomal small subunit assembly |
| | MEALZ_0586 | ompA like: outer membrane protein |
| | purA | Purine biosynthesis |
| | accC | Fatty acid biosynthesis |
| | nqrC | Na+ translocating oxidoreductase-repiratory chain |
| | gatB | Aspartyl/glutamyl-tRNA(Asn/Gln) amidotransferase-correctly charge tRNA |
| | hps2 | RUMP: 3-hexulose-6-phosphate synthase |
| | rpsF | 30S ribosomal subunit S6 (protein translation) |
| | MEALZ_1422 | TPR_REGION domain-containing protein |
| | MEALZ_1424 | Polysaccharide export OM protein |
| | MEALZ_1888 | UC |
| | MEALZ_3437 | UC |
| | MEALZ_0282 | Ferritin Dps: DNA protection during starvation from Fe induced free radicals |
| | MEALZ_2245 | UC |
| | mucD | Periplasmic serine endoprotease: misfolded protein degradation |
| | fae2 | Carbohydrate assimilation: formaldehyde-activating enzyme |
| | MEALZ_3978 | Putative peptidase |
| | pgm | Carbohydrate assimilation: phosphoglucomutase |
| | csp | Cold shock protein, RNA helicase co-factor, RNA co-chaperone |
| | mreB | Cell shape-determining protein MreB |
| | MEALZ_3963 | Probable Fe(2+)-trafficking protein |

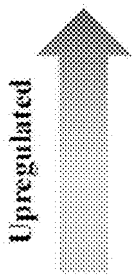

Figure 9

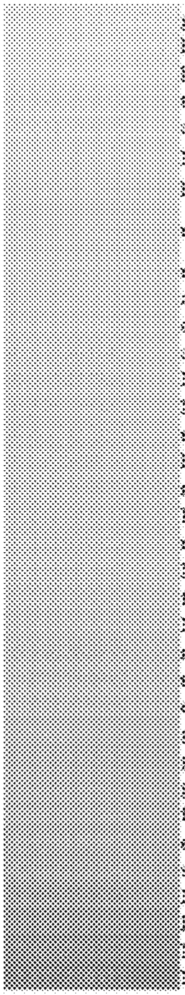

| | |
|---|---|
| groS | Chaperonin |
| hflC | Protein HflC |
| htpG | Chaperone protein HtpG |
| tsf | Protein synthesis elongation factor |
| acnB | TCA: aconitate hydratase B |
| MEALZ_3939 | Glycolysis/Gluconeogenesis: putative oxidoreductase 4Fe-FS cluster binding |
| hpi1 | RUMP: 3-hexulose-6-phosphate isomerase |
| mtdB | Carbohydrate metabolism: NAD(P)-dependent methylene tetrahydromethanopterin dehydrogenase |
| rplR | Translation: 50S ribosomal protein |
| atpH | ATP synthase |
| dapD | Lysine/ diaminopimelate biosynthesis |
| ask | Branched chain amino acid biosynthesis: Aspartokinase |
| MEALZ_2316 | redox regulation: Fe/ $O_2$ binding protein |
| MEALZ_1223 | Putative lipoprotein |
| rplC | Translation: 50S ribosomal protein L3 |
| hslU | Protein degradation: ATP-dependent protease |
| rplP | Translation: 50S ribosomal protein L16 |
| PPDK | Glycolysis: pyruvate, phosphate dikinase |
| rplD | Translation: 50S ribosomal protein L4 |
| MEALZ_3125 | Chaperone: outer membrane protein |
| ffh | Membrane protein translocation |
| MEALZ_3531 | CBS domain containing protein |
| rplJ | 50S ribosomal protein L10 |
| rplM | 50S ribosomal protein L13 |
| edd | Phosphogluconate dehydratase |
| glt | Glutamate synthesis |
| gap | Glycolysis/gluconeogenesis: glyceraldehyde-3-phosphate dehydrogenase |
| galU | Glycogen synthesis: UTP-glucose-1-phosphate uridylyltransferase |
| ftsZ | cell cycle/ cell division protein |
| erpA | Respiration: Fe-S cluster |
| sgaA | cellular response to DNA damage stimulus |
| MEALZ_1979 | UC |
| leuB | Branched amino acid synthesis: 3-isopropylmalate dehydrogenase |
| MEALZ_0971 | DUF4214 domain containing protein |
| MEALZ_1779 | Heat shock protein hsp20 |

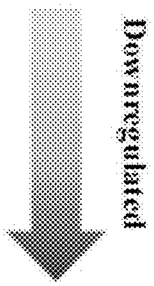

Figure 9 cont'd

METHODS AND COMPOSITIONS FOR THE PRODUCTION OF RHAMNOLIPID

CROSS-REFERENCE TO RELATED APPLICATIONS

This application claims priority to U.S. Provisional Patent Application Ser. No. 63/346,788, filed May 27, 2022, which is incorporated by reference in its entirety.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

REFERENCE TO SEQUENCE LISTING

The instant application contains a Sequence Listing which has been submitted electronically in XML format and is hereby incorporated by reference in its entirety. Said XML copy, created on Aug. 21, 2023, is named "2019-167-02 Sequence Listing.xml" and is 28 kilobytes in size.

FIELD OF THE INVENTION

The present invention is in the field of production of rhamnolipid.

BACKGROUND OF THE INVENTION

Production of surfactants and detergents is $41.3 billion dollar global industry[1]. Dominating this field are petroleum derived chemicals with surfactant properties. Biosurfactants are an attractive class of biomolecules that are sustainable replacements for petroleum derived surfactants[2-4]. In this group, rhamnolipids (RLs) have been classified as the next generation biosurfactants[3] because they are sustainably produced from renewable resources, are biodegradable, exhibit low toxicity and are highly reactive as emulsifiers[3,5]. RLs find application in oil recovery and remediation, as antimicrobial and/or antifungal agent, in detergent, cleaners, agriculture and cosmetics industry[2,6]. RLs belong to the class of microbial glycolipids and are predominantly produced at high titer by the opportunistic pathogen *Pseudomonas aeruginosa*[7,8] therefore, rhamnolipid biosynthesis, regulation and bioprocess development has been extensively studied in *P. aeruginosa*[2,6,7,9,10].

RLs are synthesized by diverting intermediates of bacterial fatty acid synthesis or β-oxidation to lipids and subsequently attaching L-rhamnose (sugar) moieties to the lipid chain, synthesizing the glycolipid[11]. The trans-2-alkanoyl-CoA intermediate of β-oxidation/fatty acid synthesis is first hydrated and isomerized to R-3-hydroxyalkanoyl-CoA by R-specific rhlY, rhlZ encoding enoyl-CoA hydratase/isomerase (FIG. 1). R-3-hydroxalkanoyl-CoA is the direct lipid precursor to β-D (β-D-hydroxyalkanoyloxy) alkanoic acid (HAA), synthesized by the activity of rhlA encoding 3-hydroxyacyl-ACP-O-3 hydroxyacyltransferase. Following that, rhamnosyl transferase encoded by rhlB attaches a rhamnose unit to the HAA chain and subsequently another rhamnose unit can be attached by rhlC (rhamnosyl transferase-2) making mono- and di-RL ($C_{10}$-$C_{10}$ HAA dominant in *P. aeruginosa*), respectively[11]. L-rhamnose is a deoxy sugar and an important component of lipopolysaccharide synthesis, so the rhamnose biosynthetic pathway is highly conserved and ubiquitous in both Gram-negative and Gram-positive bacteria[12]. In the native host *P. aeruginosa*, RLs are secreted in the medium to promote quorum sensing, biofilm formation, uptake of less soluble substrates and to act as virulence factors for the host[13,14]. With medium component and carbon source optimization, titers of >100 g/L of RL has been achieved in *P. aeruginosa* strains[15-17]. The high cost of substrates (glucose and additional hydrocarbons) and biosafety concerns related to the pathogenicity of *P. aeruginosa* has limited commercialization in food, agriculture, cosmetic and pharmaceutical applications[2,3,5,18]. Therefore, heterologous expression of RL synthetic pathway or isolation of native RL producing strains by industrially safe hosts has garnered much interest. *Burkholderia* spp. have been identified as alternative RL producer[19-20] and *E. coli* and *P. putida* have been explored as heterologous hosts that express the *P. aeruginosa* RL biosynthetic genes. The highest RL titer of 7.3 g/L was reported for engineered *P. putida* strains expressing rhlAB of *P. aeruginosa*[22,23]. The costs associated with mixed carbon-substrates and nitrogen source used in high titer RL production has been estimated to be 50% of the total production cost[2,24] Therefore, lower cost substrates are needed to improve the economics of RL production.

Methane is an abundantly available and low-cost feedstock. It is produced from a fossil source, natural gas, as well as from renewable source, biogas. Considering that methane is a highly potent greenhouse gas (GHG)[25,26] and one of the main target for climate-change mitigation, novel technologies for methane utilization are becoming the must element for all industries that produce methane as a by-product. Biogas, a mixture of $CH_4$ and $CO_2$, is the product of anaerobic digestion, whereas natural gas is found in abundance in the subsurface, and is comprised of >90% methane with impurities of volatile higher alkanes[26,27]. Since the U.S. has substantial reservoirs of natural gas (EIA 2018)[28] and an increasing capability to produce biogas[29,30], there is recent interest in methane as a feedstock for microbial conversion[27]. Methanotrophs are bacteria that are able to use methane as a sole carbon source for growth[31,32]. Recently, some methanotrophs, in particular, *Methylococcus capsulatus*, and *Methylotuvimicrobium buryatense* have emerged as microbial platforms for methane conversion to bio-based chemicals[33-35]. *Methylotuvimicrobium alcahphilum* (syn. *Methylomicrobium alcahphilum*) is an attractive methanotrophic host. *M. alcaliphilum* is a Gram-negative, haloalkaliphilic, obligate methanotroph that has been sequenced and for which basic genetic tools for engineering and gene expression have been developed[36-38].

Rhamnolipids, produced by the human opportunistic pathogen *Pseudomonas aeruginosa*, are glycolipid biomolecules that have been shown to be particularly effective bio-surfactants in applications from petroleum recovery to crop protection, soil treatment, pharmaceutical and food processing. Rhamnolipids have been discussed as a replacement for currently produced synthetic surfactant. However, high purity rhamnolipids are produced from organic substrates and are too costly to be employed on large scale. Recent studies of *P. aeruginosa* have established that medium chain (C8-C14) β-hydroxyacyl-CoAs, products of free fatty acid β-oxidation are precursors for rhamnolipids. rhlY, rhlZ, rhlA and rhlB encoding enoyl Co-A hydratase, isomerase and rhamnosyl transferase, respectively, are involved in the biosynthesis of rhamnolipids in *P. aeruginosa*.

Since pathogenic trait of *P. aeruginosa* possesses biosafety hazard for industrial processes and limits its commercialization in food, pharma and cosmetics, some attempts have been made previously in testing this pathway (rhlYZAB) in GRAS bacterial hosts. Heterologous production of rhamnolipids by expression of rhlYZAB gene cassette of *P. aeruginosa* in other host platforms like *Escherichia coli* and *Pseudomonas putida* has been plausible but with titer limitations and costly substrate supplementation. In recent years, methane is gaining popularity as a lucrative carbohydrate for microbial catalyzed bio-based chemical production due to its abundance in availability (renewable-waste land; non-renewable-natural gas) and lower cost compared to sugar based industrial processes and derived products.

SUMMARY OF THE INVENTION

The present invention provides for a method for producing a rhamnolipid, the method comprising: (a) providing a genetically modified host cell comprising one or more of RhlYZAB, or homologous enzyme(s) thereof, capable of expression in the host cell in a growth or culture medium; (b) growing or culturing the host cell such that the one or more of RhlYZAB, or homologous enzyme(s) thereof, are expressed and a rhamnolipid is produced; and (c) optionally recovering the rhamnolipid from the host cell or from the growth or culture medium. In some embodiments, the host cell is a methanotroph. In some embodiments, the growing or culturing step results in the host cell or methanotroph producing more rhamnolipid and/or fatty acids than the host cell or methanotroph in its unmodified form. In some embodiments, the growing or culturing step results in the host cell or methanotroph producing rhamnolipid at a concentration equal to or less than about 1.0 g/L, 1.5 g/L, 2.0 g/L, 2.5 g/L, 3.0 g/L, 3.5 g/L, 4.0 g/L, 4.5 g/L, or 5.0 g/L, or within a range of any two preceding values.

The present invention provides for a genetically modified host cell comprising one or more of RhlYZAB, or homologous enzyme(s) thereof, and one or more mutations in one or more endogenous genes described herein.

The present invention provides for a growth or culture medium comprising a genetically modified host cell of the present invention. In some embodiments, the growth or culture medium comprises methane. In some embodiments, methane is the sole carbon source in the growth or culture medium.

In some embodiments, the host cell comprises a nucleic acid encoding one or more of rhlYZAB, or homologous enzyme(s) thereof, operatively linked to one or more promoters capable of expressing rhlYZAB, or homologous enzyme(s) thereof, in the host cell. In some embodiments, the rhlYZAB is *Pseudomonas aeruginosa* rhlYZAB, or homologous enzymes thereof. In some embodiments, the rhlYZAB is in a rhlYZAB rhamnolipid cassette. In some embodiments, the rhlYZAB or rhlYZAB rhamnolipid cassette is on a vector, plasmid, or plasmid-based system. In some embodiments, the rhlYZAB gene(s), or homologous enzyme(s) thereof, are codon optimized for the host cell. In some embodiments, the host cell in the unmodified form does not produce rhamnolipid. In some embodiments, the host cell does not have any native rhlYZAB.

In some embodiments, the host cell is a methanotroph. A methanotroph is a bacterium that is able to use methane as a sole carbon source for growth. In some embodiments, the methanotroph is a Gram-negative, haloalkaliphilic, and/or obligate methanotroph. In some embodiments, the host cell is a methanotroph is a *Methylococcus* or *Methylotuvimicrobium* cell. In some embodiments, the *Methylotuvimicrobium* cell is a *Methylotuvimicrobium buryatense* or *Methylotuvimicrobium alcahphilum* (syn. *Methylomicrobium alcahphilum*). *M. alcaliphilum* is a Gram-negative, haloalkaliphilic, obligate methanotroph that has been sequenced and for which basic genetic tools for engineering and gene expression have been developed.

The present invention provides for a methanotroph comprising one or more, or all, of the mutations indicated in the Appendix of U.S. Provisional Patent Application Ser. No. 63/346,788, filed May 27, 2022, which is incorporated by reference in its entirety (hereafter "the Appendix"). In some embodiments, the host cell or methanotroph comprises one or more, or all, of the mutations indicated in the Appendix. In some embodiments, the host cell or methanotroph comprises mutations in the genes of one or more, or all, of the following: IS3 family transposase (gene-MEALZ_RS03460, gene-MEALZ_RS08615, gene-MEALZ_RS11580); autotransporter outer membrane beta-barrel domain-containing protein (gene-MEALZ_RS22650); Crp/Fnr family transcriptional regulator (gene-MEALZ_RS12360); multicopper oxidase domain-containing protein (gene-MEALZ_RS14455); type IV pilus secretin PilQ (pilQ; gene-MEALZ_RS15795); and, FAD-dependent oxidoreductase/hypothetical protein/NAD(P)/FAD-dependent oxidoreductase (gene-MEALZ_RS18045). In some embodiments, the host cell or methanotroph comprises endogenous genes of one or more, or all, of the genes/proteins indicated in the Appendix, or for IS3 family transposase; autotransporter outer membrane beta-barrel domain-containing protein; Crp/Fnr family transcriptional regulator; multicopper oxidase domain-containing protein; type IV pilus secretin PilQ; and, FAD-dependent oxidoreductase/hypothetical protein/NAD(P)/FAD-dependent oxidoreductase.

In some embodiments, the host cell or methanotroph comprises one or more, or all, of the mutations indicated in Table 4. In some embodiments, the host cell or methanotroph comprises mutations in one or more of the following genes: MEALZ_RS01195, MEALZ_RS01280, MEALZ_RS01285, MEALZ_RS01290,fabG, MEALZ_RS01300, MEALZ_RS01305, MEALZ_RS02270, MEALZ_RS02405, murA, MEALZ_RS04765, dxs, tssJ, MEALZ_RS06900, MEALZ_RS06905,folD, MEALZ_RS08615, MEALZ_RS11580, MEALZ_RS16020, MEALZ_RS17985, MEALZ_RS18045, MEALZ_RS18060, MEALZ_RS18075, MEALZ_RS18090, MEALZ_RS18120, MEALZ_RS18840, tkt, and MEALZ_RS21105. In some embodiments, the host cell or methanotroph comprises mutations in at least 2, 3, 4, 5, 6, 7, 8, 9, 10, 11, 12, 13, 14, 15, 16, 1, 18, 19, 20, 21, 22, 23, 24, 25, 26, 27, or 28, or more, of the preceding listed genes.

TABLE 4

Mutations of the host cell that increase RL production.

| #CHROM | POS | REF | ALT | DASS_2_ Genotype | ANNO | GENE_ID | GENE_NAME |
|---|---|---|---|---|---|---|---|
| NC_016112.1 | 257711 | T | C | 186/186 | gene | gene-MEALZ_RS01195 | MEALZ_RS01195 |
| NC_016112.1 | 274084 | A | C | 65/65 | gene | gene-MEALZ_RS01260 | MEALZ_RS01260 |
| NC_016112.1 | 274102 | A | G | 83/83 | gene | gene-MEALZ_RS01260 | MEALZ_RS01260 |
| NC_016112.1 | 274387 | C | T | 188/188 | gene | gene-MEALZ_RS01260 | MEALZ_RS01260 |
| NC_016112.1 | 274678 | T | C | 195/195 | gene | gene-MEALZ_RS01260 | MEALZ_RS01260 |
| NC_016112.1 | 274869 | C | T | 222/222 | gene | gene-MEALZ_RS01260 | MEALZ_RS01260 |
| NC_016112.1 | 275047 | T | C | 201/201 | gene | gene-MEALZ_RS01260 | MEALZ_RS01260 |
| NC_016112.1 | 275049 | G | A | 204/204 | gene | gene-MEALZ_RS01260 | MEALZ_RS01260 |
| NC_016112.1 | 275058 | C | T | 199/199 | gene | gene-MEALZ_RS01260 | MEALZ_RS01260 |
| NC_016112.1 | 275059 | G | T | 198/198 | gene | gene-MEALZ_RS01260 | MEALZ_RS01260 |
| NC_016112.1 | 275081 | C | T | 200/200 | gene | gene-MEALZ_RS01260 | MEALZ_RS01260 |
| NC_016112.1 | 275093 | C | T | 190/190 | gene | gene-MEALZ_RS01260 | MEALZ_RS01260 |
| NC_016112.1 | 275110 | T | C | 193/193 | gene | gene-MEALZ_RS01260 | MEALZ_RS01260 |
| NC_016112.1 | 278205 | C | G | 220/220 | gene | gene-MEALZ_RS01275 | MEALZ_RS01275 |
| NC_016112.1 | 278215 | A | G | 224/224 | gene | gene-MEALZ_RS01275 | MEALZ_RS01275 |
| NC_016112.1 | 278222 | T | G | 215/215 | gene | gene-MEALZ_RS01275 | MEALZ_RS01275 |
| NC_016112.1 | 278240 | G | A | 214/214 | gene | gene-MEALZ_RS01275 | MEALZ_RS01275 |
| NC_016112.1 | 278284 | G | A | 212/212 | gene | gene-MEALZ_RS01275 | MEALZ_RS01275 |
| NC_016112.1 | 278386 | G | A | 183/183 | gene | gene-MEALZ_RS01275 | MEALZ_RS01275 |
| NC_016112.1 | 278466 | G | T | 148/148 | Inter-genetic | . | . |
| NC_016112.1 | 278490 | A | G | 119/119 | Inter-genetic | . | . |
| NC_016112.1 | 278492 | T | C | 118/118 | Inter-genetic | . | . |
| NC_016112.1 | 278494 | G | T | 115/115 | Inter-genetic | . | . |
| NC_016112.1 | 278514 | T | A | 71/71 | Inter-genetic | . | . |
| NC_016112.1 | 278515 | C | G | 71/71 | Inter-genetic | . | . |
| NC_016112.1 | 278517 | C | T | 67/67 | Inter-genetic | . | . |
| NC_016112.1 | 278521 | G | A | 65/65 | Inter-genetic | . | . |
| NC_016112.1 | 278545 | A | G | 24/24 | Inter-genetic | . | . |
| NC_016112.1 | 279003 | A | G | 76/76 | gene | gene-MEALZ_RS01280 | MEALZ_RS01280 |
| NC_016112.1 | 279129 | C | T | 164/164 | gene | gene-MEALZ_RS01280 | MEALZ_RS01280 |
| NC_016112.1 | 279280 | G | T | 165/165 | gene | gene-MEALZ_RS01280 | MEALZ_RS01280 |
| NC_016112.1 | 279714 | T | C | 179/179 | gene | gene-MEALZ_RS01280 | MEALZ_RS01280 |
| NC_016112.1 | 279721 | T | C | 182/182 | gene | gene-MEALZ_RS01280 | MEALZ_RS01280 |
| NC_016112.1 | 279732 | C | G | 181/181 | gene | gene-MEALZ_RS01280 | MEALZ_RS01280 |
| NC_016112.1 | 280003 | A | C | 196/196 | gene | gene-MEALZ_RS01280 | MEALZ_RS01280 |
| NC_016112.1 | 280038 | T | C | 174/174 | gene | gene-MEALZ_RS01280 | MEALZ_RS01280 |
| NC_016112.1 | 280048 | A | G | 180/180 | gene | gene-MEALZ_RS01280 | MEALZ_RS01280 |
| NC_016112.1 | 280050 | T | C | 179/179 | gene | gene-MEALZ_RS01280 | MEALZ_RS01280 |
| NC_016112.1 | 280053 | C | T | 179/179 | gene | gene-MEALZ_RS01280 | MEALZ_RS01280 |
| NC_016112.1 | 280077 | C | T | 178/178 | gene | gene-MEALZ_RS01280 | MEALZ_RS01280 |
| NC_016112.1 | 280080 | G | A | 177/177 | gene | gene-MEALZ_RS01280 | MEALZ_RS01280 |
| NC_016112.1 | 280256 | G | A | 174/174 | gene | gene-MEALZ_RS01285 | MEALZ_RS01285 |
| NC_016112.1 | 280275 | T | C | 159/159 | gene | gene-MEALZ_RS01285 | MEALZ_RS01285 |
| NC_016112.1 | 280293 | T | C | 148/148 | gene | gene-MEALZ_RS01285 | MEALZ_RS01285 |
| NC_016112.1 | 280317 | C | A | 165/165 | gene | gene-MEALZ_RS01285 | MEALZ_RS01285 |
| NC_016112.1 | 280322 | A | G | 165/165 | gene | gene-MEALZ_RS01285 | MEALZ_RS01285 |
| NC_016112.1 | 280378 | T | C | 155/155 | gene | gene-MEALZ_RS01285 | MEALZ_RS01285 |
| NC_016112.1 | 280393 | C | G | 157/157 | gene | gene-MEALZ_RS01285 | MEALZ_RS01285 |
| NC_016112.1 | 280402 | T | C | 154/154 | gene | gene-MEALZ_RS01285 | MEALZ_RS01285 |
| NC_016112.1 | 280495 | T | C | 145/145 | gene | gene-MEALZ_RS01285 | MEALZ_RS01285 |
| NC_016112.1 | 280585 | T | C | 154/154 | gene | gene-MEALZ_RS01285 | MEALZ_RS01285 |
| NC_016112.1 | 280588 | A | C | 154/154 | gene | gene-MEALZ_RS01285 | MEALZ_RS01285 |
| NC_016112.1 | 280630 | A | G | 152/152 | gene | gene-MEALZ_RS01285 | MEALZ_RS01285 |
| NC_016112.1 | 280681 | C | A | 149/149 | gene | gene-MEALZ_RS01285 | MEALZ_RS01285 |
| NC_016112.1 | 280705 | C | T | 169/169 | gene | gene-MEALZ_RS01285 | MEALZ_RS01285 |
| NC_016112.1 | 280708 | T | C | 170/170 | gene | gene-MEALZ_RS01285 | MEALZ_RS01285 |
| NC_016112.1 | 280711 | C | T | 166/166 | gene | gene-MEALZ_RS01285 | MEALZ_RS01285 |
| NC_016112.1 | 280714 | G | T | 167/167 | gene | gene-MEALZ_RS01285 | MEALZ_RS01285 |
| NC_016112.1 | 280717 | T | C | 168/168 | gene | gene-MEALZ_RS01285 | MEALZ_RS01285 |
| NC_016112.1 | 280729 | T | C | 164/164 | gene | gene-MEALZ_RS01285 | MEALZ_RS01285 |
| NC_016112.1 | 280731 | T | C | 164/164 | gene | gene-MEALZ_RS01285 | MEALZ_RS01285 |
| NC_016112.1 | 280754 | C | T | 171/171 | gene | gene-MEALZ_RS01285 | MEALZ_RS01285 |
| NC_016112.1 | 280825 | T | G | 136/136 | gene | gene-MEALZ_RS01285 | MEALZ_RS01285 |
| NC_016112.1 | 280885 | C | T | 134/134 | gene | gene-MEALZ_RS01285 | MEALZ_RS01285 |
| NC_016112.1 | 280913 | A | G | 142/142 | gene | gene-MEALZ_RS01285 | MEALZ_RS01285 |
| NC_016112.1 | 280914 | T | C | 143/143 | gene | gene-MEALZ_RS01285 | MEALZ_RS01285 |

TABLE 4-continued

Mutations of the host cell that increase RL production.

| #CHROM | POS | REF | ALT | DASS_2_ Genotype | ANNO | GENE_ID | GENE_NAME |
|---|---|---|---|---|---|---|---|
| NC_016112.1 | 280936 | C | A | 141/141 | gene | gene-MEALZ_RS01285 | MEALZ_RS01285 |
| NC_016112.1 | 280957 | T | C | 141/141 | gene | gene-MEALZ_RS01285 | MEALZ_RS01285 |
| NC_016112.1 | 281142 | A | G | 158/158 | gene | gene-MEALZ_RS01285 | MEALZ_RS01285 |
| NC_016112.1 | 281323 | G | A | 208/208 | gene | gene-MEALZ_RS01285 | MEALZ_RS01285 |
| NC_016112.1 | 281338 | A | G | 216/216 | gene | gene-MEALZ_RS01285 | MEALZ_RS01285 |
| NC_016112.1 | 281353 | A | G | 223/223 | gene | gene-MEALZ_RS01285 | MEALZ_RS01285 |
| NC_016112.1 | 281461 | T | A | 204/204 | gene | gene-MEALZ_RS01290 | MEALZ_RS01290 |
| NC_016112.1 | 281638 | C | T | 186/186 | gene | gene-MEALZ_RS01290 | MEALZ_RS01290 |
| NC_016112.1 | 282166 | C | A | 157/157 | Inter-genetic | . | . |
| NC_016112.1 | 282168 | G | A | 166/166 | Inter-genetic | . | . |
| NC_016112.1 | 282169 | C | T | 166/166 | Inter-genetic | . | . |
| NC_016112.1 | 282235 | A | T | 160/160 | Inter-genetic | . | . |
| NC_016112.1 | 282262 | A | T | 167/167 | gene | gene-MEALZ_RS01295 | fabG |
| NC_016112.1 | 282400 | C | T | 163/163 | gene | gene-MEALZ_RS01295 | fabG |
| NC_016112.1 | 282479 | T | C | 162/162 | gene | gene-MEALZ_RS01295 | fabG |
| NC_016112.1 | 282486 | C | T | 157/157 | gene | gene-MEALZ_RS01295 | fabG |
| NC_016112.1 | 282727 | C | T | 156/156 | gene | gene-MEALZ_RS01295 | fabG |
| NC_016112.1 | 282835 | T | C | 153/153 | gene | gene-MEALZ_RS01295 | fabG |
| NC_016112.1 | 282955 | C | T | 125/125 | gene | gene-MEALZ_RS01295 | fabG |
| NC_016112.1 | 282965 | T | C | 132/132 | gene | gene-MEALZ_RS01295 | fabG |
| NC_016112.1 | 282967 | G | A | 129/129 | gene | gene-MEALZ_RS01295 | fabG |
| NC_016112.1 | 283006 | A | C | 140/140 | gene | gene-MEALZ_RS01300 | MEALZ_RS01300 |
| NC_016112.1 | 283043 | A | T | 151/152 | gene | gene-MEALZ_RS01300 | MEALZ_RS01300 |
| NC_016112.1 | 283077 | G | T | 158/158 | gene | gene-MEALZ_RS01300 | MEALZ_RS01300 |
| NC_016112.1 | 283164 | G | A | 147/147 | gene | gene-MEALZ_RS01300 | MEALZ_RS01300 |
| NC_016112.1 | 283170 | A | G | 144/144 | gene | gene-MEALZ_RS01300 | MEALZ_RS01300 |
| NC_016112.1 | 283173 | G | C | 144/144 | gene | gene-MEALZ_RS01300 | MEALZ_RS01300 |
| NC_016112.1 | 283185 | G | A | 143/143 | gene | gene-MEALZ_RS01300 | MEALZ_RS01300 |
| NC_016112.1 | 283216 | T | C | 151/153 | gene | gene-MEALZ_RS01300 | MEALZ_RS01300 |
| NC_016112.1 | 283236 | A | T | 155/156 | gene | gene-MEALZ_RS01300 | MEALZ_RS01300 |
| NC_016112.1 | 283248 | C | T | 163/163 | gene | gene-MEALZ_RS01300 | MEALZ_RS01300 |
| NC_016112.1 | 283275 | G | A | 174/174 | gene | gene-MEALZ_RS01300 | MEALZ_RS01300 |
| NC_016112.1 | 283278 | C | T | 174/174 | gene | gene-MEALZ_RS01300 | MEALZ_RS01300 |
| NC_016112.1 | 283336 | C | T | 213/213 | gene | gene-MEALZ_RS01300 | MEALZ_RS01300 |
| NC_016112.1 | 283365 | G | C | 213/213 | gene | gene-MEALZ_RS01300 | MEALZ_RS01300 |
| NC_016112.1 | 283389 | G | A | 208/208 | gene | gene-MEALZ_RS01300 | MEALZ_RS01300 |
| NC_016112.1 | 283395 | C | T | 197/198 | gene | gene-MEALZ_RS01300 | MEALZ_RS01300 |
| NC_016112.1 | 283440 | T | C | 198/198 | gene | gene-MEALZ_RS01300 | MEALZ_RS01300 |
| NC_016112.1 | 283458 | T | C | 205/205 | gene | gene-MEALZ_RS01300 | MEALZ_RS01300 |
| NC_016112.1 | 283461 | T | C | 202/202 | gene | gene-MEALZ_RS01300 | MEALZ_RS01300 |
| NC_016112.1 | 283503 | C | T | 185/185 | gene | gene-MEALZ_RS01300 | MEALZ_RS01300 |
| NC_016112.1 | 283533 | A | C | 185/185 | gene | gene-MEALZ_RS01300 | MEALZ_RS01300 |
| NC_016112.1 | 283572 | G | A | 183/183 | gene | gene-MEALZ_RS01300 | MEALZ_RS01300 |
| NC_016112.1 | 283578 | C | T | 183/183 | gene | gene-MEALZ_RS01300 | MEALZ_RS01300 |
| NC_016112.1 | 283629 | T | C | 183/183 | gene | gene-MEALZ_RS01300 | MEALZ_RS01300 |
| NC_016112.1 | 283641 | G | T | 180/180 | gene | gene-MEALZ_RS01300 | MEALZ_RS01300 |
| NC_016112.1 | 283647 | C | T | 178/178 | gene | gene-MEALZ_RS01300 | MEALZ_RS01300 |
| NC_016112.1 | 283792 | A | G | 148/148 | gene | gene-MEALZ_RS01300 | MEALZ_RS01300 |
| NC_016112.1 | 283869 | A | G | 178/178 | gene | gene-MEALZ_RS01300 | MEALZ_RS01300 |
| NC_016112.1 | 283893 | T | C | 187/187 | gene | gene-MEALZ_RS01300 | MEALZ_RS01300 |
| NC_016112.1 | 283920 | A | C | 192/192 | gene | gene-MEALZ_RS01300 | MEALZ_RS01300 |
| NC_016112.1 | 283934 | G | A | 187/187 | gene | gene-MEALZ_RS01300 | MEALZ_RS01300 |
| NC_016112.1 | 283953 | A | G | 178/178 | gene | gene-MEALZ_RS01300 | MEALZ_RS01300 |
| NC_016112.1 | 283974 | T | C | 182/182 | gene | gene-MEALZ_RS01300 | MEALZ_RS01300 |
| NC_016112.1 | 284034 | T | C | 181/181 | gene | gene-MEALZ_RS01300 | MEALZ_RS01300 |
| NC_016112.1 | 284040 | C | T | 184/184 | gene | gene-MEALZ_RS01300 | MEALZ_RS01300 |
| NC_016112.1 | 284046 | G | A | 174/174 | gene | gene-MEALZ_RS01300 | MEALZ_RS01300 |
| NC_016112.1 | 284103 | A | G | 188/188 | gene | gene-MEALZ_RS01300 | MEALZ_RS01300 |
| NC_016112.1 | 284107 | G | A | 190/190 | gene | gene-MEALZ_RS01300 | MEALZ_RS01300 |
| NC_016112.1 | 284273 | T | C | 214/214 | gene | gene-MEALZ_RS01305 | MEALZ_RS01305 |
| NC_016112.1 | 284392 | C | G | 225/225 | gene | gene-MEALZ_RS01305 | MEALZ_RS01305 |
| NC_016112.1 | 284394 | G | A | 225/225 | gene | gene-MEALZ_RS01305 | MEALZ_RS01305 |
| NC_016112.1 | 284395 | G | C | 222/222 | gene | gene-MEALZ_RS01305 | MEALZ_RS01305 |
| NC_016112.1 | 284399 | G | A | 223/223 | gene | gene-MEALZ_RS01305 | MEALZ_RS01305 |
| NC_016112.1 | 284404 | C | T | 216/216 | gene | gene-MEALZ_RS01305 | MEALZ_RS01305 |
| NC_016112.1 | 284407 | G | A | 214/214 | gene | gene-MEALZ_RS01305 | MEALZ_RS01305 |
| NC_016112.1 | 284534 | A | C | 173/173 | gene | gene-MEALZ_RS01305 | MEALZ_RS01305 |
| NC_016112.1 | 284560 | C | A | 163/163 | gene | gene-MEALZ_RS01305 | MEALZ_RS01305 |
| NC_016112.1 | 284571 | G | C | 161/161 | gene | gene-MEALZ_RS01305 | MEALZ_RS01305 |
| NC_016112.1 | 284605 | G | T | 156/156 | gene | gene-MEALZ_RS01305 | MEALZ_RS01305 |
| NC_016112.1 | 284710 | C | T | 171/171 | gene | gene-MEALZ_RS01305 | MEALZ_RS01305 |

TABLE 4-continued

Mutations of the host cell that increase RL production.

| #CHROM | POS | REF | ALT | DASS_2_ Genotype | ANNO | GENE_ID | GENE_NAME |
|---|---|---|---|---|---|---|---|
| NC_016112.1 | 284748 | C | T | 180/180 | gene | gene-MEALZ_RS01305 | MEALZ_RS01305 |
| NC_016112.1 | 284829 | A | G | 193/193 | gene | gene-MEALZ_RS01305 | MEALZ_RS01305 |
| NC_016112.1 | 284833 | A | G | 192/192 | gene | gene-MEALZ_RS01305 | MEALZ_RS01305 |
| NC_016112.1 | 284857 | G | A | 197/197 | gene | gene-MEALZ_RS01305 | MEALZ_RS01305 |
| NC_016112.1 | 284860 | C | T | 202/202 | gene | gene-MEALZ_RS01305 | MEALZ_RS01305 |
| NC_016112.1 | 284866 | C | T | 202/202 | gene | gene-MEALZ_RS01305 | MEALZ_RS01305 |
| NC_016112.1 | 284869 | A | G | 203/203 | gene | gene-MEALZ_RS01305 | MEALZ_RS01305 |
| NC_016112.1 | 284870 | A | C | 201/201 | gene | gene-MEALZ_RS01305 | MEALZ_RS01305 |
| NC_016112.1 | 284872 | G | A | 200/200 | gene | gene-MEALZ_RS01305 | MEALZ_RS01305 |
| NC_016112.1 | 284909 | G | A | 190/190 | gene | gene-MEALZ_RS01305 | MEALZ_RS01305 |
| NC_016112.1 | 284912 | G | A | 190/190 | gene | gene-MEALZ_RS01305 | MEALZ_RS01305 |
| NC_016112.1 | 284924 | C | T | 181/181 | gene | gene-MEALZ_RS01305 | MEALZ_RS01305 |
| NC_016112.1 | 284926 | G | T | 184/184 | gene | gene-MEALZ_RS01305 | MEALZ_RS01305 |
| NC_016112.1 | 284935 | G | A | 177/177 | gene | gene-MEALZ_RS01305 | MEALZ_RS01305 |
| NC_016112.1 | 284943 | G | A | 183/183 | gene | gene-MEALZ_RS01305 | MEALZ_RS01305 |
| NC_016112.1 | 284983 | A | C | 167/167 | gene | gene-MEALZ_RS01305 | MEALZ_RS01305 |
| NC_016112.1 | 284987 | C | T | 167/167 | gene | gene-MEALZ_RS01305 | MEALZ_RS01305 |
| NC_016112.1 | 284989 | A | G | 162/162 | gene | gene-MEALZ_RS01305 | MEALZ_RS01305 |
| NC_016112.1 | 285002 | C | T | 156/156 | gene | gene-MEALZ_RS01305 | MEALZ_RS01305 |
| NC_016112.1 | 285006 | A | G | 152/152 | gene | gene-MEALZ_RS01305 | MEALZ_RS01305 |
| NC_016112.1 | 285007 | A | C | 153/153 | gene | gene-MEALZ_RS01305 | MEALZ_RS01305 |
| NC_016112.1 | 285010 | T | G | 154/154 | gene | gene-MEALZ_RS01305 | MEALZ_RS01305 |
| NC_016112.1 | 285011 | C | T | 153/153 | gene | gene-MEALZ_RS01305 | MEALZ_RS01305 |
| NC_016112.1 | 285019 | T | G | 154/154 | gene | gene-MEALZ_RS01305 | MEALZ_RS01305 |
| NC_016112.1 | 285020 | A | G | 155/155 | gene | gene-MEALZ_RS01305 | MEALZ_RS01305 |
| NC_016112.1 | 285023 | A | G | 160/160 | gene | gene-MEALZ_RS01305 | MEALZ_RS01305 |
| NC_016112.1 | 285033 | G | A | 162/162 | gene | gene-MEALZ_RS01305 | MEALZ_RS01305 |
| NC_016112.1 | 285053 | T | A | 153/153 | gene | gene-MEALZ_RS01305 | MEALZ_RS01305 |
| NC_016112.1 | 285058 | G | C | 152/152 | gene | gene-MEALZ_RS01305 | MEALZ_RS01305 |
| NC_016112.1 | 285062 | C | T | 149/149 | gene | gene-MEALZ_RS01305 | MEALZ_RS01305 |
| NC_016112.1 | 285068 | T | G | 157/157 | gene | gene-MEALZ_RS01305 | MEALZ_RS01305 |
| NC_016112.1 | 285069 | C | T | 156/156 | gene | gene-MEALZ_RS01305 | MEALZ_RS01305 |
| NC_016112.1 | 285076 | G | A | 153/153 | gene | gene-MEALZ_RS01305 | MEALZ_RS01305 |
| NC_016112.1 | 285088 | T | C | 147/147 | gene | gene-MEALZ_RS01305 | MEALZ_RS01305 |
| NC_016112.1 | 285091 | A | G | 142/142 | gene | gene-MEALZ_RS01305 | MEALZ_RS01305 |
| NC_016112.1 | 285092 | C | T | 139/139 | gene | gene-MEALZ_RS01305 | MEALZ_RS01305 |
| NC_016112.1 | 285095 | A | G | 143/143 | gene | gene-MEALZ_RS01305 | MEALZ_RS01305 |
| NC_016112.1 | 285100 | T | A | 142/142 | gene | gene-MEALZ_RS01305 | MEALZ_RS01305 |
| NC_016112.1 | 285109 | G | T | 148/148 | gene | gene-MEALZ_RS01305 | MEALZ_RS01305 |
| NC_016112.1 | 285114 | T | C | 150/150 | gene | gene-MEALZ_RS01305 | MEALZ_RS01305 |
| NC_016112.1 | 285115 | T | C | 149/149 | gene | gene-MEALZ_RS01305 | MEALZ_RS01305 |
| NC_016112.1 | 285118 | A | G | 149/149 | gene | gene-MEALZ_RS01305 | MEALZ_RS01305 |
| NC_016112.1 | 285153 | G | A | 159/159 | gene | gene-MEALZ_RS01305 | MEALZ_RS01305 |
| NC_016112.1 | 503932 | A | G | 42/284 | Inter-genetic | . | . |
| NC_016112.1 | 503936 | T | C | 49/289 | Inter-genetic | . | . |
| NC_016112.1 | 503940 | G | A | 55/297 | Inter-genetic | . | . |
| NC_016112.1 | 503945 | A | G | 57/292 | Inter-genetic | . | . |
| NC_016112.1 | 503949 | A | C | 58/292 | Inter-genetic | . | . |
| NC_016112.1 | 503970 | C | T | 91/310 | Inter-genetic | . | . |
| NC_016112.1 | 503972 | G | A | 91/310 | Inter-genetic | . | . |
| NC_016112.1 | 503979 | A | G | 98/306 | Inter-genetic | . | . |
| NC_016112.1 | 504062 | C | A | 174/364 | gene | gene-MEALZ_RS02270 | MEALZ_RS02270 |
| NC_016112.1 | 504071 | A | G | 179/372 | gene | gene-MEALZ_RS02270 | MEALZ_RS02270 |
| NC_016112.1 | 504073 | T | A | 178/369 | gene | gene-MEALZ_RS02270 | MEALZ_RS02270 |
| NC_016112.1 | 504091 | C | G | 181/371 | gene | gene-MEALZ_RS02270 | MEALZ_RS02270 |
| NC_016112.1 | 504109 | T | C | 170/344 | gene | gene-MEALZ_RS02270 | MEALZ_RS02270 |
| NC_016112.1 | 504856 | A | T | 117/252 | gene | gene-MEALZ_RS02270 | MEALZ_RS02270 |
| NC_016112.1 | 504907 | C | T | 102/217 | gene | gene-MEALZ_RS02270 | MEALZ_RS02270 |
| NC_016112.1 | 538607 | G | C | 170/170 | gene | gene-MEALZ_RS02405 | MEALZ_RS02405 |
| NC_016112.1 | 705301 | C | G | 215/215 | gene | gene-MEALZ_RS03100 | murA |
| NC_016112.1 | 790204 | G | A | 3/23 | Inter-genetic | . | . |
| NC_016112.1 | 1075721 | C | A | 34/192 | Inter-genetic | . | . |

TABLE 4-continued

Mutations of the host cell that increase RL production.

| #CHROM | POS | REF | ALT | DASS_2_ Genotype | ANNO | GENE_ID | GENE_NAME |
|---|---|---|---|---|---|---|---|
| NC_016112.1 | 1116663 | C | G | 124/124 | gene | gene-MEALZ_RS04765 | MEALZ_RS04765 |
| NC_016112.1 | 1116664 | G | C | 124/124 | gene | gene-MEALZ_RS04765 | MEALZ_RS04765 |
| NC_016112.1 | 1330008 | G | T | 47/196 | Inter-genetic | . | . |
| NC_016112.1 | 1330095 | A | G | 33/179 | Inter-genetic | . | . |
| NC_016112.1 | 1393728 | C | T | 89/234 | Inter-genetic | . | . |
| NC_016112.1 | 1419041 | T | C | 135/135 | Inter-genetic | . | . |
| NC_016112.1 | 1439362 | C | A | 93/94 | Inter-genetic | . | . |
| NC_016112.1 | 1479855 | T | C | 179/361 | gene | gene-MEALZ_RS06450 | dxs |
| NC_016112.1 | 1480356 | C | T | 164/372 | gene | gene-MEALZ_RS06450 | dxs |
| NC_016112.1 | 1593190 | T | A | 183/183 | gene | gene-MEALZ_RS06895 | tssJ |
| NC_016112.1 | 1593227 | A | G | 202/202 | gene | gene-MEALZ_RS06895 | tssJ |
| NC_016112.1 | 1593247 | G | A | 199/199 | gene | gene-MEALZ_RS06895 | tssJ |
| NC_016112.1 | 1593316 | G | A | 189/189 | gene | gene-MEALZ_RS06895 | tssJ |
| NC_016112.1 | 1593337 | T | C | 202/202 | gene | gene-MEALZ_RS06895 | tssJ |
| NC_016112.1 | 1593340 | G | A | 200/200 | gene | gene-MEALZ_RS06895 | tssJ |
| NC_016112.1 | 1593353 | T | C | 190/190 | gene | gene-MEALZ_RS06895 | tssJ |
| NC_016112.1 | 1593360 | C | T | 191/191 | gene | gene-MEALZ_RS06895 | tssJ |
| NC_016112.1 | 1593364 | C | T | 191/191 | gene | gene-MEALZ_RS06895 | tssJ |
| NC_016112.1 | 1593444 | T | G | 197/197 | gene | gene-MEALZ_RS06895 | tssJ |
| NC_016112.1 | 1593445 | T | G | 197/197 | gene | gene-MEALZ_RS06895 | tssJ |
| NC_016112.1 | 1593520 | G | A | 186/186 | gene | gene-MEALZ_RS06895 | tssJ |
| NC_016112.1 | 1593525 | G | A | 185/185 | gene | gene-MEALZ_RS06895 | tssJ |
| NC_016112.1 | 1593540 | T | G | 180/181 | gene | gene-MEALZ_RS06895 | tssJ |
| NC_016112.1 | 1593565 | G | A | 176/176 | gene | gene-MEALZ_RS06895 | tssJ |
| NC_016112.1 | 1593577 | T | C | 180/180 | gene | gene-MEALZ_RS06895 | tssJ |
| NC_016112.1 | 1593583 | T | C | 186/186 | gene | gene-MEALZ_RS06895 | tssJ |
| NC_016112.1 | 1593586 | C | T | 184/184 | gene | gene-MEALZ_RS06895 | tssJ |
| NC_016112.1 | 1593589 | C | G | 185/185 | gene | gene-MEALZ_RS06895 | tssJ |
| NC_016112.1 | 1593595 | G | A | 183/183 | gene | gene-MEALZ_RS06895 | tssJ |
| NC_016112.1 | 1593598 | A | G | 183/183 | gene | gene-MEALZ_RS06895 | tssJ |
| NC_016112.1 | 1593612 | T | C | 172/172 | gene | gene-MEALZ_RS06895 | tssJ |
| NC_016112.1 | 1593613 | G | A | 172/172 | gene | gene-MEALZ_RS06895 | tssJ |
| NC_016112.1 | 1593633 | A | G | 174/174 | gene | gene-MEALZ_RS06895 | tssJ |
| NC_016112.1 | 1593634 | T | C | 175/175 | gene | gene-MEALZ_RS06895 | tssJ |
| NC_016112.1 | 1593639 | A | T | 176/176 | gene | gene-MEALZ_RS06895 | tssJ |
| NC_016112.1 | 1593641 | A | G | 181/181 | gene | gene-MEALZ_RS06895 | tssJ |
| NC_016112.1 | 1593644 | C | A | 185/185 | gene | gene-MEALZ_RS06895 | tssJ |
| NC_016112.1 | 1593645 | G | A | 184/184 | gene | gene-MEALZ_RS06895 | tssJ |
| NC_016112.1 | 1593652 | C | A | 182/182 | gene | gene-MEALZ_RS06895 | tssJ |
| NC_016112.1 | 1593669 | G | A | 178/178 | gene | gene-MEALZ_RS06895 | tssJ |
| NC_016112.1 | 1593683 | C | T | 179/179 | gene | gene-MEALZ_RS06895 | tssJ |
| NC_016112.1 | 1594017 | A | G | 172/172 | gene | gene-MEALZ_RS06900 | MEALZ_RS06900 |
| NC_016112.1 | 1594020 | G | A | 171/171 | gene | gene-MEALZ_RS06900 | MEALZ_RS06900 |
| NC_016112.1 | 1594023 | A | G | 170/170 | gene | gene-MEALZ_RS06900 | MEALZ_RS06900 |
| NC_016112.1 | 1594053 | G | T | 174/174 | gene | gene-MEALZ_RS06900 | MEALZ_RS06900 |
| NC_016112.1 | 1594054 | T | G | 174/174 | gene | gene-MEALZ_RS06900 | MEALZ_RS06900 |
| NC_016112.1 | 1594125 | C | T | 149/149 | gene | gene-MEALZ_RS06900 | MEALZ_RS06900 |
| NC_016112.1 | 1594206 | C | T | 123/123 | gene | gene-MEALZ_RS06900 | MEALZ_RS06900 |
| NC_016112.1 | 1594314 | C | T | 138/138 | gene | gene-MEALZ_RS06900 | MEALZ_RS06900 |
| NC_016112.1 | 1594377 | C | A | 159/160 | gene | gene-MEALZ_RS06900 | MEALZ_RS06900 |
| NC_016112.1 | 1594425 | C | T | 166/166 | gene | gene-MEALZ_RS06900 | MEALZ_RS06900 |
| NC_016112.1 | 1594428 | C | A | 164/164 | gene | gene-MEALZ_RS06900 | MEALZ_RS06900 |
| NC_016112.1 | 1594434 | G | T | 157/157 | gene | gene-MEALZ_RS06900 | MEALZ_RS06900 |
| NC_016112.1 | 1594479 | T | G | 177/177 | gene | gene-MEALZ_RS06900 | MEALZ_RS06900 |
| NC_016112.1 | 1594518 | C | T | 173/173 | gene | gene-MEALZ_RS06900 | MEALZ_RS06900 |
| NC_016112.1 | 1594520 | T | G | 173/173 | gene | gene-MEALZ_RS06900 | MEALZ_RS06900 |
| NC_016112.1 | 1594524 | A | G | 169/169 | gene | gene-MEALZ_RS06900 | MEALZ_RS06900 |
| NC_016112.1 | 1594549 | T | C | 184/184 | gene | gene-MEALZ_RS06900 | MEALZ_RS06900 |
| NC_016112.1 | 1594575 | C | T | 182/182 | gene | gene-MEALZ_RS06900 | MEALZ_RS06900 |
| NC_016112.1 | 1594578 | G | A | 178/178 | gene | gene-MEALZ_RS06900 | MEALZ_RS06900 |
| NC_016112.1 | 1594602 | T | C | 184/184 | gene | gene-MEALZ_RS06900 | MEALZ_RS06900 |
| NC_016112.1 | 1594612 | C | G | 173/173 | gene | gene-MEALZ_RS06900 | MEALZ_RS06900 |
| NC_016112.1 | 1594656 | C | G | 153/153 | gene | gene-MEALZ_RS06900 | MEALZ_RS06900 |
| NC_016112.1 | 1594662 | C | T | 155/155 | gene | gene-MEALZ_RS06900 | MEALZ_RS06900 |
| NC_016112.1 | 1594683 | A | T | 154/154 | gene | gene-MEALZ_RS06900 | MEALZ_RS06900 |
| NC_016112.1 | 1594701 | G | C | 142/142 | gene | gene-MEALZ_RS06900 | MEALZ_RS06900 |
| NC_016112.1 | 1594704 | A | C | 149/149 | gene | gene-MEALZ_RS06900 | MEALZ_RS06900 |
| NC_016112.1 | 1594710 | T | C | 147/147 | gene | gene-MEALZ_RS06900 | MEALZ_RS06900 |
| NC_016112.1 | 1594713 | C | T | 146/146 | gene | gene-MEALZ_RS06900 | MEALZ_RS06900 |
| NC_016112.1 | 1594728 | A | G | 146/146 | gene | gene-MEALZ_RS06900 | MEALZ_RS06900 |

TABLE 4-continued

Mutations of the host cell that increase RL production.

| #CHROM | POS | REF | ALT | DASS_2_ Genotype | ANNO | GENE_ID | GENE_NAME |
|---|---|---|---|---|---|---|---|
| NC_016112.1 | 1594732 | G | A | 150/150 | gene | gene-MEALZ_RS06900 | MEALZ_RS06900 |
| NC_016112.1 | 1594734 | G | C | 147/147 | gene | gene-MEALZ_RS06900 | MEALZ_RS06900 |
| NC_016112.1 | 1594769 | T | C | 152/152 | gene | gene-MEALZ_RS06900 | MEALZ_RS06900 |
| NC_016112.1 | 1594793 | A | G | 130/130 | gene | gene-MEALZ_RS06900 | MEALZ_RS06900 |
| NC_016112.1 | 1594809 | G | A | 116/116 | gene | gene-MEALZ_RS06900 | MEALZ_RS06900 |
| NC_016112.1 | 1594815 | G | A | 107/107 | gene | gene-MEALZ_RS06900 | MEALZ_RS06900 |
| NC_016112.1 | 1594819 | C | T | 102/102 | gene | gene-MEALZ_RS06900 | MEALZ_RS06900 |
| NC_016112.1 | 1594821 | G | C | 101/101 | gene | gene-MEALZ_RS06900 | MEALZ_RS06900 |
| NC_016112.1 | 1594830 | T | A | 91/91 | gene | gene-MEALZ_RS06900 | MEALZ_RS06900 |
| NC_016112.1 | 1594863 | C | T | 54/54 | Inter-genetic | . | . |
| NC_016112.1 | 1594870 | G | A | 47/47 | Inter-genetic | . | . |
| NC_016112.1 | 1595111 | G | A | 170/170 | Inter-genetic | . | . |
| NC_016112.1 | 1595177 | G | A | 160/160 | Inter-genetic | . | . |
| NC_016112.1 | 1595180 | A | G | 162/162 | Inter-genetic | . | . |
| NC_016112.1 | 1595273 | T | C | 139/139 | gene | gene-MEALZ_RS06905 | MEALZ_RS06905 |
| NC_016112.1 | 1595315 | A | C | 163/163 | gene | gene-MEALZ_RS06905 | MEALZ_RS06905 |
| NC_016112.1 | 1595342 | A | C | 164/164 | gene | gene-MEALZ_RS06905 | MEALZ_RS06905 |
| NC_016112.1 | 1595354 | G | A | 153/153 | gene | gene-MEALZ_RS06905 | MEALZ_RS06905 |
| NC_016112.1 | 1595360 | T | C | 158/158 | gene | gene-MEALZ_RS06905 | MEALZ_RS06905 |
| NC_016112.1 | 1595384 | A | G | 167/167 | gene | gene-MEALZ_RS06905 | MEALZ_RS06905 |
| NC_016112.1 | 1595426 | C | T | 194/194 | gene | gene-MEALZ_RS06905 | MEALZ_RS06905 |
| NC_016112.1 | 1595429 | G | A | 198/198 | gene | gene-MEALZ_RS06905 | MEALZ_RS06905 |
| NC_016112.1 | 1595432 | C | T | 193/193 | gene | gene-MEALZ_RS06905 | MEALZ_RS06905 |
| NC_016112.1 | 1595435 | A | G | 193/193 | gene | gene-MEALZ_RS06905 | MEALZ_RS06905 |
| NC_016112.1 | 1595453 | G | A | 179/179 | gene | gene-MEALZ_RS06905 | MEALZ_RS06905 |
| NC_016112.1 | 1595454 | C | A | 179/179 | gene | gene-MEALZ_RS06905 | MEALZ_RS06905 |
| NC_016112.1 | 1595504 | T | A | 203/203 | gene | gene-MEALZ_RS06905 | MEALZ_RS06905 |
| NC_016112.1 | 1595546 | G | A | 227/227 | gene | gene-MEALZ_RS06905 | MEALZ_RS06905 |
| NC_016112.1 | 1595567 | G | A | 222/222 | gene | gene-MEALZ_RS06905 | MEALZ_RS06905 |
| NC_016112.1 | 1595627 | C | T | 211/211 | gene | gene-MEALZ_RS06905 | MEALZ_RS06905 |
| NC_016112.1 | 1595651 | C | T | 211/211 | gene | gene-MEALZ_RS06905 | MEALZ_RS06905 |
| NC_016112.1 | 1598357 | T | C | 110/111 | gene | gene-MEALZ_RS06915 | folD |
| NC_016112.1 | 1598396 | G | A | 144/144 | gene | gene-MEALZ_RS06915 | folD |
| NC_016112.1 | 1598399 | A | G | 144/144 | gene | gene-MEALZ_RS06915 | folD |
| NC_016112.1 | 1598434 | G | T | 169/169 | gene | gene-MEALZ_RS06915 | folD |
| NC_016112.1 | 1598435 | G | A | 169/169 | gene | gene-MEALZ_RS06915 | folD |
| NC_016112.1 | 1598477 | A | G | 172/172 | gene | gene-MEALZ_RS06915 | folD |
| NC_016112.1 | 1598486 | A | G | 168/168 | gene | gene-MEALZ_RS06915 | folD |
| NC_016112.1 | 1598507 | C | T | 164/164 | gene | gene-MEALZ_RS06915 | folD |
| NC_016112.1 | 1598528 | C | T | 172/172 | gene | gene-MEALZ_RS06915 | folD |
| NC_016112.1 | 1598531 | T | C | 173/173 | gene | gene-MEALZ_RS06915 | folD |
| NC_016112.1 | 1598567 | G | A | 181/181 | gene | gene-MEALZ_RS06915 | folD |
| NC_016112.1 | 1598579 | G | C | 187/187 | gene | gene-MEALZ_RS06915 | folD |
| NC_016112.1 | 1598582 | C | A | 187/187 | gene | gene-MEALZ_RS06915 | folD |
| NC_016112.1 | 1598606 | T | C | 190/190 | gene | gene-MEALZ_RS06915 | folD |
| NC_016112.1 | 1598618 | G | T | 195/195 | gene | gene-MEALZ_RS06915 | folD |
| NC_016112.1 | 1598627 | G | A | 194/194 | gene | gene-MEALZ_RS06915 | folD |
| NC_016112.1 | 1598639 | A | G | 206/206 | gene | gene-MEALZ_RS06915 | folD |
| NC_016112.1 | 1598642 | G | A | 207/207 | gene | gene-MEALZ_RS06915 | folD |
| NC_016112.1 | 1598645 | G | A | 204/204 | gene | gene-MEALZ_RS06915 | folD |
| NC_016112.1 | 1598657 | G | A | 210/210 | gene | gene-MEALZ_RS06915 | folD |
| NC_016112.1 | 1598689 | A | G | 215/215 | gene | gene-MEALZ_RS06915 | folD |
| NC_016112.1 | 1598696 | A | C | 214/214 | gene | gene-MEALZ_RS06915 | folD |
| NC_016112.1 | 1598702 | G | A | 201/201 | gene | gene-MEALZ_RS06915 | folD |
| NC_016112.1 | 1598717 | C | T | 204/204 | gene | gene-MEALZ_RS06915 | folD |
| NC_016112.1 | 1598780 | T | C | 219/219 | gene | gene-MEALZ_RS06915 | folD |
| NC_016112.1 | 1598789 | A | G | 220/220 | gene | gene-MEALZ_RS06915 | folD |
| NC_016112.1 | 1598852 | A | G | 214/214 | gene | gene-MEALZ_RS06915 | folD |
| NC_016112.1 | 1598870 | A | T | 212/212 | gene | gene-MEALZ_RS06915 | folD |
| NC_016112.1 | 1598939 | G | C | 203/203 | gene | gene-MEALZ_RS06915 | folD |
| NC_016112.1 | 1599023 | G | T | 213/213 | gene | gene-MEALZ_RS06915 | folD |
| NC_016112.1 | 1599026 | T | C | 215/215 | gene | gene-MEALZ_RS06915 | folD |
| NC_016112.1 | 1599035 | G | A | 217/217 | gene | gene-MEALZ_RS06915 | folD |
| NC_016112.1 | 1599038 | C | G | 214/214 | gene | gene-MEALZ_RS06915 | folD |
| NC_016112.1 | 1599053 | G | A | 210/211 | gene | gene-MEALZ_RS06915 | folD |
| NC_016112.1 | 1599104 | C | T | 197/197 | gene | gene-MEALZ_RS06915 | folD |
| NC_016112.1 | 1599140 | A | G | 195/195 | inter-genetic | . | . |
| NC_016112.1 | 1599181 | T | C | 182/182 | inter-genetic | . | . |
| NC_016112.1 | 1599182 | T | G | 182/182 | inter-genetic | . | . |
| NC_016112.1 | 1599201 | A | G | 172/172 | inter-genetic | . | . |

TABLE 4-continued

Mutations of the host cell that increase RL production.

| #CHROM | POS | REF | ALT | DASS_2_ Genotype | ANNO | GENE_ID | GENE_NAME |
|---|---|---|---|---|---|---|---|
| NC_016112.1 | 1599206 | C | T | 175/175 | inter-genetic | . | . |
| NC_016112.1 | 1599210 | G | C | 171/171 | inter-genetic | . | . |
| NC_016112.1 | 1599216 | A | C | 179/179 | inter-genetic | . | . |
| NC_016112.1 | 1599217 | T | C | 180/180 | inter-genetic | . | . |
| NC_016112.1 | 1599227 | A | T | 167/167 | inter-genetic | . | . |
| NC_016112.1 | 1815912 | G | C | 58/58 | inter-genetic | . | . |
| NC_016112.1 | 2028111 | C | T | 111/111 | pseudogene | gene-MEALZ_RS08615 | MEALZ_RS08615 |
| NC_016112.1 | 2637141 | T | C | 21/165 | inter-genetic | . | . |
| NC_016112.1 | 2637145 | C | T | 21/164 | inter-genetic | . | . |
| NC_016112.1 | 2637153 | G | A | 21/161 | inter-genetic | . | . |
| NC_016112.1 | 2674948 | A | G | 72/287 | inter-genetic | . | . |
| NC_016112.1 | 2674956 | A | G | 82/292 | inter-genetic | . | . |
| NC_016112.1 | 2674965 | T | G | 89/298 | inter-genetic | . | . |
| NC_016112.1 | 2674967 | A | G | 89/302 | inter-genetic | . | . |
| NC_016112.1 | 2674973 | T | C | 95/309 | inter-genetic | . | . |
| NC_016112.1 | 2675002 | A | G | 127/338 | inter-genetic | . | . |
| NC_016112.1 | 2675003 | T | G | 128/339 | inter-genetic | . | . |
| NC_016112.1 | 2675021 | A | G | 157/374 | inter-genetic | . | . |
| NC_016112.1 | 2675077 | A | G | 157/365 | inter-genetic | . | . |
| NC_016112.1 | 2675094 | G | A | 136/352 | inter-genetic | . | . |
| NC_016112.1 | 2703406 | C | G | 5/6 | gene | gene-MEALZ_RS11580 | MEALZ_RS11580 |
| NC_016112.1 | 2703409 | A | G | 3/4 | gene | gene-MEALZ_RS11580 | MEALZ_RS11580 |
| NC_016112.1 | 3190412 | T | C | 117/224 | inter-genetic | . | . |
| NC_016112.1 | 3190432 | G | A | 84/185 | inter-genetic | . | . |
| NC_016112.1 | 3190464 | T | C | 43/147 | inter-genetic | . | . |
| NC_016112.1 | 3797919 | C | T | 167/315 | gene | gene-MEALZ_RS16020 | MEALZ_RS16020 |
| NC_016112.1 | 3798246 | T | C | 188/377 | gene | gene-MEALZ_RS16020 | MEALZ_RS16020 |
| NC_016112.1 | 3798385 | A | G | 182/392 | gene | gene-MEALZ_RS16020 | MEALZ_RS16020 |
| NC_016112.1 | 3798455 | C | G | 196/420 | gene | gene-MEALZ_RS16020 | MEALZ_RS16020 |
| NC_016112.1 | 3798478 | A | C | 207/438 | gene | gene-MEALZ_RS16020 | MEALZ_RS16020 |
| NC_016112.1 | 3798479 | T | C | 204/435 | gene | gene-MEALZ_RS16020 | MEALZ_RS16020 |
| NC_016112.1 | 3798503 | T | C | 218/456 | gene | gene-MEALZ_RS16020 | MEALZ_RS16020 |
| NC_016112.1 | 4222340 | T | G | 15/40 | gene | gene-MEALZ_RS17920 | MEALZ_RS17920 |
| NC_016112.1 | 4222349 | A | C | 22/48 | gene | gene-MEALZ_RS17920 | MEALZ_RS17920 |
| NC_016112.1 | 4233436 | G | T | 194/194 | gene | gene-MEALZ_RS17985 | MEALZ_RS17985 |
| NC_016112.1 | 4233466 | G | A | 197/197 | gene | gene-MEALZ_RS17985 | MEALZ_RS17985 |
| NC_016112.1 | 4233475 | A | G | 196/196 | gene | gene-MEALZ_RS17985 | MEALZ_RS17985 |
| NC_016112.1 | 4233780 | C | T | 199/199 | gene | gene-MEALZ_RS17985 | MEALZ_RS17985 |
| NC_016112.1 | 4233854 | T | C | 218/218 | gene | gene-MEALZ_RS17985 | MEALZ_RS17985 |
| NC_016112.1 | 4239364 | A | G | 30/30 | inter-genetic | . | . |
| NC_016112.1 | 4239375 | T | G | 39/39 | inter-genetic | . | . |
| NC_016112.1 | 4239378 | A | G | 40/40 | inter-genetic | . | . |
| NC_016112.1 | 4249077 | T | C | 179/179 | inter-genetic | . | . |
| NC_016112.1 | 4249101 | A | T | 179/179 | gene | gene-MEALZ_RS18045 | MEALZ_RS18045 |
| NC_016112.1 | 4249149 | T | C | 175/175 | gene | gene-MEALZ_RS18045 | MEALZ_RS18045 |
| NC_016112.1 | 4249152 | A | G | 176/176 | gene | gene-MEALZ_RS18045 | MEALZ_RS18045 |
| NC_016112.1 | 4249185 | A | G | 177/177 | gene | gene-MEALZ_RS18045 | MEALZ_RS18045 |
| NC_016112.1 | 4249212 | C | T | 181/183 | gene | gene-MEALZ_RS18045 | MEALZ_RS18045 |
| NC_016112.1 | 4249287 | A | T | 185/185 | gene | gene-MEALZ_RS18045 | MEALZ_RS18045 |
| NC_016112.1 | 4249322 | C | T | 182/182 | gene | gene-MEALZ_RS18045 | MEALZ_RS18045 |
| NC_016112.1 | 4249335 | A | G | 173/173 | gene | gene-MEALZ_RS18045 | MEALZ_RS18045 |
| NC_016112.1 | 4249392 | G | A | 167/167 | gene | gene-MEALZ_RS18045 | MEALZ_RS18045 |
| NC_016112.1 | 4249608 | T | C | 139/139 | gene | gene-MEALZ_RS18045 | MEALZ_RS18045 |
| NC_016112.1 | 4249620 | G | T | 142/142 | gene | gene-MEALZ_RS18045 | MEALZ_RS18045 |
| NC_016112.1 | 4249623 | T | C | 142/142 | gene | gene-MEALZ_RS18045 | MEALZ_RS18045 |
| NC_016112.1 | 4249634 | A | G | 148/148 | gene | gene-MEALZ_RS18045 | MEALZ_RS18045 |
| NC_016112.1 | 4249635 | A | G | 148/148 | gene | gene-MEALZ_RS18045 | MEALZ_RS18045 |
| NC_016112.1 | 4249670 | A | G | 151/151 | gene | gene-MEALZ_RS18045 | MEALZ_RS18045 |
| NC_016112.1 | 4249692 | C | T | 166/166 | gene | gene-MEALZ_RS18045 | MEALZ_RS18045 |
| NC_016112.1 | 4249695 | C | T | 166/166 | gene | gene-MEALZ_RS18045 | MEALZ_RS18045 |
| NC_016112.1 | 4249717 | C | T | 164/164 | gene | gene-MEALZ_RS18045 | MEALZ_RS18045 |
| NC_016112.1 | 4249809 | T | C | 162/162 | gene | gene-MEALZ_RS18045 | MEALZ_RS18045 |
| NC_016112.1 | 4249824 | G | A | 157/157 | gene | gene-MEALZ_RS18045 | MEALZ_RS18045 |
| NC_016112.1 | 4249842 | T | C | 157/157 | gene | gene-MEALZ_RS18045 | MEALZ_RS18045 |
| NC_016112.1 | 4249845 | C | G | 160/160 | gene | gene-MEALZ_RS18045 | MEALZ_RS18045 |
| NC_016112.1 | 4249860 | T | C | 149/149 | gene | gene-MEALZ_RS18045 | MEALZ_RS18045 |
| NC_016112.1 | 4249874 | T | C | 143/143 | gene | gene-MEALZ_RS18045 | MEALZ_RS18045 |
| NC_016112.1 | 4249883 | A | G | 150/150 | gene | gene-MEALZ_RS18045 | MEALZ_RS18045 |
| NC_016112.1 | 4249893 | C | T | 146/146 | gene | gene-MEALZ_RS18045 | MEALZ_RS18045 |
| NC_016112.1 | 4249902 | T | C | 142/142 | gene | gene-MEALZ_RS18045 | MEALZ_RS18045 |
| NC_016112.1 | 4249908 | A | G | 140/140 | gene | gene-MEALZ_RS18045 | MEALZ_RS18045 |
| NC_016112.1 | 4249911 | A | G | 136/136 | gene | gene-MEALZ_RS18045 | MEALZ_RS18045 |
| NC_016112.1 | 4249912 | A | C | 137/137 | gene | gene-MEALZ_RS18045 | MEALZ_RS18045 |
| NC_016112.1 | 4249914 | C | T | 138/138 | gene | gene-MEALZ_RS18045 | MEALZ_RS18045 |
| NC_016112.1 | 4249917 | A | G | 137/137 | gene | gene-MEALZ_RS18045 | MEALZ_RS18045 |

TABLE 4-continued

Mutations of the host cell that increase RL production.

| #CHROM | POS | REF | ALT | DASS_2_ Genotype | ANNO | GENE_ID | GENE_NAME |
|---|---|---|---|---|---|---|---|
| NC_016112.1 | 4249926 | T | C | 130/130 | gene | gene-MEALZ_RS18045 | MEALZ_RS18045 |
| NC_016112.1 | 4249986 | A | G | 127/127 | gene | gene-MEALZ_RS18045 | MEALZ_RS18045 |
| NC_016112.1 | 4250010 | T | C | 125/125 | gene | gene-MEALZ_RS18045 | MEALZ_RS18045 |
| NC_016112.1 | 4250103 | G | A | 129/129 | gene | gene-MEALZ_RS18045 | MEALZ_RS18045 |
| NC_016112.1 | 4250110 | A | C | 133/133 | gene | gene-MEALZ_RS18045 | MEALZ_RS18045 |
| NC_016112.1 | 4250113 | C | T | 134/134 | gene | gene-MEALZ_RS18045 | MEALZ_RS18045 |
| NC_016112.1 | 4250115 | T | C | 140/140 | gene | gene-MEALZ_RS18045 | MEALZ_RS18045 |
| NC_016112.1 | 4250119 | T | A | 143/143 | gene | gene-MEALZ_RS18045 | MEALZ_RS18045 |
| NC_016112.1 | 4250142 | A | G | 160/160 | gene | gene-MEALZ_RS18045 | MEALZ_RS18045 |
| NC_016112.1 | 4250148 | T | C | 164/164 | gene | gene-MEALZ_RS18045 | MEALZ_RS18045 |
| NC_016112.1 | 4250154 | G | A | 157/157 | gene | gene-MEALZ_RS18045 | MEALZ_RS18045 |
| NC_016112.1 | 4250157 | G | A | 156/156 | gene | gene-MEALZ_RS18045 | MEALZ_RS18045 |
| NC_016112.1 | 4250166 | C | T | 157/157 | gene | gene-MEALZ_RS18045 | MEALZ_RS18045 |
| NC_016112.1 | 4250169 | C | T | 161/161 | gene | gene-MEALZ_RS18045 | MEALZ_RS18045 |
| NC_016112.1 | 4250172 | G | A | 157/157 | gene | gene-MEALZ_RS18045 | MEALZ_RS18045 |
| NC_016112.1 | 4250199 | T | C | 167/167 | gene | gene-MEALZ_RS18045 | MEALZ_RS18045 |
| NC_016112.1 | 4250200 | T | G | 168/168 | gene | gene-MEALZ_RS18045 | MEALZ_RS18045 |
| NC_016112.1 | 4250205 | T | C | 166/166 | gene | gene-MEALZ_RS18045 | MEALZ_RS18045 |
| NC_016112.1 | 4250235 | G | A | 181/181 | gene | gene-MEALZ_RS18045 | MEALZ_RS18045 |
| NC_016112.1 | 4250253 | T | G | 171/171 | gene | gene-MEALZ_RS18045 | MEALZ_RS18045 |
| NC_016112.1 | 4250319 | G | A | 161/161 | gene | gene-MEALZ_RS18045 | MEALZ_RS18045 |
| NC_016112.1 | 4250546 | G | A | 178/178 | inter-genetic | . | . |
| NC_016112.1 | 4250584 | T | C | 192/192 | inter-genetic | . | . |
| NC_016112.1 | 4250678 | C | T | 218/218 | inter-genetic | . | . |
| NC_016112.1 | 4250712 | A | T | 240/240 | inter-genetic | . | . |
| NC_016112.1 | 4250808 | A | G | 227/227 | inter-genetic | . | . |
| NC_016112.1 | 4250821 | C | T | 218/218 | inter-genetic | . | . |
| NC_016112.1 | 4250837 | G | C | 217/217 | inter-genetic | . | . |
| NC_016112.1 | 4250863 | T | A | 180/180 | inter-genetic | . | . |
| NC_016112.1 | 4250879 | A | G | 177/177 | inter-genetic | . | . |
| NC_016112.1 | 4250924 | A | G | 157/157 | inter-genetic | . | . |
| NC_016112.1 | 4255137 | C | T | 187/189 | gene | gene-MEALZ_RS18060 | MEALZ_RS18060 |
| NC_016112.1 | 4255200 | C | T | 202/202 | gene | gene-MEALZ_RS18060 | MEALZ_RS18060 |
| NC_016112.1 | 4258918 | T | A | 197/197 | gene | gene-MEALZ_RS18075 | MEALZ_RS18075 |
| NC_016112.1 | 4258932 | A | G | 200/200 | gene | gene-MEALZ_RS18075 | MEALZ_RS18075 |
| NC_016112.1 | 4258938 | G | A | 208/208 | gene | gene-MEALZ_RS18075 | MEALZ_RS18075 |
| NC_016112.1 | 4258963 | A | T | 232/232 | gene | gene-MEALZ_RS18075 | MEALZ_RS18075 |
| NC_016112.1 | 4258972 | C | T | 231/231 | gene | gene-MEALZ_RS18075 | MEALZ_RS18075 |
| NC_016112.1 | 4259013 | A | G | 238/238 | gene | gene-MEALZ_RS18075 | MEALZ_RS18075 |
| NC_016112.1 | 4259401 | C | T | 210/210 | gene | gene-MEALZ_RS18075 | MEALZ_RS18075 |
| NC_016112.1 | 4259421 | T | C | 214/214 | gene | gene-MEALZ_RS18075 | MEALZ_RS18075 |
| NC_016112.1 | 4259727 | T | C | 185/185 | gene | gene-MEALZ_RS18075 | MEALZ_RS18075 |
| NC_016112.1 | 4262921 | A | G | 173/173 | gene | gene-MEALZ_RS18090 | MEALZ_RS18090 |
| NC_016112.1 | 4262948 | A | G | 167/167 | gene | gene-MEALZ_RS18090 | MEALZ_RS18090 |
| NC_016112.1 | 4263098 | C | T | 230/231 | gene | gene-MEALZ_RS18090 | MEALZ_RS18090 |
| NC_016112.1 | 4263149 | G | T | 223/223 | gene | gene-MEALZ_RS18090 | MEALZ_RS18090 |
| NC_016112.1 | 4263405 | T | G | 186/186 | gene | gene-MEALZ_RS18090 | MEALZ_RS18090 |
| NC_016112.1 | 4263776 | T | A | 241/241 | gene | gene-MEALZ_RS18090 | MEALZ_RS18090 |
| NC_016112.1 | 4263947 | C | G | 218/218 | inter-genetic | . | . |
| NC_016112.1 | 4263958 | T | C | 225/225 | inter-genetic | . | . |
| NC_016112.1 | 4263968 | C | T | 231/231 | inter-genetic | . | . |
| NC_016112.1 | 4263979 | A | G | 228/228 | inter-genetic | . | . |
| NC_016112.1 | 4270962 | C | T | 119/392 | gene | gene-MEALZ_RS18120 | MEALZ_RS18120 |
| NC_016112.1 | 4270965 | A | G | 119/392 | gene | gene-MEALZ_RS18120 | MEALZ_RS18120 |
| NC_016112.1 | 4270968 | T | C | 119/398 | gene | gene-MEALZ_RS18120 | MEALZ_RS18120 |
| NC_016112.1 | 4271667 | C | A | 44/195 | gene | gene-MEALZ_RS18120 | MEALZ_RS18120 |
| NC_016112.1 | 4271679 | C | G | 19/142 | gene | gene-MEALZ_RS18120 | MEALZ_RS18120 |
| NC_016112.1 | 4271701 | T | A | 59/60 | gene | gene-MEALZ_RS18120 | MEALZ_RS18120 |
| NC_016112.1 | 4428308 | G | C | 4/5 | gene | gene-MEALZ_RS18840 | MEALZ_RS18840 |
| NC_016112.1 | 4552963 | T | C | 219/463 | gene | gene-MEALZ_RS19385 | tkt |
| NC_016112.1 | 4553104 | G | A | 236/451 | gene | gene-MEALZ_RS19385 | tkt |
| NC_016112.1 | 4553506 | C | T | 169/344 | gene | gene-MEALZ_RS19385 | tkt |
| NC_016112.1 | 4553743 | A | G | 192/398 | gene | gene-MEALZ_RS19385 | tkt |
| NC_016112.1 | 4554354 | T | C | 187/412 | gene | gene-MEALZ_RS19385 | tkt |
| NC_016108.1 | 128058 | G | C | 36/36 | gene | gene-MEALZ_RS21105 | MEALZ_RS21105 |

In some embodiments, the host cell or methanotroph is not a natural rhamnolipid producer. In some embodiments, the host cell or methanotroph in its unmodified form is sensitive, or unable to grow, in a medium having rhamnolipid at a concentration equal to or more than about 0.05 g/L, 0.06 g/L, 0.07 g/L, 0.08 g/L, 0.09 g/L, 0.1 g/L, 0.2 g/L, 0.3 g/L, 0.4 g/L, 0.5 g/L, 0.6 g/L, 0.7 g/L, 0.8 g/L, 0.9 g/L, 1.0 g/L, or 1.5 g/L, or within a range of any two preceding values. In some embodiments, the host cell or methanotroph when modified is resistant, or able to grow, in a medium having rhamnolipid at a concentration equal to or less than about 1.0 g/L, 1.5 g/L, 2.0 g/L, 2.5 g/L, 3.0 g/L, 3.5 g/L, 4.0 g/L, 4.5 g/L, or 5.0 g/L, or within a range of any two preceding values. In some embodiments, the host cell or methanotroph when modified is capable of producing more rhamnolipid and/or fatty acids than the host cell or methanotroph in its unmodified form. In some embodiments, the methanotroph can produce more rhamnolipid and/or fatty acids using methane as the sole carbon source.

Other objects, features, and advantages of the present invention will be apparent to one of skill in the art from the following detailed description and figures.

BRIEF DESCRIPTION OF THE DRAWINGS

The foregoing aspects and others will be readily appreciated by the skilled artisan from the following description of illustrative embodiments when read in conjunction with the accompanying drawings.

FIG. 3. Schematic of differential expression of peptides and metabolites of ribulose monophosphate (RuMP), Embden-Meyerhof-Parnas (EMP), and Entner-Doudoroff (ED) Pathway in *M. alcaliphilum* WT and DASS strains at 24 h of growth on methane. Pathway arrows represent fold change ratio of average NSAF (normalized spectral abundance factor) values of two independent experiments of DASS over WT strain [$(NSAF_{DASS}-NSAF_{WT})/NSAF_{WT}$]. The fold change ratio is the ratio of change in final ($NSAF_{DASS}$) and original ($NSAF_{WT}$) value over original value, where a fold change ratio of 1 would mean a change by two times of original value, and a fold change ratio of −0.5 will correspond to final value being half of original value. Graphs depict absolute concentration of metabolite quantified in μM (Y-axis) from three independent experiments. AccA, acetyl-CoA carboxylase; AcnB, aconitate hydratase; Eda, aldolase; Edd, dehydratase; Eno, enolase; FbaA, fructose-bisphosphate aldolase, class II; Fdh1A&1B, NAD-dependent formate dehydrogenase, alpha and beta subunit; FumC, fumarate dehydrogenase; GltA, citrate synthase; Gpi, phosphoglucose isomerase; Hps1, 3-hexulose-6-phosphate synthase; Hpi1/Phi, 3-hexulose-6-phosphate isomerase; Icd, isocitrate dehydrogenase; MtkB, succinate-CoA synthetase; MxaF, methanol dehydrogenase; PdhA, pyruvate dehydrogenase E1 component; Pgk, phosphoglycerate kinase; Pgm3, phosphoglycerate mutase; PmoA,B &C, particulate methane monooxygenase, subunit A, B and C; PykA, pyruvate kinase; Mdh, malate dehydrogenase; Sdh, succinate dehydrogenase; SucB, α-ketoglutarate dehydrogenase; Zwf, glucose dehydrogenase. F-1,6-P, fructose-1,6-bisphosphate; F6P, Fructose-6-phospahte, GAP, glyceraldehyde-3-phosphate; G6P, glucose-6-phosphate; H6P, hexulose-6-phosphate; KDPG, 2-dehydro-3-deoxyphosphogluconate aldolase; PEP, phosphoenolpyruvate; 6PG, 6-phosphogluconate; Ru5P, ribulose-5-phosphate. Green, intracellular concentration (μM); Orange, extracellular concentration (μM); UD, undetected.

FIG. 9. Heat map representing the fold change of peptides detected (NSAF, normalized spectral abundance factor) in strain DASS compared to WT at 48 h of growth. UC, hypothetical and/or uncharacterized proteins; UC (transmembrane), uncharacterized protein with transmembrane signal peptide domain. Yellow to Green-significant upregulated (p≤0.05 and 3.7≥FC≥0.32); Orange to Red-significant downregulated (p≤0.05 and −0.32≥FC≥−2.8).

DETAILED DESCRIPTION OF THE INVENTION

Figure 1:
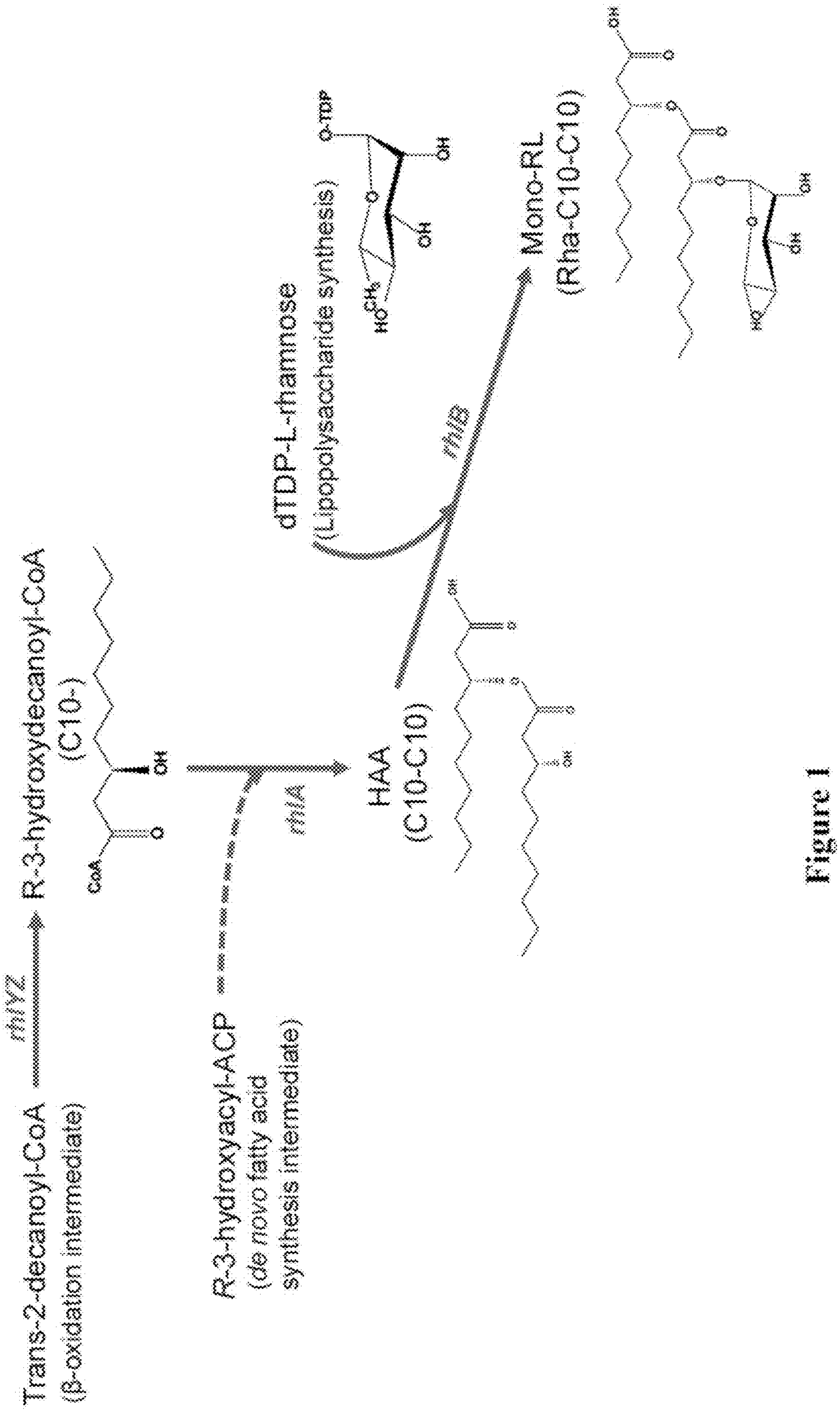
FIG. 1. Schematic of rhamnolipid biosynthesis pathway in *Pseudomonas aeruginosa*. HAA, hydroxyakanoyloxyalkanoic acid; rhlA, 3-hydroxyacyl-ACP-O-3 hydroxyacyltransferase; rhlB, rhamnosyl transferase; rhlYZ, enoyl-CoA hydratase/isomerase.

Before the invention is described in detail, it is to be understood that, unless otherwise indicated, this invention is not limited to particular sequences, expression vectors, enzymes, host cells, microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "about" as used herein means a value that includes 10% less and 10% more than the value referred to.

The terms "host cell" and "host microorganism" are used interchangeably herein to refer to a living biological cell, such as a microorganism, that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. The term "heterologous" as used herein refers to a structure or molecule wherein at least one of the following is true: (a) the structure or molecule is foreign to (i.e., not naturally found in) a given host cell; or (b) the structure or molecule may be naturally found in a given host cell, but in an unnatural (e.g., greater than expected) amount. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host cell, wherein the expression vector contains a nucleic acid sequence coding for an enzyme that is not normally found in a host cell. With reference to the host cell's genome, then, the nucleic acid sequence that codes for the enzyme is heterologous.

The terms "expression vector" or "vector" refer to a compound and/or composition that transduces, transforms, or infects a host cell, thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host cell or cell. Only when the sequence of nucleic acids becomes stably replicated by the cell does the host cell or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host cell, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

In some embodiments, the methanotroph is an obligate methane consumer, *Methylomicrobium alcaliphilum* strain DSM19304 into a recombinant rhamnolipid producer. The parent *M. alcaliphilum* DSM19304 cannot withstand higher levels of rhamnolipids (MIC 0.5 g/L). So, to alleviate product toxicity, *M. alcaliphilum* DSM19304 is evolved over a period of about 4 months. The evolved strain *M. alcaliphilum* DASS can tolerate up to about 4 g/L rhamnolipids. In some embodiments, the methanotroph can tolerate up to about 1, 2, 3, or 4 g/L rhamnolipids. In some embodiments, the methanotroph is the strain DASS described herein. In some embodiments, the methanotroph is engineered by introducing a rhlYZAB rhamnolipid cassette of *P. aeruginosa* on a plasmid based system.

In some embodiments, the host cell engineered by introducing a rhlYZAB produces a higher titer of fatty acids than a modified host cell, and/or about 1, 2, 3, 4, 5, 6, 7, 8, 9, or 10 mg/L of mono-rhamnolipids. In some embodiments, the host cell is an engineered *M. alcaliphilum* strain that produces a higher titer of fatty acids than a parent *M. alcaliphilum* strain DSM19304, which is a GRAS characterized strain for industrial purposes as compared to *P. aeruginosa* (native producer). In some embodiments, the host cell is capable of growing at a pH equal to or more than about 9.0, and/or in a medium with equal to or more than about 3M NaCl. *M. alcaliphilum* strains are known for their halo-alkaline nature, wherein they can grow at a pH >9.0 and 3M NaCl in a chemically defined mineral salts media. Rhamnolipid production from low cost methane, low cost media and no added carbon or nitrogen supplementation makes the overall process cost-effective over existing industrial bioprocesses.

Rhamnolipids (RLs) are detergent/emulsifiers and can be toxic to other microbes. This glycolipid is natively produced by virulent strains of *P. aeruginosa* at high titer. Recombinant production of rhamnolipids by expression of rhlYZAB gene cassette of *P. aeruginosa* in other host platforms has not been commercially successful due to costly substrate supplementation, media composition and titer limitations making the process and targeted product costly. This gap requires us to think of an alternate and comparatively low-cost substrate and a platform host that can be engineered to produce this product, rhamnolipid. Methanotroph *Methylomicrobium alcahphilum* (obligate methane assimilating gram-negative bacteria) is an interesting microbial host to pursue recombinant RL synthesis. *M. alcaliphilum* strain DSM19304 is not a natural rhamnolipid producer and it cannot tolerate rhamnolipids surfactant effects at concentrations as low as 0.5 g/L. The present invention comprises or is one or more of the following: (a) a *M. alcaliphilum* strain that adapted to grow and tolerate 4 g/L rhamnolipids. (b) The strain (DASS) produces comparatively higher amount of free fatty acids than the native strain DSM19304. Secretion of free fatty acids has been of biotechnological relevance in many recent studies, since the free fatty acids can be chemically processed into many other products, for example, lubricants, surfactants, polymer additives, or the like. (c) Expression of codon optimized rhamnolipid pathway harboring plasmid (pDA21) in the wild type (WT) and adapted (DASS) strain had a very distinct characteristic. The *M. alcahphilum* WT strain that harbored the rhamnolipid expression plasmid (pDA21) showed very poor and slow growth, as expected from the low MIC of rhamnolipid on WT strain. In contrast, the adapted strain produces about 10 mg/L rhamnolipids from methane as the sole carbon source.

Enzymes, and Nucleic Acids Encoding Thereof

A homologous enzyme is an enzyme that has a polypeptide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof.

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) Tet. Lett. 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host cell simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the LacI repressor protein from binding to the operator). Another example is the tac promoter. (See deBoer et al. (1983) Proc. Natl. Acad. Sci. USA, 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host cell. Also, microinjection of the nucleic acid sequencers) provides the ability to transfect host cell. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

In some embodiments, the host cells are genetically modified in that heterologous nucleic acid have been introduced into the host cells, and as such the genetically modified host cells do not occur in nature. The suitable host cell is one capable of expressing a nucleic acid construct encoding one or more enzymes described herein. The gene(s) encoding the enzyme(s) may be heterologous to the host cell or the gene may be native to the host cell but is operatively linked to a heterologous promoter and one or more control regions which result in a higher expression of the gene in the host cell.

The enzyme can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

References cited herein:

1 Surfactants Market Size, Share & Trends Analysis Report By Product, By Application, By Region (North America, Europe, Asia Pacific, RoW), And Segment Forecasts, 2016-2022. Report No. 978-1-68038-592-2, 90 (California, 2015).

2 Chong, H. & Li, Q. Microbial production of rhamnolipids: opportunities, challenges and strategies. *Microb Cell Fact* 16, 137, doi:10.1186/s12934-017-0753-2 (2017).

3 Muller, M. M. et al. Rhamnolipids—next generation surfactants?*J Biotechnol* 162, 366-380, (2012).

4 Sekhon Randhawa, K. K. & Rahman, P. K. Rhamnolipid biosurfactants-past, present, and future scenario of global market. *Front Microbiol* 5, 454, (2014).

5 Sobero'n-Cha'vez, G. a. S. c., A. Biosurfactant: from Genes to Applications. *Springer*, (2011).

6 Thakur, P. et al. Rhamnolipid the Glycolipid Biosurfactant: Emerging trends and promising strategies in the field of biotechnology and biomedicine. *Microb Cell Fact* 20, 1, (2021).

7 Hauser, G., and M. L. Karnovsky. Rhamnose and rhamnolipid biosynthesis by *Pseudomonas aeruginosa*. *J. Biol. Chem* 224, 91-105 (1957).

8 Jarvis, F. G., and M. J. Johnson. A glycolipid produced by *Pseudomonas aeruginosa*. *J. Am. Chem. Soc.* 71, 4124-4126 (1949).

9 Burger, M. M., L. Glaser, and R. M. Burton. The enzymatic synthesis of a rhamnose-containing glycolipid by extracts of *Pseudomonas aeruginosa*. *J. Biol. Chem* 238, 2595-2602 (1963).

10 Lequette, Y. & Greenberg, E. P. Timing and localization of rhamnolipid synthesis gene expression in *Pseudomonas aeruginosa* biofilms. *J Bacteriol* 187, 37-44, (2005).

11 Abdel-Mawgoud, A. M., Lepine, F. & Deziel, E. A stereospecific pathway diverts beta-oxidation intermediates to the biosynthesis of rhamnolipid biosurfactants. *Chem Biol* 21, 156-164, (2014).

12 Naismith, M.-F. G. a. J. H. The Rhamnose Pathway *Current Opinion in Structural Biology* 10, 687-696 (2000).

13 Bazire, A. a. D., A. The *Pseudomonas aeruginosa* rhlG and rhlAB genes are inversely regulated and RhlG is not required for rhamnolipid synthesis. *BMC Microbiology* 14, 160-169 (2014).

14 Abdel-Mawgoud, A. M., Lepine, F. & Deziel, E. Rhamnolipids: diversity of structures, microbial origins and roles. *Appl Microbiol Biotechnol* 86, 1323-1336, (2010).

15 Trummler, K., Effenberger, F., Syldatk, C. An integrated microbial/enzymatic process for production of rhamnolipids and 1-(+)-rhamnose from rapeseed oil with *Pseudomonas* sp. DSM 2874. *European Journal of Lipid Science and Technology* 105, 563-571 (2003).

16 Wei, Y.-H., Chou, C.-L., Chang, J.-S. Rhamnolipid production by indigenous *Pseudomonas aeruginosa* J4 originating from petroChem. *Wastewater Biochemical Engineering Journal* 27, 146 (2005).

17 Lovaglio, R. B., Costa, S., Lima, C.J.B., Cortezi, M., Jonas, C. Effect of C/N ratio and physicoChem. conditions on the production of rhamnolipids by *Pseudomonas aeruginosa* LBI. *Research Journal of Biotechnology,* 19-24 (2010).

18 Irorere, V. U., Tripathi, L., Marchant, R., McClean, S. & Banat, I. M. Microbial rhamnolipid production: a critical re-evaluation of published data and suggested future publication criteria. *Appl Microbiol Biotechnol* 101, 3941-3951, (2017).

19 Dubeau, D., Deziel, E., Woods, D.E., Lepine, F. *Burkholderia thailandensis* harbors two identical rhl gene clusters responsible for the biosynthesis of rhamnolipids. *BMC Microbiology* 9, 263 (2009).

20 Costa S, D. E., Lepine F. Characterization of rhamnolipid production by *Burkholderia glumae. Lett Appl Microbiol* 53, 620-627 (2011).

21 Hörmann, B., Müller, M.M., Syldatk, C., Hausmann, R. Rhamnolipid production by *Burkholderia plantarii* DSM9509T. *European Journal of Lipid Science and Technology* 112, 674-680 (2010).

22 Beuker J, B. T., Steier A, Wittgens A, Rosenau F, Henkel M, Hausmann R. High titer heterologous rhamnolipid production. *AMB Express.* 6, 124 (2016).

23 Wittgens A, T. T., Arndt TT, Wenk P, Hemmerich J, Muller C, Wichmann R, Kupper B, Zwick M, Wilhelm S. Growth independent rhamnolipid production from glucose using the non-pathogenic *Pseudomonas putida* KT2440. *Microb Cell Fact* 10, 80 (2011).

24 Lotfabad TB, E. N., RoostaAzad R. Evaluation of a recycling bioreactor for biosurfactant production by *Pseudomonas aeruginosa* MR01 using soybean oil waste. *J Chem Technol Biotechnol* 91, 1368-1377 (2016).

25 Schaefer, S. E. M. F. a. H. Rising methane: A new climate challenge. *Science* 364 932-933, (2019).

26 Wuebbles, D. J. a. H., K. Atmospheric methane and global change. *Earth-Science* 57, 177-210 (2002).

27 Rahman, A. a. G., J.M. Methane as Subsatrate for biomanufacturing. 48*th International Conference on Environmental Systems,* 1-10 (2018).

28 Administration, U. S. E. I. United States remains the world's top producer of petroleum and natural gas hydrocarbons - Today in Energy (May 2018).

29 Jin, G., Bierma, T. & Walker, P. Biogas production from switchgrass under experimental conditions simulating U.S. digester operations. *J Environ Sci Health A Tox Hazard Subst Environ Eng* 47, 470-478, (2012).

30 Shen, Y., Linville, J. L., Urgun-Demirtas, M., Mintz, M. M. & Snyder, S. W. An overview of biogas production and utilization at full-scale wastewater treatment plants (WWTPs) in the United States: Challenges and opportunities towards energy-neutral WWTPs. *Renewable and Sustainable Energy Reviews* 50, 346-362, (2015).

31 Chistoserdova, L., Kalyuzhnaya, M. G. & Lidstrom, M. E. The expanding world of methylotrophic metabolism. *Annu Rev Microbiol* 63, 477-499, (2009).

32 Kalyuzhnaya, M. G. a. X., X.H. Methane Biocatalysis: Paving the way to sustainibility. *Springer* (2018).

33 Henard, C. A. et al. Bioconversion of methane to lactate by an obligate methanotrophic bacterium. *Sci Rep* 6, 21585, doi:10.1038/srep21585 (2016).

34 Henard, C. A., Smith, H. K. & Guarnieri, M. T. Phosphoketolase overexpression increases biomass and lipid yield from methane in an obligate methanotrophic biocatalyst. *Metab Eng* 41, 152-158, (2017).

35 J. M. Clomburg, A. M. C. a. R. G. Industrial biomanufacturing: The future of chemical production. *Science* 355 (2017).

36 Calvin A. Henard, I. R. A., Marina G. Kalyuzhnaya and Michael T. Guarnieri. Muconic acid production from methane using rationally-engineered methanotrophic biocatalysts. *Green Chemistry* 21, 6731-6737, (2019).

37 Rozova, O. N., Khmelenina, V. N., Vuilleumier, S. & Trotsenko, Y. A. Characterization of recombinant pyrophosphate-dependent 6-phosphofructokinase from halotolerant methanotroph *Methylomicrobium alcaliphilum* 20Z. *Res Microbiol* 161, 861-868, (2010).

38 Akberdin, I. R. et al. Methane utilization in Methylomicrobium alcaliphilum 20Z(R): a systems approach. *Sci Rep* 8, 2512, (2018).

39 Ojala, D. S., Beck, D.A.C. and Kalyuzhnaya, M.G. . Genetic systems for moderatly halo (alkali) philic bacteria of the genus Methylomicrobium. *Methods in Enzymology* 495, Chapter 7, 99-118, (2011).

40 Kalyuzhnaya, M. G. et al. Highly efficient methane biocatalysis revealed in a methanotrophic bacterium. *Nat Commun* 4, 2785, (2013).

41 Kalyuzhnaya, M. G., Puri, A. W. & Lidstrom, M. E. Metabolic engineering in methanotrophic bacteria. *Metab Eng* 29, 142-152, (2015).

42 de Carvalho, C. & Caramujo, M. J. The Various Roles of Fatty Acids. *Molecules* 23, (2018).

43 Jones, M. N. Surfactants in membrane solubilisation. *International Journal of Pharmaceutics* 177, 137-159 (1999).

44 John P. Bowman, J. H. S., Peter D. Nichols and Lindsay I. Sly. Phospholipid fatty acid and lipopolysaccharide fatty acid signature lipids in methane-utilizing bacteria. *FEMS Microbiology Ecology* 85 15-22 (1991).

45 Costello, A. M., Auman, A.J., Macalady, J.L., Scow, K.M., and & Mary E. Lidstrom, M. E. Estimation of methanotroph abundance in lake. *Environmental Microbiology* 4, 443-450 (2002).

46 Parsons, J. B. & Rock, C. O. Bacterial lipids: metabolism and membrane homeostasis. *Prog Lipid Res* 52, 249-276, (2013).

47 Pfleger, R. M. L. a. B. F. Microbial production of fatty acid-derived fuels and chemicals. *Current Opinion in Biotechnology* 24, 1044-1053 (2013).

48 Lorra K. Fuhrman , A. W., Kenneth W. Nickerson and Tyrrell Conway Rapid accumulation of intracellular 2-keto-3-deoxy-6-phosphogluconate in an Entner-Doudoroff aldolase mutant results in bacteriostasis. *FEMIS Microbiology Letters* 159, 261-266 (1998).

49 But, S. Y. et al. Sucrose metabolism in halotolerant methanotroph *Methylomicrobium alcaliphilum* 20Z. *Arch Microbiol* 197, 471-480, (2015).

50 Mustakhimov, II et al. Identification and characterization of EctR1, a new transcriptional regulator of the ectoine biosynthesis genes in the halotolerant methanotroph *Methylomicrobium alcaliphilum* 20Z. *J Bacteriol* 192, 410-417, doi:10.1128/JB.00553-09 (2010).

51 Demidenko, A., Akberdin, I. R., Allemann, M., Allen, E. E. & Kalyuzhnaya, M. G. Fatty Acid Biosynthesis Pathways in *Methylomicrobium buryatense* 5G(B1). *Front Microbiol* 7, 2167, (2016).

52 Yu, W. J., Lee, J. W., Nguyen, N. L., Rhee, S. K. & Park, S. J. The characteristics and comparative analysis of methanotrophs reveal genomic insights into *Methylomicrobium* sp. enriched from marine sediments. *Syst Appl Microbiol* 41, 415-426, (2018).

53 Nguyen, A. D. et al. Systematic metabolic engineering of *Methylomicrobium alcaliphilum* 20Z for 2,3 -butanediol production from methane. *Metab Eng* 47, 323-333, (2018).

54 Henard, C. A., Akberdin, I. R., Kalyuzhnaya, M. G. & Guarnieri, M. T. Muconic acid production from methane using rationally-engineered methanotrophic biocatalysts. *Green Chemistry* 21, 6731-6737, (2019).

55 Fei, Q. et al. Bioconversion of natural gas to liquid fuel: opportunities and challenges. *Biotechnol Adv* 32, 596-614, (2014).

56 Collins, D. A. & Kalyuzhnaya, M. G. Navigating methane metabolism: Enzymes, compartments, and networks. *Methods Enzymol* 613, 349-383, (2018).

57 Puri, A. W. et al. Genetic tools for the industrially promising methanotroph *Methylomicrobium buryatense. Appl Environ Microbiol* 81, 1775-1781, (2015).

58 Ham, T. S. et al. Design, implementation and practice of JBEI-ICE: an open source biological part registry platform and tools. *Nucleic Acids Res* 40, el41, (2012).

59 Baidoo EEK, W. G., Joshua C, Teixeira Benites V, Keasling JD Microbial Metabolomics: Methods and Protocols, Liquid Chromatography and Mass Spectrometry Analysis of Isoprenoid Intermediates in *Escherichia coli. Humana Press Inc. Chapter* 11, (2019).

60 Kim, J. et al. Engineering *Saccharomyces cerevisiae* for isoprenol production. *Metab Eng* 64, 154- 166, (2021).

61 Çakmak, H., Güngörmedi, G., Dikmen, G., Çelik, P. A. & Çabuk, A. The true methodology for rhamnolipid: Various solvents affect rhamnolipid characteristics. *European Journal of Lipid Science and Technology* 119, (2017).

62 Changhao Bi, P. S., Jana Miiller, Yi-Chun Yeh, Swapnil R Chhabra, Harry R Beller, & Hillson, S. W. S. v. N. J. Development of a broad-host synthetic biology toolbox for *Ralstonia eutropha* and its application to engineering hydrocarbon biofuel production. 107, 1-10 (2013).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Adaptive Evolution of *Methylotuvimicrobium alcaliphilum* to Grow in the Presence of Rhamnolipids Improves Fatty Acid and Rhamnolipid Production From $CH_4$ Rhamnolipids (RL) are well-studied biosurfactants naturally produced by pathogenic strains of *P. aeruginosa*. Current methods to produce RLs in native and heterologous hosts have focused on carbohydrates as production substrate; however, methane ($CH_4$) provides an intriguing alternative as a substrate for RL production because it is low-cost and may mitigate greenhouse gas emissions. Herein is demonstrated RL production from $CH_4$ by *Methylotuvimicrobium alcaliphilum* DSM19304. RLs are inhibitory to *M. alcaliphilum* growth at low concentrations (<0.05 g/L). Adaptive laboratory evolution is performed by growing *M. alcaliphilum* in increasing concentrations of RLs, producing a strain that grew in the presence of g/L of RLs. Metabolomics and proteomics of the adapted strain grown on $CH_4$ in the absence of RLs revealed metabolic changes, increase in fatty acid production and secretion, alterations in gluconeogenesis, and increased secretion of lactate and osmolyte products compared to the parent strain. Expression of plasmid borne RL production genes in the parent *M. alcaliphilum* strain resulted in cessation of growth and cell death. In contrast, the adapted strain transformed with the RL production genes show no growth inhibition and produced up to 1 μM of RLs, a 600-fold increase compared to the parent strain, solely from $CH_4$ with no added supplementations. This work has promise for developing technologies to produce fatty acid-derived bioproducts, including biosurfactants, from $CH_4$.

*M. alcaliphilum* is engineered to produce rhamnolipids from $CH_4$ without additional mixed or expensive substrate supplementation. The wild type *M. alcaliphilum* strain exhibited inhibited growth when the *P. aeruginosa* rhl genes are expressed; however, adaptation of *M. alcaliphilum* to grow in the presence of RLs produced an evolved strain tolerant to RLs and is able to produce up to 1 μM monorhamnolipid from methane.

RESULTS AND DISCUSSION

2.1 Impact of Rhamnolipids on Growth of *M. alcaliphilum*

Figure 2:
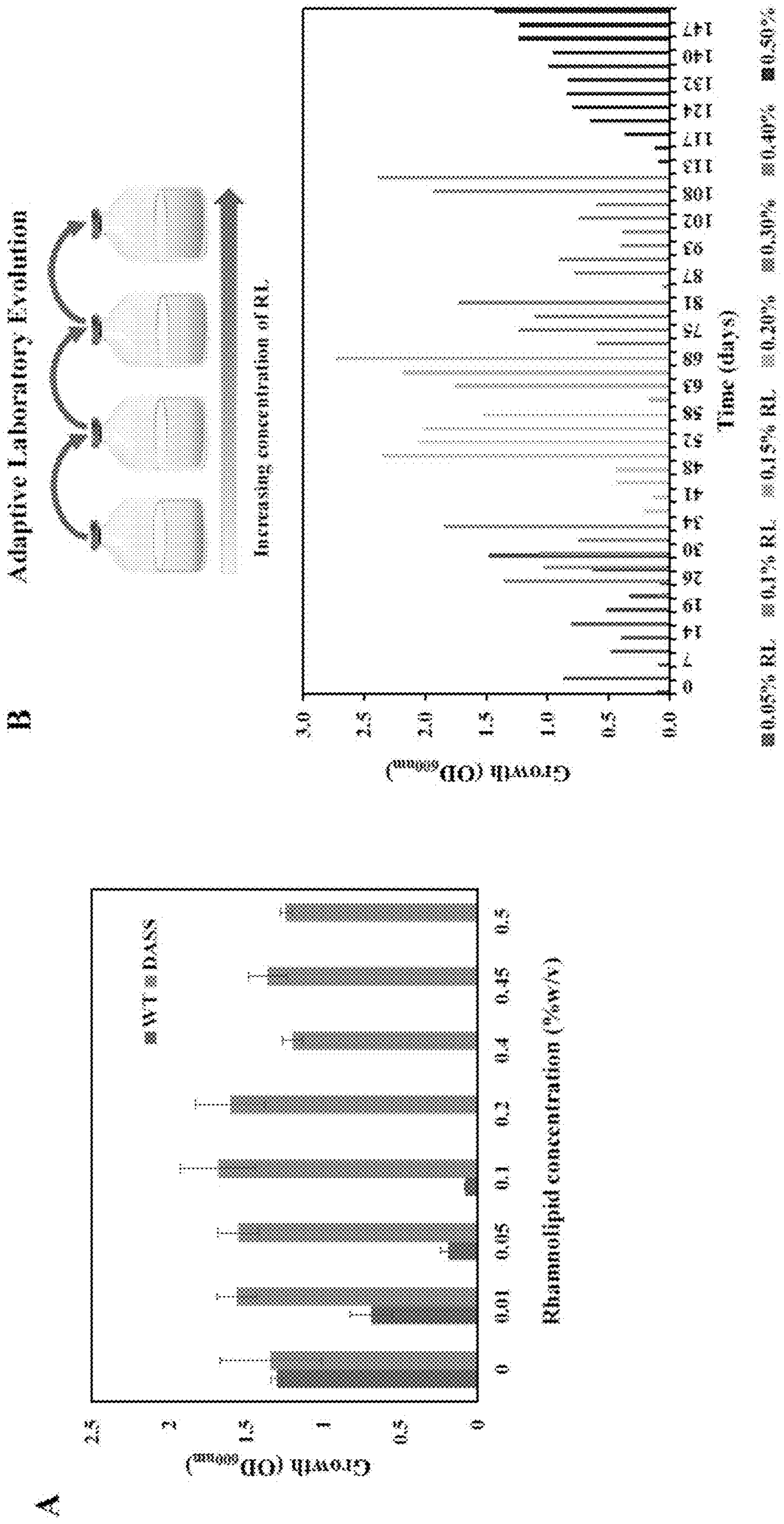
FIG. 2. A) Inhibitory effects of increasing rhamnolipids (RL) concentration on growth of *M. alcahphilum* strain DSM19304 (WT) and strain DASS, grown on Pi medium with $CH_4$. B) Adaptive laboratory evolution of *M. alcaliphilum* by serial transfers in RL containing Pi medium for tolerization. C) Growth profile of strain WT and DASS in Pi medium with $CH_4$. D) Evaluation of C-source responsible for growth of strains WT and DASS when grown with or without $CH_4$ in Pi medium supplemented with 0.5% (w/v) RL. WT, wild type strain DSM19304; DASS, RL tolerant strain created during this work.

*M. alcaliphilum* converts methane by sequential oxidation to formaldehyde, which enters the central carbon metabolism through the RUMP pathway[39]. *M. alcaliphilum* produces high amounts of glycogen, sucrose and ectoine with smaller amounts of lactate, formate, succinate and no known reports of RLs[38,40,41]. Rhamnolipids are used as biocontrol/anti-microbial agents, and increasing rhamnolipid concentrations are found to negatively impact growth of Gram-negative and Gram-positive heterologous hosts, *E. coli, Bacillus subtilis* and *Corynebacterium glutamicum*[23]. Therefore, *M. alcaliphilum* growth is tested in the presence of RLs. Compared to the maximum optical density of *M. alcaliphilum* after 36 hours of culture, a 50% reduction in final optical density is observed when the medium is amended with 0.1 g/L RL and almost complete inhibition is observed with 1 g/L RL amendment (FIG. 2A). The RL toxicity to *M. alcaliphilum* is much higher than reported concentrations in other Gram-negative host like *E. coli* (>90 g/L). The toxicity of RLs to *M. alcaliphilum* required adaptive evolution to permit the strain to produce rhamnolipids.

2.2 Adaptive Laboratory Evolution of *M. alcaliphilum*

A course of adaptive laboratory evolution to allow *M. alcaliphilum* to grow on $CH_4$ in the RLs is followed for four months. During this adaptation, *M. alcaliphilum* strain DSM19304 (hereafter referred as WT, wild type) is subjected to gradually increasing RL concentration starting from 0.5 g/L to 5 g/L (FIG. 2B). At the end of multiple transfers over a period of four months, an *M. alcaliphilum* strain tolerant to RLs (strain DASS) is obtained. *M. alcahphilum* strain DASS tolerated 5 g/L rhamnolipids with comparable final optical density ($OD_{600nm}$) and growth profile to the WT strain (FIG. 2A and 2C). Incubation of the DASS strain in 5 g/L RL did not promote growth in the absence of $CH_4$, indicating that *M. alcahphilum* did not adapt to grow with RLs as a carbon source (FIG. 2D).

2.3 Strain Characterization

To discern the phenotypic difference between the WT and DASS strains, gas chromatography/mass spectrometry (GC/MS) analysis of fatty acids, proteomics and targeted metabolomics are performed on both strains grown on $CH_4$ in the absence of rhamnolipids. The results of these experiments are discussed here.

2.3.1 Fatty Acid Assessment

Fatty acids are a vital component of microbial cells, which are used as building blocks to construct cell membranes, as well as to provide precursors for synthesis of storage, energy and signaling molecules[42]. Surfactants and detergents solubilize the lipids of the membrane and disrupt cell structure[43]. Therefore, *M. alcahphilum* DASS may have alterations in its fatty acid and/or lipid biosynthesis that enabled the strain to tolerate higher RL concentrations relative to the WT strain. The approach is to establish preliminary evidence for this hypothesis by quantifying long chain fatty acids produced by the strains grown on $CH_4$. Long chain (LC) fatty acids (>$C_{12}$) are known precursors to phospholipids (PL) and lipopolysaccharides (LPS) that constitute the cell membrane[42]. Moreover, type-I methanotrophs, including *M. alcahphilum* are known to contain mainly 16:0 and 16:1 fatty acids[44,45]. GC/MS analysis is performed at 24 and 48 hours for the cell pellets and supernatants and focused on $C_{16}$ and $C_{18}$ fatty acids that are involved in PL and LPS synthesis (Table 1).

Relatively high abundance of $C_{16:0}$ fatty acid is observed in the cell pellets of both strains, WT and DASS (Table 1), which are consistent with previous findings of other type-I methanotrophs[44]. However, when strains WT and DASS are compared to each other, $C_{16:0}$ concentrations are ~2x higher in strain DASS in the cell pellet at 48 h. The $C_{16:1}$ fatty acid concentration is found 1.5x- higher in cell pellets and 5-6x higher in supernatant of strain DASS compared to WT (Table 1). Also, $C_{18:1}$ is undetected in the supernatant of the WT strain but found at similar abundance to the $C_{16:1}$ fatty acid in the DASS strain. Therefore, the DASS strain produces higher amounts of fatty acids than the WT strain and secretes them at higher levels into the medium. Excretion of free fatty acids is not a regular occurrence in methanotrophic bacteria[32] It is proposed, in strain DASS, to maintain cell membrane integrity from solubilizing in surfactant, a high rate of fatty acid synthesis must be maintained to continually replenish phospholipids and lipopolysaccharide layers of cell membrane, as suggested by the observed high C16:0, C16:1, C18:1 fatty acid cell pellet level (Table 1). At the same time, to maintain normal lipid to protein ratio for cell homeostasis, excess fatty acids must be secreted out or stored as intracellular granules (like, PHAs)[46]. Since, type-1 methanotrophs are known to accumulate glycogen and not PHAs, the outlet of fatty acids in this host perhaps becomes excretion. The possibility of enhancing the secretion of free fatty acids has been explored by engineering many microbial platforms[47]. *M. alcahphilum* DASS is innately capable of improved fatty acid production and could serve as a foundational strain for further development of fatty acid-based biofuel/chemical production platform from $CH_4$.

TABLE 1

Fatty acid methyl ester (FAME) content of *M. alcaliphilum* strains DSM19304 (WT) and DASS.

| Fatty | Strain DASS | | | | Strain WT | | | |
|---|---|---|---|---|---|---|---|---|
| | Supernatant (nM) | | Intracellular (nM) | | Supernatant (nM) | | Intracellular (nM) | |
| acid | 24 h | 48 h | 24 h | 48 h | 24 h | 48 h | 24 h | 48 h |
| C16:0 | UD | 0.14 ± 0.01 | 28.71 ± 8.15 | 101.93 ± 12.81 | UD | UD | 23.68 ± 2.42 | 49.72 ± 20.47 |
| C16:3 | 19.04 ± 5.88 | 15.89 ± 0.92 | 12.57 ± 2.50 | 14.54 ± 1.56 | 2.92 ± 0.51 | 3.19 ± 0.71 | 8.09 ± 1.30 | 9.18 ± 0.78 |
| C18:1 | 19.07 ± 7.15 | 13.89 ± 1.26 | 7.92 ± 4.25 | 8.22 ± 2.09 | UD | UD | 2.63 ± 0.43 | 2.28 ± 1.94 |
| C18:2 | 26.14 ± 6.58 | 12.96 ± 0.50 | 15.19 ± 4.66 | 15.72 ± 4.78 | 13.27 ± 1.53 | 14.76 ± 2.71 | 17.32 ± 7.44 | 23.75 ± 8.76 |
| C18:3 | 0.15 ± 0.06 | 0.03 ± 0.01 | 0.07 ± 0.04 | 0.06 ± 0.06 | UD | UD | UD | UD |

TABLE 1-continued

Fatty acid methyl ester (FAME) content of *M. alcaliphilum* strains DSM19304 (WT) and DASS.

| | Strain DASS | | | | Strain WT | | | |
|---|---|---|---|---|---|---|---|---|
| Fatty | Supernatant (nM) | | Intracellular (nM) | | Supernatant (nM) | | Intracellular (nM) | |
| acid | 24 h | 48 h | 24 h | 48 h | 24 h | 48 h | 24 h | 48 h |
| C22:0 | 0.33 ± 0 20 | 0.26 ± 0.03 | 0.28 ± 0.07 | 0.25 ± 0.05 | 0.11 ± 0.01 | 0.13 ± 0.03 | 0.23 ± 0.22 | 0.42 ± 0.18 |
| C24:0 | 0.41 ± 0.18 | 053. ± 0.16 | 0.44 ± 0.08 | 0.45 ± 0.05 | 0.57 ± 0.07 | 0.55 ± 0.04 | 0.79 ± 0.30 | 0.59 ± 0.12 |

Cells are cultivated in 4 mL Pi media, in 20 mL anaerobic glass tubes at 30° C. and shaking at 220 rpm under methane: air (1:1) v/v.
nM, nano
Molar concentration;
h, hour.
UD, undetected.

2.3.2 Metabolite and Proteome Analysis of *M. alcahphilum* Strains DASS and WT To study the physiological variations that have occurred due to the surfactant-tolerance in the newly adapted strain DASS with respect to its parent, the metabolome and proteome of strain DASS is analyzed and compared with strain WT. Quantification of select metabolites is performed by LC/MS for both intracellular and extracellular fractions, at 24 hours of growth. Presented in FIG. 3 is a schematic of central carbon metabolism, arrows depicting the fold change ratio of selected peptides as heat map and absolute metabolite concentrations (μM) in graphs. Though, *M. alcahphilum* harbors genes of the Entner-Doudoroff (ED) and Embden-Meyerhof-Parnas (EMP) pathways, it has been characterized previously to metabolize methane preferring the RuMP-EMP route[40](FIG. 3). However, overlaying metabolite concentrations and proteome indicates that in strain DASS, the ED route is now preferred over and in adjunction with EMP, for growth. A comparatively lower concentration of fructose-1,6-phosphate (EMP intermediate) and higher concentration of 6-phosphogluconate (ED intermediate) is observed in strain DASS vs WT, supported by modest increase in abundance of proteins (20%) encoding for the key enzymes of the ED pathway, 6-phosphogluconate dehydratase (Edd) and 2-dehydro-3-deoxy-phosphogluconate aldolase (Eda). It is proposed that 6PG is subsequently converted to 2-dehydro-3-deoxy-phosphogluconate (KDPG), followed by conversion to pyruvate and glyceraldehyde-3-phosphate (GAP) via Edd and Eda, respectively. Considering that KDPG accumulation might inhibit cell growth, it is not accumulated in the cells, instead it is immediately converted to pyruvate (1.5-fold in DASS vs WT) and GAP[48]. Though GAP is not detected, the higher concentration of phosphoenolpyruvate (PEP) pool in strain DASS is suggestive of higher GAP levels. Phosphorylated sugar intermediates like fructose-6-phosphate (F6P) and glucose-6-phosphate (G6P) also detected in the culture medium of strain DASS only, which is indicative of stress response. Among intermediates of the TCA cycle, increased amounts of succinate, fumarate, and malate are observed in the cells and in the culture medium (FIG. 3). According to proteomic data, malate dehydrogenase (Mdh), which catalyzes the conversion of malate to oxaloacetate is downregulated in strain DASS. The reduction of carbon flux via Mdh, could explain 1.2-fold higher levels of secreted malate in the newly evolved strain (FIG. 3). 2-fold higher internal malonyl-CoA concentration is also observed in strain DASS, a direct precursor to fatty acid biosynthesis. An increase of 50% in AccA protein abundance, further supporting the finding of increased fatty acid biosynthesis by strain DASS (FIG. 3, Table 1).

Figure 4:
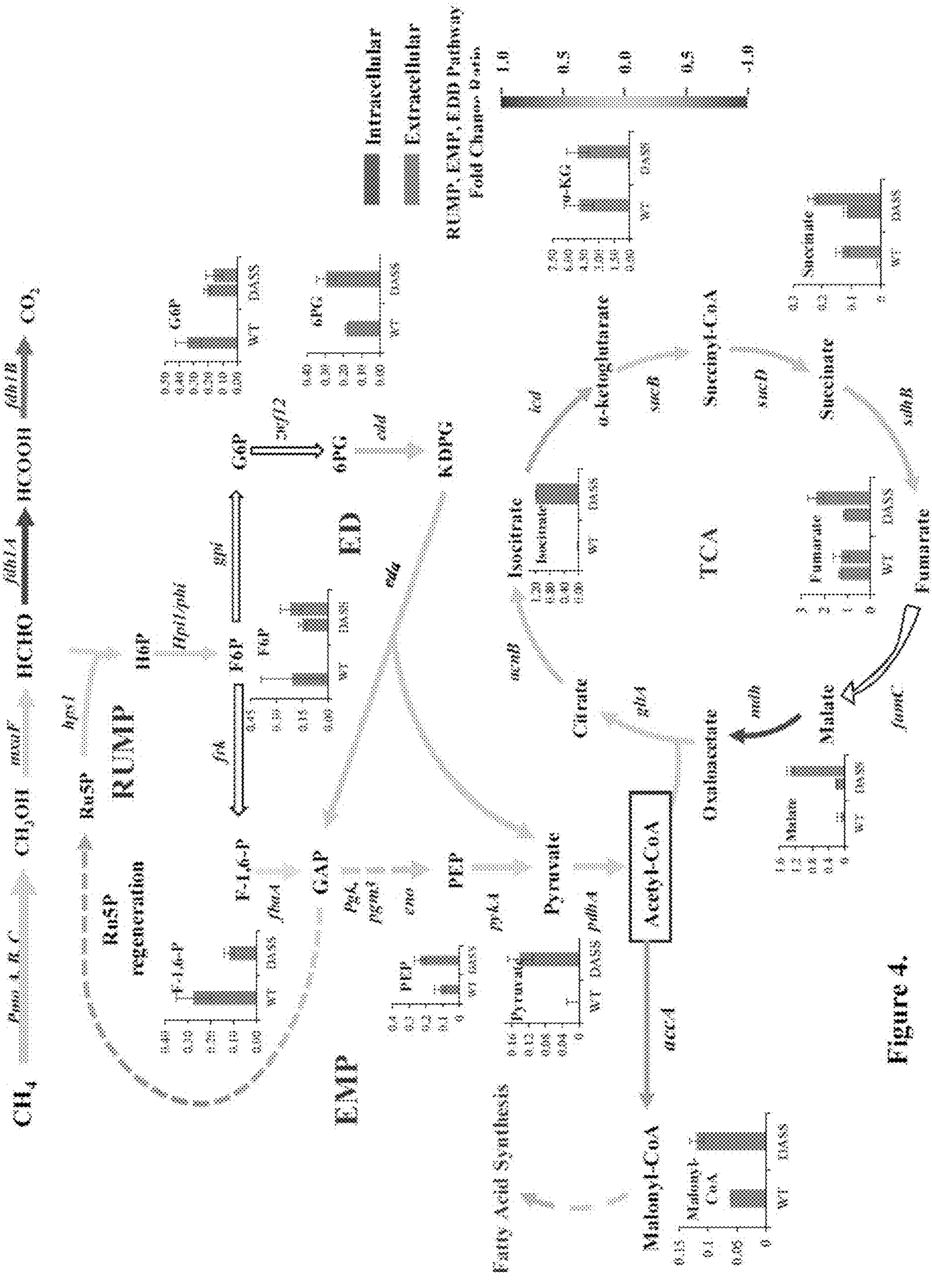
FIG. 4: Absolute metabolite concentrations detected in strains WT and DASS. A) Lactate, B) Ectoine. C) Sucrose and D) Rhamnose. Cells are cultivated in 4 mL Pi media, in 20 mL anaerobic glass tubes at 30° C. and shaking at 220 rpm, under methane: air (1:1) v/v. Green-intracellular concentration; orange, extracellular concentration; UD, undetected.

Other secreted products included lactate as well as sucrose and ectoine. Another key metabolite, rhamnose is also evaluated since it is a native precursor of interest for heterologous rhamnolipid synthesis as well as being involved in LPS biosynthesis. Lactate is undetected in the WT strain but present at ~30 μM in the extracellular fraction from the strain DASS (FIG. 4). Both, ectoine and sucrose are well characterized osmo-protectants synthesized by *Methylotuvimicrobium alcahphilum* typically in response to high salinity and alkalinity of the medium[40,49,50]. In strain DASS, secreted sucrose level is detected to be ~30 fold higher though internal sucrose concentration is found unaffected. Overall ectoine production is found elevated in the strain DASS with ~1.6-fold increase with respect to the WT. Moreover, it is observed that although the intracellular concentration of rhamnose is unchanged, rhamnose secretion is 1.1-fold higher in strain DASS compared to the WT (FIG. 4).

Figure 5:
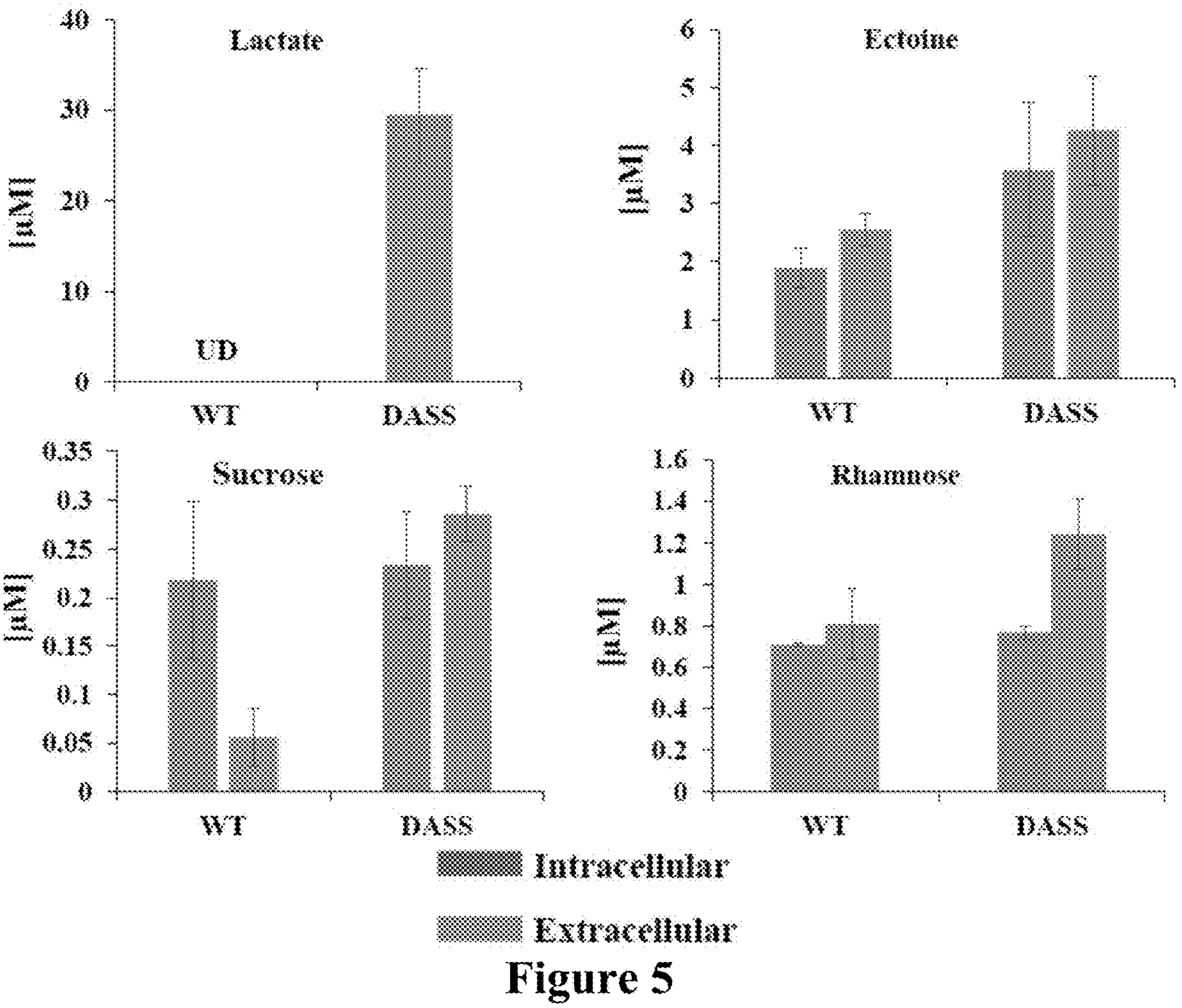
FIG. 5. Heat map representing the fold change of peptide count [$NSAF_{DASS}/NSAF_{WT}$] (NSAF, normalized spectral abundance factor) in strain DASS compared to WT at 24 h. UC, hypothetical and/or uncharacterized proteins; UC (transmembrane), uncharacterized protein with transmembrane signal peptide domain. Yellow to Green-significant upregulated (2.3≥FC≥0.32); Orange to Red- significant downregulated (−0.32≥FC≥−1.8).

Whole cellular proteome of the strains is evaluated and a total of 725 expressed proteins are detected at the two experimental time points. Out of the total, 118 proteins are observed to be downregulated and 102 are found upregulated, however, after qualifying $p \leq 0.05$ and $\log_2 FC \geq 0.32$ value significance test, only 30 proteins are characterized as significantly down and up regulated, respectively at 24 h. The fold change in NSAF of proteins in strains DASS to WT at 24 h, is listed and represented as heat map in FIG. 5. As listed in FIG. 5, at 24 h, more than 200% increase in acetyl-CoA carboxylase subunits AccB and 50% increase in subunit AccA are observed, involved in the synthesis of malonyl Co-A from acetyl-CoA, a direct precursor of fatty acid synthesis pathway[51]. An increase in abundance of proteins is also seen involved in translation, export, and quality control machinery (RpsN, RpsF, RpsJ, RpoX, Frr, MEALZ_1142, SecD), and many uncharacterized proteins with transmembrane domain and OmpA-like outer membrane domain (MEALZ_1111, 0519) (FIG. 5). Apparently, the adaptation to overcome environmental stress to surfactant resulted in an increase in abundance of heat shock and other stress response proteins and chaperonins (MEALZ_1779, 2580, Csp) in strain DASS. Increased abundance in transcription factors (GreA), DNA replication/repair proteins (Ssb, GuaB, PurA) and ion-exchange/cell response regulators (MEALZ_3035) is also observed to maintain cellular homeostasis. >50% increase in the protein abundance for carbohydrate metabolism, methanol and formaldehyde oxidation (MxaK, Mxal, Fae2), ribulose mono-phosphate pathway enzyme expression for methane metabolism (Ppe) is also observed. However, enzymes involved in glycolysis/gluconeogenesis (FfsA, MEALZ_2872, Mtb, PdhD, Gap, Pgk) are downregulated (FIG. 5), which is also reflected in the central carbon metabolite data (FIG. 3). A lower abundances of proteins in the glycogen biosynthetic pathway enzymes (GlgA2, GalU) is also observed, which substantiates the diversion of central carbon to ectoine, lactate and sucrose higher production by strain DASS. The similar observation is supported through 48 h of growth (FIG. 9).

Based on the metabolomic and proteomics data, at 24 h of cultivation, the DASS strain shifted central carbon processing from EMP to ED, simultaneous activity of both pathways contributed to higher pyruvate pools. The observation of lactic acid secretion by strain DASS is likely results from the increased internal pyruvate pool. This work on strain DASS characterization identifies the unique metabolic changes due to surfactant acclimatization, reinforced evidence of the increased pool of fatty acids and rhamnose, which is a positive outcome for engineering this strain for rhamnolipid biosynthesis.

2.4 Rhamnolipid Biosynthesis

*M. alcahphilum* is not known to produce RLs, so it is essential to identify the availability of precursors for heterologous RL synthesis in this host. Including the four gene (rhlYZAB) enzyme cassette from *P. aeruginosa*, the pre-requisites for RL production are fatty acid biosynthesis/(3-oxidation and an available pool of rhamnose. Fatty acid biosynthesis is well characterized for*M. buryatense* 5 GB(1), a methanotroph closely related to *M. alcahphilum*[52]; however, reports of R-3-hydroxydecanoyl-CoA (direct precursor to RL) and enzymes for RL synthesis are not known. Internal rhamnose pools have been reported earlier in *M. alcahphilum* and rhamnose pools in the strains are also observed during strain characterization (FIG. 5D).

2.4.1 Heterologous Rhamnolipid Production in *M. alcahphilum* Strains WT (Parent)

Figure 6:
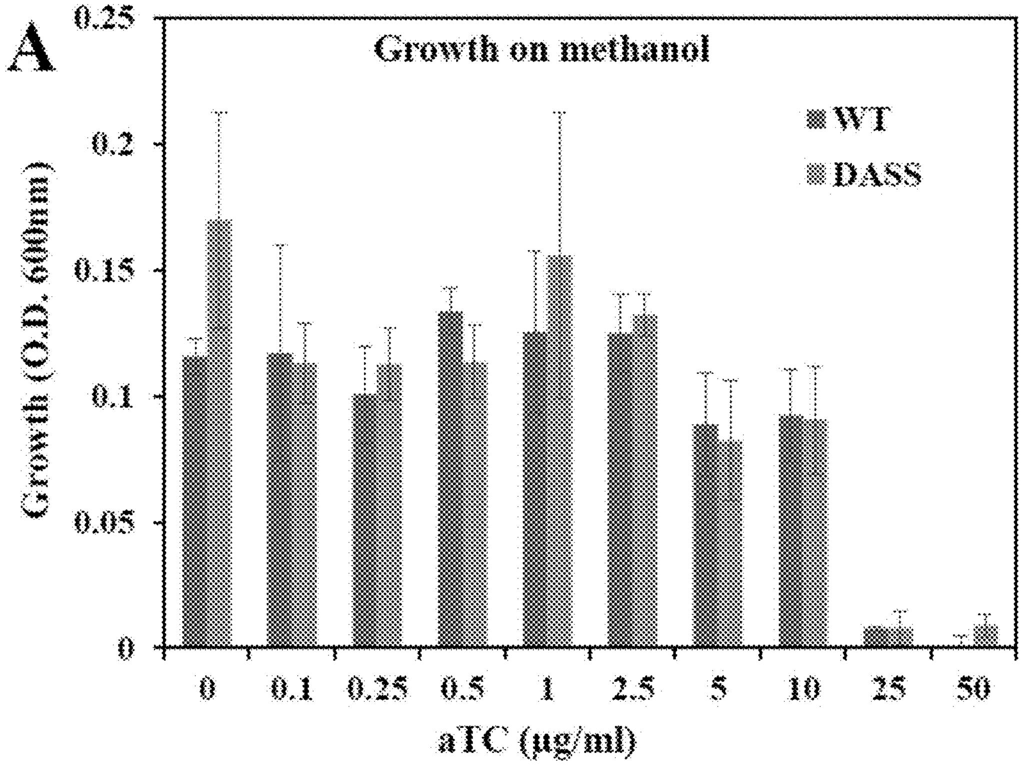
FIG. 6. A) Comparison of growth of *M. alcaliphilum* strains WT and WT harboring plasmids pDA17 and pDA21. B) Comparison of growth of *M. alcaliphilum* strains DASS and DASS harboring plasmids pDA17 and pDA21. Cells are grown as batch cultures in 4 mL Pi media, in 20 mL anaerobic glass tubes at 30° C. and shaking at 220 rpm, under methane: air (1:1) v/v. Dashed lines and hollow markers, WT; solid lines and markers, strain DASS; black circles, parent strains; blue triangles, pDA17; red squares, pDA21.

Codon optimized rhlYZAB are cloned in shuttle vector, pCAH01 under inducible ($P_{tet}$: tetracycline; pDA17) and constitutive ($P_{sps}$: sucrose phosphate synthase; pDA21) promoters (Table 2). The inducible $P_{tet}$ promoter has been shown to express heterologous ldh (lactate dehydrogenase) in Type-1 methanotrophs for lactic acid production[33], and the constitutive mxaF (methane monooxygenase, MMO) promoter has been used for heterologous production of 2,3-butanediol[53]. In this work, for pDA21, *P. aeruginosa* rhlYZAB expression is controlled by the constitutive *M. alcahphilum* sucrose phosphate synthase promoter ($P_{sps}$), since *M. alcahphilum* accumulates high amounts of sucrose in their environment in response to maintaining osmotic balance (FIG. 4C). The resulting plasmid constructs with rhlYZAB under $P_{tet}$ (pDA17) and $P_{sps}$ (pDA21) are introduced in *M. alcahphilum* via conjugation and the strains are monitored for growth and RL production. *M. alcahphilum* WT and WT harboring plasmids pDA17 and pDA21 are cultured in methane and monitored for growth, where *M. alcahphilum* (pDA21) and strain WT are grown without any inducer. Poor growth of *M. alcahphilum* (pDA17) and (pDA21) compared to strain WT (FIG. 6A) is observed, with optical densities of 0.12±0.05, 0.53±0.11 and 1.1±0.31, respectively. A detectable amount of mono-rhamnolipid is produced; however, the titers are low, with the pDA21 strain producing 63 nM of RL (Table 3). The observation of cell lysis in the cultures where the RL production genes are expressed is indicative that the gene products and/or the RLs are toxic to *M. alcahphilum* WT (FIG. 6A).

TABLE 2

Bacterial strains and plasmids used in the study

| Strains and Plasmids | Characteristics | Source |
|---|---|---|
| Strains: | | |
| *E. coli* TOP10 | $F^-$ mcrA Δ(mrr-hsdRMS-mcrBC) φ80lacZΔM15ΔlacX74 recA1 araD139 (ara-leu)7697 galE15 galK16 rpsL endA1 $\lambda^-$ | JBEI collection |
| *E. coli* S17-1 | $Tp^r$ $Sm^r$ recA thi pro hsd($r^-$ $m^+$)RP4-2-Tc::Mu::Km Tn7 | JBEI collection |
| *Methylotuvimicrobium alcaliphilum* 20Z (DSM19304) | Wild type | DSMZ (JPUB__019705) |
| *Methylotuvimicrobium alcaliphilum* DASS | Tolerant to rhamnolipid | This work (JPUB__019708) |
| Plasmids: | | |
| pCAH01 | $P_{tetA}$ bla-tetR ori$R_{CoEI\ oriRRP4/RK2}$, ori$T_{RP4/RK2}$, trfA ahp | Henard et. al. 2016 |
| pET28b (+) | E. coli expression vector- kanR | Novagen |
| pUC57 | E. coli cloning vector ampR | Genscript |
| pDA15 | pET28b(+) $P_{T7}$ rhlY rhlZ rhlA rhlB | This work (JPUB__019714) |
| pDA17 | pCAH01 $P_{tet}$ rhlY rhlZ rhlA rhlB | This work (JPUB__019715) |
| pDA21 | pCAH01 $P_{sps}$ rhlY rhlZ rhlA rhlB | This work (JPUB__019717) |

All strains and plasmids constructed in this work and their related information can be found in JBEI registry (webpage for: public-registry.jbei.org/folders/713).

TABLE 3

Rhamnolipid titer obtained by *M. alcaliphilum* strains WT and DASS.

| Strain (plasmid) | Time (h) | O.D.$_{600\ nm}$ | RL (nM) Intracellular | RL (nM) Extracellular |
|---|---|---|---|---|
| WT (pDA17)*[a] | 24 | 0.12 ± 0.01 | 7 ± 0.01 | 10 ± 0.01 |
| WT (pDA21)*[b] | 24 | 0.53 ± 0.11 | 2 ± 0.01 | 61 ± 0.01 |
| DASS (pDA17)[a] | 24 | 1.33 ± 0.11 | 119 ± 0.01 | 315 ± 0.06 |
| | 48 | 1.45 ± 0.30 | 367 ± 0.03 | 293 ± 0.05 |
| DASS (pDA21)[b] | 24 | 1.65 ± 0.10 | 621 ± 0.08 | 135 ± 0.03 |
| | 48 | 1.55 ± 0.10 | 871 ± 0.15 | 132 ± 0.01 |

Cells are cultivated as batch-cultures in 4 mL Pi media, in 20 mL anaerobic glass tubes at 30° C. and shaking at 220 rpm, under methane: air (1:1) v/v. h, hours; nM, nanomolar concentration.

O.D. (optical density) and RL values at 24 h.

*48 h time point for WT (plasmid) culture is not processed due to cell lysis;

[a]$P_{tet}$ promoter;

[b]$P_{sps}$ promoter driving rhlABYZ expression.

2.4.2 Heterologous Rhamnolipid Production in *M. alcahphilum* Strain DASS (Tolerized)

The toxicity observed when the RL production genes are expressed in *M. alcahphilum* results suggested that the DASS strain might be more amenable to RL production. Expression of the rhlYZAB cassette in strain DASS containing pDA17 and pDA21 had negligible impact on cell growth (FIG. 6B). In strain DASS, RLs are produced at 100-fold (pDA17) and 600-fold (pDA21) higher titer, respectively, than in strain WT (Table 3), with the pDA21-containg strain producing 1 uM of RLs (0.65 mg/L). However, strain pDA17 reported highest secreted concentration of RL at ~300 nM, which is achieved after 24 h. From 24 h to 48 h, the RLs in pDA17 strain accumulated intracellularly. The increase in RL titer observed for the DASS strains is consistent with the increased tolerance to rhamnolipid obtained by adaptive evolution as well as the increased production of free fatty acids that are the precursors for RL production. In the future, metabolic pathway engineering of strain DASS to eliminate co-product synthesis like lactic acid, sucrose or ectoine as well as β-oxidation (ΔfadABE) can be evaluated for their impact on improving RL titer. Additionally, continuous flow bio-reactor processes can be performed to obtain high titer of RL and compute rates and yields of RL production from $CH_4$, as has been shown for other bioproducts from methanotrophs[33,54,55]. Moreover, other heterologous genes and their expression can be assessed under constitutive $P_{sps}$ promoter for its effectiveness in continued product synthesis in sucrose-producing methanotrophic platforms.

CONCLUSION

The work presented here is a proof-of-concept study to produce RLs from $CH_4$. This study demonstrated that rhamnolipids inhibit the growth of *M. alcahphdum*; however, after adaptive laboratory evolution of *M. alcahphdum* on gradually increasing RL concentrations, *M. alcahphdum* metabolism is able to grow in the presence of 10-fold higher concentrations of RLs compared to the parent strain. It is also established that the metabolic changes directly impacted fatty acid synthesis in the cells and strain DASS is found to have acquired natural ability to secrete ~5-fold higher fatty acids in the medium than the parent strain. A strategy of adaptive laboratory evolution enables the newly generated strain DASS produce ~600-fold high titer of RL compared to strain WT, where the latter failed to survive when expressing the recombinant RL biosynthetic pathway. The increased fatty acid biosynthesis and secretion by strain DASS suggests a route to develop methanotrophic strains with higher levels of fatty acid production from $CH_4$. Genome sequencing will establish the causative mutations, which may be applied to developing strains that produce fatty-acid-derived fuels and bioproducts.

MATERIALS AND METHODS

4.1 Bacterial Strains, Plasmids, and Growth Conditions

Figure 7:
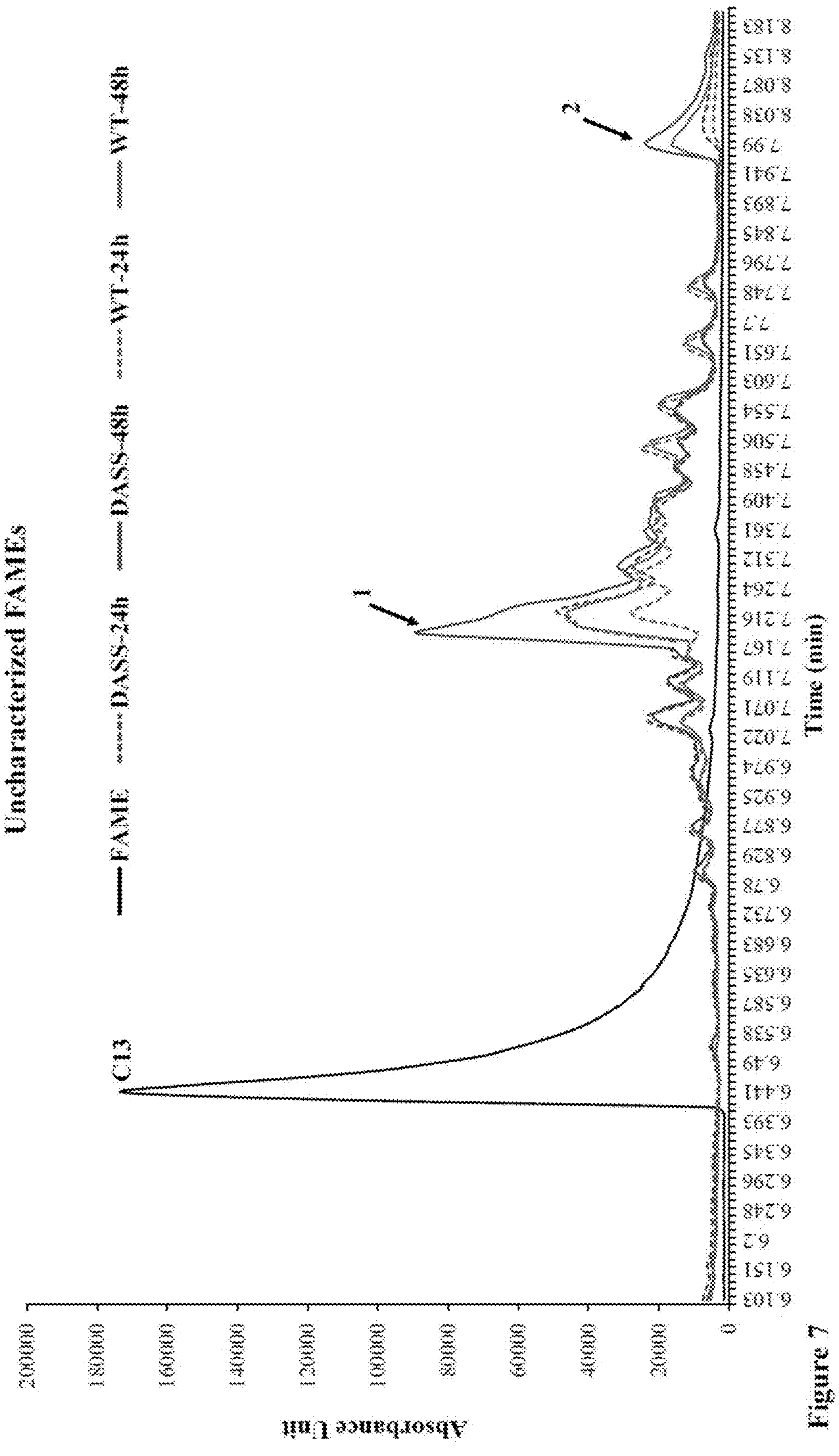
FIG. 7. Chromatogram of unidentified and identical FAMES peaks 1 and 2. Black-known standard fatty acid C13 FAME, red-M. alcaliphilum strain DASS; green-*M. alcaliphilum* strain WT. Solid line-48 hour, Dashed line-24 hour.

*Escherichia coli* and *M. alcahphdum* strains and plasmids used in this study are listed in Table 2. Luria-Bertani (LB) broth and agar plates are routinely used to culture *E. coli* cells at 37° C. For routine cultivation of*M. alcahphilum* strain WT (wild type) and its derivatives, Pi (π) media with 3% (w/v) NaCl is used as described in Collins and Kaluzhnaya.[56] When needed, kanamycin (Kan) is added to the growth medium at 100 μg/mL for *M. alcahphilum* and 50 μg/mL for *E. coli* cultures. Ampicillin is added to the growth medium at 100 μg/mL. *M. alcahphilum* cell cultures are grown as batch cultures, either 4 mL culture in 20 mL anaerobic glass tubes or 10 mL culture in 50 mL serum vials, under a methane (99.9%; Airgas): air atmosphere (1:1). Cell cultures are incubated at 30° shaking at 220 rpm. Cell growth is measured as optical density (OD 600 nm) using Spectronic 200E spectroscope at time points mentioned in results and discussion. Single colony isolates and transformant selections are performed on Pi media agar plates incubated in anaerobic jars (Oxoid; Remel) under a methane-air atmosphere (1:1). For *M. alcahphilum* (pDA17) induction, antimicrobial activity of $P_{tet}$ inducer, anhydrotetracycline (aTC) is first evaluated (FIG. 7) on methanol, it is observed that aTC antimicrobial effect on *M. alcahphilum* is apparent at concentration >2.5 μg/mL. Thus, based on the observation and previous report[33], concentration of 1 μg/mL aTC is used for optimal gene expression. *M. alcahphilum* (pDA17) cultures are induced with anhydrotetracycline (1 μg/mL) at time of inoculation[33].

4.2 Plasmid Construction and Transformation

Figure 8:
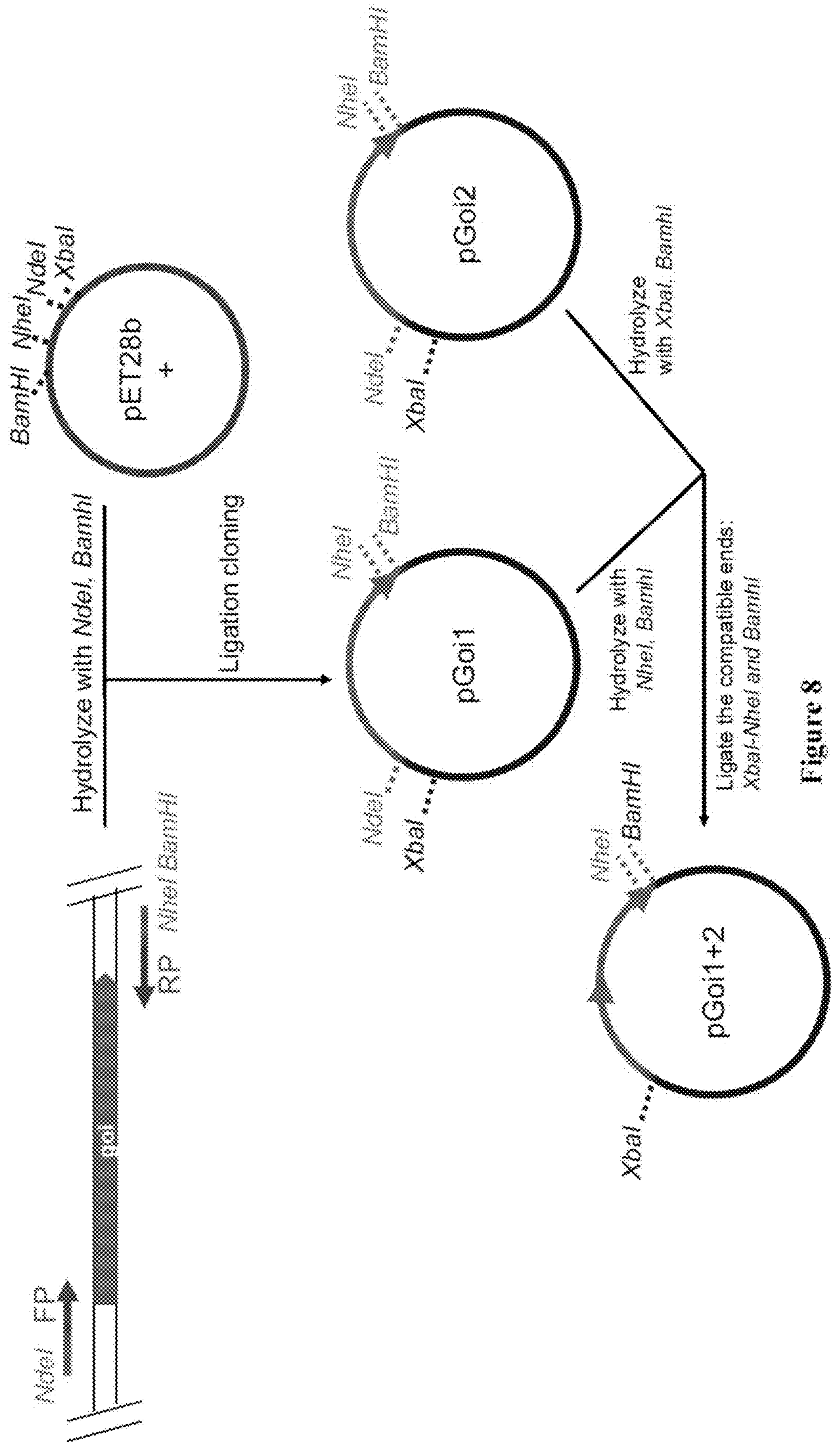
FIG. 8. Schematic of concatenation assembly of rhlYZAB in pET28b(+) vector with individual RBS upstream of each gene. FP and RP, forward and reverse primer; Goi, gene of interest; BamHl, Nhel, Ndel, Xbal, restriction endonucleases.

The rhamnolipid biosynthetic cassette from *P. aeruginosa* (GenBank RefSeq: NC_002516.2) containing the genes rhlY, Z, A and B encoding R-specific enoyl-CoA hydratase/isomerase, 3-hydroxyacyl-ACP-O-3 hydroxyacyltransferase and rhamnosyl transferase, respectively are codon optimized for optimal protein expression in *M. alcahphilum* and synthesized by Genscript (Table 5). The codon optimized rhl genes for *M. alcahphilum* are assembled in concatenation in a replicative expression plasmid, pET28b(+) with individual RBS upstream of each gene. Steps of assembly are illustrated in FIG. 8. The assembled rhl cassette is then transferred to methanotrophic replicative shuttle vector pCAH01. Vector pCAH01 has a $P_{tet}$ driven and anhydrotetracycline inducible expression system[33]. For constitutive expression of rhlYZAB, sucrose-phosphate synthase promoter region is added upstream of rhlYZAB cassette, replacing Ptet sequence in pCAH01. The final vector constructs pDA17 ($P_{tet}$-rhlYZAB) and pAD21 (Psps-rhlYZAB) are assembled using Gibson assembly (New England Biolab; NEB). DNA fragments are PCR-amplified using Q5 high-fidelity DNA-polymerase (NEB). PCR products are either gel purified, or column purified using Qiagen agarose gel or PCR product clean-up kits, respectively. All PCR primers used for DNA amplification and plasmid construction are listed in Table 6. Assembled plasmids are transformed to *E. coli* Top10 using chemical DNA transformation method, for propagation and screened by colony PCR and sequence validated by Genewiz sequencing services. Subsequently, plasmids are transformed to *E. coli* strain S17-1 and transferred to M. alcahphilum via conjugation as described by Puri et.al.[57].

All strains and plasmids developed in this work, along with their associated information have been deposited in the public instance of the JBEI Registry[58] (webpage for: public-registry.jbei.org/folders/713).

4.3 Adaptive Laboratory Evolution and Development of *M. alcahphilum* Strain DASS M. alcahphilum strain DSM19304 is grown in batch cultures of 10 mL Pi media in 50 mL serum vials under a methane-air atmosphere at 30° C. with agitation at 200 rpm. To adapt the cells to grow in the presence of RLs, 0.5 g/L RL (90% mono-RL, Millipore Sigma) is supplemented to the starting cell culture. The concentration of RLs is increased gradually and stepwise (1, 1.5, 2, 3, 4 and 5 g/L) to achieve a final strain of *M. alcahphilum* tolerant to 5 g/L RL. A 0.1% inoculum is manually transferred from a growing batch culture to a fresh culture in 48-60h. The RL concentration in the media is increased to next higher concentration when the OD 600 nm at 48 h of the growing batch culture with RL reached similar $OD_{600}$ to WT (>1.0) at the end of 48 h. After the adaptation, single colonies of *M. alcahphilum* strain DASS are isolated on Pi media agar plates. Multiple single colony isolates are confirmed to be *M. alcahphilum* via 16S rRNA sequencing to rule out possibility of co-contaminants. No differences are observed in growth of multiple single colonies that are tested, one clone is selected for further analysis and plasmid transformation.

4.4 Proteomic Analysis

*M. alcahphilum* cell cultures are grown in batch in 10 mL Pi medium in 50 mL serum vials under a methane-air atmosphere. Cell cultures are incubated at 30° shaking at 220 rpm. Both strains are grown for proteomic analysis in triplicates. Cells are harvested at 24 h and 48 h and stored at −80° C. until use. Samples for proteomic analysis are processed and whole proteome is analyzed as described by Yan et.al. (website for: dx.doi.org/10.17504/protocols.io.bf9xjr7n). Normalized Spectral Abundance Factor (NSAF) values obtained are processed to categorize upregulated and downregulated proteins of *M. alcahphilum* strain DASS and WT. p value <0.05 for FC >0.32 are considered significant and are presented in heat map table or as specified.

4.5 Metabolite Analysis

Growing *M. alcahphilum* cell cultures (4 mL in Pi medium) in 20 mL anaerobic glass tubes, are harvested at 24 h and 48 h of growth. *M alcahphilum* strains harboring plasmids are grown with antibiotic and inducer (anhydrotetracycline) as necessary, in the culture medium. 2 mL cell culture is centrifuged at 10,000 rpm for 1 min at room temperature (RT). Thereafter, 1 mL supernatant is stored in a separate tube and the rest is discarded. Cell pellets are immediately quenched with 4° C. cold 100% methanol. Both supernatant and pellets are stored at −20° C. until further processing. All strains, parents and harboring plasmids are grown in technical triplicates for analysis. To analyze central carbon metabolism and associated metabolites, the cells and supernatant are processed separately using aqueous methanol extraction method as described earlier by Baidoo et.al.[59]

Intracellular metabolites are analyzed via liquid chromatography-mass spectrometry (LC-MS; Agilent Technologies 1290 Infinity II UHPLC system and Agilent Technologies 6545 quadrupole time-of-flight mass spectrometer) on a ZIC-pHILIC column (150-mm length, 4.6-mm internal diameter, and 5 μm particle size). The UHPLC method used is as described by Baidoo et. al. and Kim et.al.[59,60] For rhamnolipid analysis the cell pellets and supernatant is processed using acidic (HCl) methanol/chloroform precipitation method described previously by Çakmak et.al.[61] Total rhamnolipids are analyzed using the LC-MS method as described by Amer et.al.(webpage for: protocols.io/edit/lc-ms-analysis-of-rhamnolipid-bu5wny7e).

4.6 Analysis of Fatty Acids

Cell cultures are grown in 4 mL Pi media in 20 mL anaerobic glass tubes, under methane-oxygen at 30° C. and shaking at 220 rpm. 2 mL culture is aspirated at 24 and 48 hour and cell pellets are harvested by centrifugation at 8000 rpm for 10 mins at room temperature. Supernatant and pellets are stored in separate 2 mL Eppendorf tubes at −80° C. until further processing. Total cell fatty acids are analyzed as fatty acid methyl esters (FAMEs) using GC-MS. FAMEs are prepared by transesterification using 2% (v/v) sulfuric acid in methanol (90° C.; 2 h). FAMEs are subsequently extracted in 400 μL hexane, of which 1μL is analyzed on an Agilent 5973-HP6890 GC-MS using a 30 m DB-5 ms capillary column. Electron ionization (EI) GC/MS analyses are performed with a model 7890A GC quadrupole mass spectrometer (Agilent) with a DB-5 fused silica capillary column as described previously[62].

4.7 Materials

All chemicals used in this study are analytical grade. Organic and inorganic chemicals are purchased from Fisher Scientific (Pittsburgh, PA). Biochemicals are from Sigma-Aldrich Co. (St. Louis, MO) and Millipore Sigma (Burlington, MA). Molecular biology reagents and supplies are from New England Biolabs (Ipswich, MA) and Thermo Fisher Scientific (Waltham, MA). Plasmid DNA extraction kit is from QIAGEN (Valencia, CA). DNA clean up kits are from QIAGEN (Valencia, CA). DNA oligonucleotides for PCR are from IDT (Coralville, IA).

Plasmid construction: Prior to assembling the rhlYZAB cassette under Ptet promoter, individual RBS (ribosome binding sequence) are added upstream to translation start sequence (ATG) of each enzyme. To add the RBS, individual genes rhlY , rhlZ, rhlA and rh/B are first amplified using primer with upstream Ndel attached to forward priming sequence (5') and Nhel-Bamhl to reverse priming sequence (3') with Phusion DNA polymerase (Thermo scientific)

TABLE 5

List of primers.

| Name | Sequence (5'-3') | Usage |
|---|---|---|
| DA11-For<br>DA11-Rev | cgcacatatgAGAAGAGAATCGCTGCTT (SEQ ID NO:5)<br>ttacggatccgctagcTTACGCGTATCCTATAGCCATCT (SEQ ID NO: 6) | Codon optimized rhlA |
| DA12-For<br>DA12-Rev | ggcacatatgCACGCGATACTGATAGCCATA (SEQ ID NO: 7)<br>ctatggatccgctagcTTACGACGCAGCCTTCAGCCAT (SEQ ID NO: 8) | Codon optimized rhlB |
| DA13-For<br>DA13-Rev | cgcacatatgAACACAGCCGTGGAACCTTA (SEQ ID NO: 9)<br>ctatggatccgctagcTTAGCAGTTTCTCCACTTCGGGTCTC (SEQ ID NO: 10) | Codon optimized rhlY |
| DA14-For<br>DA14-Rev | ggcacatatgAACGTGCTGTTTGAAGAGA (SEQ ID NO: 11)<br>ctatggatccgctagcTTACAGTCCGGCCAGCGGATGCT (SEQ ID NO: 12) | Codon optimized rhlZ |
| DA18-For<br>DA18-Rev | CGGATATAGTTCCTCCTTTCA (SEQ ID NO: 13)<br>GGATAACAATTCCCCTCTAGAA (SEQ ID NO: 14) | Validating insert at multiple cloning site (pET28b+) |
| DA31-For<br>DA31-Rev | AAGCTTGACCTGTGAAGTG (SEQ ID NO: 15)<br>TTCACTTTTCTCTATCACTGATAG (SEQ ID NO: 16) | pCAH01 backbone for Gibson assembly of pDA17 |
| DA32-For<br>DA32-Rev | cctatcagtgatagagaaaagtgaaTGAACACAGCCGTGGAAC (SEQ ID NO: 17)<br>atttttcacttcacaggtcaagcttCTTACGACGCAGCCTTCAG (SEQ ID NO: 18) | Rhl cassette from pDA15 for Gibson assembly of pDA17 |
| DA33-For<br>DA33-Rev | CATGTTCTTTCCTGCGTTATCC (SEQ ID NO: 19)<br>AGATCCGTGACGCAGTAG (SEQ ID NO: 20) | Validating insert at cloning site (pCAH01) |
| DA44-For<br>DA44-Rev | TGGTGTCGGGTCATGTGAG (SEQ ID NO: 21)<br>GAAAATTGTCGGGAAGATGC (SEQ ID NO: 22) | pCAH01 without $P_{tet}$-amp for Gibson assembly for pDA21 |
| DA45-For<br>DA45-Rev | ctggccttttgctcacatgacccgacaccaGGTACTCAAAAAGCCGGTC (SEQ ID NO: 23)<br>ccacggctgtgttcaTCACGAACAACTATCTCAAG (SEQ ID NO: 24) | Psps from *M. alcaliphilum* genome |
| DA46-For<br>DA46-Rev | gatagttgttcgtgaTGAACACAGCCGTGGAAC (SEQ ID NO: 25)<br>atcagatcacgcatcttcccgacaattttcTTACGACGCAGCCTTCAG (SEQ ID NO: 26) | Rhl cassette from pDA15 for Gibson assembly of pDA21 |

Homology tails for Gibson assembly and restriction enzyme sites are in lower case.

TABLE 6

Codon-optimized nucleotide sequence

| Gene | Optimized nucleotide sequence |
|---|---|
| rhlA | ATGAGAAGAGAATCGCTGCTTGTGAGTGTGTGCAAAGGACTGAGAGTGC<br>ACGTGGAGAGAGTGGGACAGGACCCTGGTAGATCGACAGTGATGCTGGT<br>GAACGGTGCTATGGCGACAACGGCTAGTTTTGCGAGAACGTGCAAATGC<br>CTGGCTGAACACTTTAACGTGGTGCTGTTTGATCTGCCTTTTGCGGGACA<br>GTCGAGACAGCATAACCCGCAGAGAGGTCTGATAACAAAGGACGATGAA<br>GTGGAGATACTGCTGGCCCTGATAGAAAGATTTGAGGTGAACCATCTGGT<br>GTCGGCGAGTTGGGGAGGGATAAGTACGCTGCTGGCCCTGAGTAGAAAC<br>CCTAGAGGGATAAGATCGAGTGTGGTGATGGCCTTTGCTCCGGGGCTGAA<br>CCAGGCTATGCTGGACTACGTGGGAAGAGCGCAGGCCCTGATAGAACTG<br>GACGATAAGAGTGCGATAGGTCACCTGCTGAACGAGACAGTGGGGAAAT |

TABLE 6-continued

Codon-optimized nucleotide sequence

| Gene | Optimized nucleotide sequence |
|---|---|
| | ACCTGCCTCAGAGACTGAAGGCGTCGAACCACCAGCACATGGCCAGTCT |
| | GGCTACGGGAGAATACGAGCAGGCCAGATTTCATATAGACCAGGTGCTG |
| | GCCCTGAACGATAGAGGTTACCTGGCTTGCCTGGAGAGAATACAGTCGC |
| | ACGTGCATTTTATAAACGGGAGTTGGGACGAATACACAACGGCGGAGGA |
| | CGCCAGACAGTTTAGAGATTACCTGCCGCACTGCTCGTTTAGTAGAGTGG |
| | AAGGTACAGGGCATTTTCTGGATCTGGAGTCGAAACTGGCCGCTGTGAGA |
| | GTGCACAGAGCCCTGCTGGAACATCTGCTGAAGCAGCCTGAACCGCAGA |
| | GAGCTGAGAGAGCGGCCGGGTTTCACGAGATGGCTATAGGATACGCGTA |
| | A (SEQ ID NO: 1) |
| rhlB | ATGCACGCGATACTGATAGCCATAGGGTCGGCTGGAGACGTGTTTCCTTT |
| | TATAGGGCTGGCTAGAACACTGAAACTGAGAGGACACAGAGTGAGTCTG |
| | TGCACGATACCTGTGTTTAGAGACGCTGTGGAGCAGCATGGGATAGCGTT |
| | TGTGCCGCTGTCGGATGAACTGACATACAGAAGAACGATGGGAGACCCT |
| | AGACTGTGGGACCCTAAGACAAGTTTTGGAGTGCTGTGGCAGGCCATAG |
| | CTGGTATGATAGAACCTGTGTACGAGTACGTGTCGGCGCAGAGACACGA |
| | CGATATAGTGGTGGGGAGTCTGTGGGCTCTGGGAGCTAGAATAGCG |
| | CATGAAAAATACGGGATACCTTACCTGTCGGCTCAGGTGTCGCCGAGTAC |
| | ACTGCTGAGTGCGCACCTGCCTCCGGTGCATCCTAAGTTTAACGTGCCTG |
| | AGCAGATGCCGCTGGCCATGAGAAAACTGCTGTGGAGATGCATAGAAAG |
| | ATTTAAGCTGGATAGAACGTGCGCTCCTGAGATAAACGCTGTGAGAAGA |
| | AAAGTGGGTCTGGAAACACCGGTGAAGAGAATATTTACGCAGTGGATGC |
| | ACTCGCCTCAGGGGGTGGTGTGCCTGTTTCCGGCCTGGTTTGCTCCTCCGC |
| | AGCAGGACTGGCCTCAGCCTCTGCACATGACAGGATTTCCTCTGTTTGAT |
| | GGAAGTATACCTGGTACGCCGCTGGACGATGAACTGCAGAGATTTCTGG |
| | ACCAGGGTTCGAGACCGCTGGTGTTTACACAGGGTAGTACGGAGCACCT |
| | GCAGGGGGATTTTTACGCGATGGCCCTGAGAGCCCTGGAAAGACTGGGT |
| | GCTAGAGGGATATTTCTGACAGGTGCTGGTCAGGAGCCTCTGAGAGGACT |
| | GCCTAACCACGTGCTGCAGAGAGCTTACGCGCCTCTGGGTGCTCTGCTGC |
| | CTAGTTGCGCTGGACTGGTGCATCCTGGGGGAATAGGAGCTATGAGTCTG |
| | GCCCTGGCCGCTGGGGTGCCTCAGGTGCTGCTGCCGTGCGCCCATGACCA |
| | GTTTGATAACGCTGAGAGACTTGTGAGACTGGGATGCGGTATGAGACTG |
| | GGTGTGCCGCTGAGAGAACAGGAGCTGAGAGGGGCGCTGTGGAGACTGC |
| | TGGAGGACCCTGCTATGGCCGCCGCCTGCAGAAGATTTATGGAACTGTCG |
| | CAGCCGCACAGTATAGCCTGCGGAAAAGCGGCCCAGGTGGTGGAAAGAT |
| | GCCATAGAGAGGGTGATGCTAGATGGCTGAAGGCTGCGTCGTAA (SEQ ID |
| | NO: 2) |
| rhlY | ATGAACACAGCCGTGGAACCTTACAAAGCCTCGTCGTTTGACCTGACACA |
| | CAAACTGACGGTGGAGAAGCACGGGCATACAGCTCTGATAACGATAAAC |
| | CATCCTCCGGCGAACACATGGGATAGAGACTCGCTGATAGGACTGAGAC |
| | AGCTGATAGAACACCTGAACAGAGACGATGACATATACGCTCTGGTGGT |
| | GACAGGACAGGGTCCTAAATTTTTCTCGGCGGGAGCCGATCTGAACATGT |
| | TTGCGGATGGTGACAAGGCTAGAGCGAGAGAAATGGCCAGAAGATTTG |
| | GAGAAGCGTTTGAGGCCCTGAGAGACTTTAGAGGTGTGTCGATAGCCGCT |
| | ATAAACGGGTACGCTATGGGAGGGGGACTGGAATGCGCCCTGGCTTGCG |
| | ATATAAGAATAGCGGAAAGACAGGCTCAGATGGCGCTGCCTGAAGCTGC |
| | TGTGGGACTGCTGCCTTGCGCTGGGGGAACACAGGCGCTGCCTTGGCTGG |
| | TGGGAGAGGGTTGGGCCAAGAGAATGATACTGTGCAACGAAAGAGTGGA |
| | CGCCGAGACGGCTCTGAGAATAGGTCTGGTGGAACAGGTGGTGGATAGT |
| | GGTGAAGCTAGAGGAGCTGCTCTGCTGCTGGCCGCTAAAGTGGCGAGAC |
| | AGAGTCCTGTGGCCATAAGAACAATAAAGCCGCTGATACAGGGTGCGAG |
| | AGAAAGAGCCCCTAACACGTGGCTGCCGGAAGAGAGAGAGAGATTTGTG |
| | GATCTGTTTGACGCCCAGGATACGAGAGAAGGGGTGAACGCTTTTCTGGA |
| | GAAAAGAGACCCGAAGTGGAGAAACTGCTAA (SEQ ID NO: 3) |
| rhlZ | ATGAACGTGCTGTTTGAAGAGAGACCTTCGCTGCACGGATTTAGAATAGG |
| | TATAGCTACACTGGACGCGGAAAAATCGCTGAACGCCCTGAGTCTGCCG |
| | ATGATAGAAGCTCTGGCCGCTAAGCTGGACGCTTGGGCGGAGGATGCCG |
| | GAATAGCTTGCGTGCTGCTGCGTGGTAACGGGGCCAAAGCCTTTTGCGCC |
| | GGGGGAGACGTGAGAAAGCTGGTGGATGCCTGCAGGGAGCAGCCTGGAG |
| | AGGTGCCGGCGCTGGCCAGAAGATTTTTCGCGGACGAATACAGACTGGA |
| | TTACAGAATACACACATACCCTAAACCGTTTATATGCTGGGCCCACGGGT |
| | ACGTGATGGGTGGGGGAATGGGTCTGATGCAGGGAGCCGGTATAAGAAT |
| | AGTGACGCCTTCGAGTAGACTGGCTATGCCGGAGATAGGGATAGGACTG |
| | TACCCTGACGTGGGGGCGTCGTGGTTTCTGGCCAGACTGCCGGGTAGACT |
| | GGGGCTGTTTCTGGGACTGAGTGCGGCCCAGATGAACGCGAGAGACGCC |
| | CTGGACCTGGATCTGGCCGATAGATTTCTGCTGGACGATCAGCAGGATGC |
| | TCTGCTGGCGGGTCTGGTGCAGATGAACTGGAACGAGTCGCCTCAGGTGC |
| | AGCTGCACAGTCTGCTGAGAGCTCTGGAACATGAGGCGAGAGGGGAACT |
| | GCCTGAGGCTCAGCTGCTGCCTAGAAGACCGAGACTGGACGCTCTGCTGG |
| | ACCAGCCTGATCTGGCTTCGGCTTGGCAGGCCCTGGTGGCTCTGAGAGAC |
| | GATGCTGATCCTCTGCTGGCGAGAGGTGCCAAGACACTGGCTGAAGGGT |
| | GCCCGATGACGGCGCATCTGGTGTGGCAGCAGATAGAGAGAGCGAGATA |
| | CCTGTCGCTGGCCGAAGTGTTTAGACTGGAGTACGCTATGAGTCTGAACT |
| | GCACAAGACACCCTGACTTTGCCGAAGGAGTGAGAGCTAGACTGATAGA |

TABLE 6-continued

| Codon-optimized nucleotide sequence | |
|---|---|
| Gene | Optimized nucleotide sequence |
| | CAGAGATAACGCGCCTAACTGGCATTGGCCGCAGGTGGAGAGTATACCG CAGGCCGTGATAGAAGCTCACTTTGAGCCTACATGGGAAGGAGAGCATC CGCTGGCCGGACTGTAA (SEQ ID NO: 4) |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A genetically modified methanotroph comprising one or more of enoyl-CoA hydratase/isomerase (RhlY and RhlZ), 3-hydroxyacyl-ACP-O-3 hydroxyacyltransferase (RhlA), or rhamnosyl transferase (RhlB), and one or more of the following mutations:

| #CHROM | POS | REF | ALT |
|---|---|---|---|
| NC 016112.1 | 257711 | T | C |
| NC 016112.1 | 274084 | A | C |
| NC 016112.1 | 274102 | A | G |
| NC 016112.1 | 274387 | C | T |
| NC 016112.1 | 274678 | T | C |
| NC 016112.1 | 274869 | C | T |
| NC 016112.1 | 275047 | T | C |
| NC 016112.1 | 275049 | G | A |

-continued

| #CHROM | POS | REF | ALT |
|---|---|---|---|
| NC 016112.1 | 275058 | C | T |
| NC 016112.1 | 275059 | G | T |
| NC 016112.1 | 275081 | C | T |
| NC 016112.1 | 275093 | C | T |
| NC 016112.1 | 275110 | T | C |
| NC 016112.1 | 278205 | C | G |
| NC 016112.1 | 278215 | A | G |
| NC 016112.1 | 278222 | T | G |
| NC 016112.1 | 278240 | G | A |
| NC 016112.1 | 278284 | G | A |
| NC 016112.1 | 278386 | G | A |
| NC 016112.1 | 278466 | G | T |
| NC 016112.1 | 278490 | A | G |
| NC 016112.1 | 278492 | T | C |
| NC 016112.1 | 278494 | G | T |

-continued

| #CHROM | POS | REF | ALT |
|---|---|---|---|
| NC 016112.1 | 278514 | T | A |
| NC 016112.1 | 278515 | C | G |
| NC 016112.1 | 278517 | C | T |
| NC 016112.1 | 278521 | G | A |
| NC 016112.1 | 278545 | A | G |
| NC 016112.1 | 279003 | A | G |
| NC 016112.1 | 279129 | C | T |
| NC 016112.1 | 279280 | G | T |
| NC 016112.1 | 279714 | T | C |
| NC 016112.1 | 279721 | T | C |
| NC 016112.1 | 279732 | C | G |
| NC 016112.1 | 280003 | A | C |
| NC 016112.1 | 280038 | T | C |
| NC 016112.1 | 280048 | A | G |
| NC 016112.1 | 280050 | T | C |
| NC 016112.1 | 280053 | C | T |
| NC 016112.1 | 280077 | C | T |
| NC 016112.1 | 280080 | G | A |
| NC 016112.1 | 280256 | G | A |
| NC 016112.1 | 280275 | T | C |
| NC 016112.1 | 280293 | T | C |
| NC 016112.1 | 280317 | C | A |
| NC 016112.1 | 280322 | A | G |
| NC 016112.1 | 280378 | T | C |
| NC 016112.1 | 280393 | C | G |
| NC 016112.1 | 280402 | T | C |
| NC 016112.1 | 280495 | T | C |
| NC 016112.1 | 280585 | T | C |
| NC 016112.1 | 280588 | A | C |
| NC 016112.1 | 280630 | A | G |
| NC 016112.1 | 280681 | C | A |
| NC 016112.1 | 280705 | C | T |
| NC 016112.1 | 280708 | T | C |
| NC 016112.1 | 280711 | C | T |
| NC 016112.1 | 280714 | G | T |
| NC 016112.1 | 280717 | T | C |
| NC 016112.1 | 280729 | T | C |
| NC 016112.1 | 280731 | T | C |
| NC 016112.1 | 280754 | C | T |
| NC 016112.1 | 280825 | T | G |
| NC 016112.1 | 280885 | C | T |
| NC 016112.1 | 280913 | A | G |
| NC 016112.1 | 280914 | T | C |
| NC 016112.1 | 280936 | C | A |
| NC 016112.1 | 280957 | T | C |
| NC 016112.1 | 281142 | A | G |
| NC 016112.1 | 281323 | G | A |
| NC 016112.1 | 281338 | A | G |
| NC 016112.1 | 281353 | A | G |
| NC 016112.1 | 281461 | T | A |
| NC 016112.1 | 281638 | C | T |
| NC 016112.1 | 282166 | C | A |
| NC 016112.1 | 282168 | G | A |
| NC 016112.1 | 282169 | C | T |
| NC 016112.1 | 282235 | A | T |
| NC 016112.1 | 282262 | A | T |
| NC 016112.1 | 282400 | C | T |
| NC 016112.1 | 282479 | T | C |
| NC 016112.1 | 282486 | C | T |
| NC 016112.1 | 282727 | C | T |
| NC 016112.1 | 282835 | T | C |
| NC 016112.1 | 282955 | C | T |
| NC 016112.1 | 282965 | T | C |
| NC 016112.1 | 282967 | G | A |
| NC 016112.1 | 283006 | A | C |
| NC 016112.1 | 283043 | A | T |
| NC 016112.1 | 283077 | G | T |
| NC 016112.1 | 283164 | G | A |
| NC 016112.1 | 283170 | A | G |
| NC 016112.1 | 283173 | G | C |
| NC 016112.1 | 283185 | G | A |
| NC 016112.1 | 283216 | T | C |
| NC 016112.1 | 283236 | A | T |
| NC 016112.1 | 283248 | C | T |
| NC 016112.1 | 283275 | G | A |
| NC 016112.1 | 283278 | C | T |
| NC 016112.1 | 283336 | C | T |

-continued

| #CHROM | POS | REF | ALT |
|---|---|---|---|
| NC 016112.1 | 283365 | G | C |
| NC 016112.1 | 283389 | G | A |
| NC 016112.1 | 283395 | C | T |
| NC 016112.1 | 283440 | T | C |
| NC 016112.1 | 283458 | T | C |
| NC 016112.1 | 283461 | T | C |
| NC 016112.1 | 283503 | C | T |
| NC 016112.1 | 283533 | A | C |
| NC 016112.1 | 283572 | G | A |
| NC 016112.1 | 283578 | C | T |
| NC 016112.1 | 283629 | T | C |
| NC 016112.1 | 283641 | G | T |
| NC 016112.1 | 283647 | C | T |
| NC 016112.1 | 283792 | A | G |
| NC 016112.1 | 283869 | A | G |
| NC 016112.1 | 283893 | T | C |
| NC 016112.1 | 283920 | A | C |
| NC 016112.1 | 283934 | G | A |
| NC 016112.1 | 283953 | A | G |
| NC 016112.1 | 283974 | T | C |
| NC 016112.1 | 284034 | T | C |
| NC 016112.1 | 284040 | C | T |
| NC 016112.1 | 284046 | G | A |
| NC 016112.1 | 284103 | A | G |
| NC 016112.1 | 284107 | G | A |
| NC 016112.1 | 284273 | T | C |
| NC 016112.1 | 284392 | C | G |
| NC 016112.1 | 284394 | G | A |
| NC 016112.1 | 284395 | G | C |
| NC 016112.1 | 284399 | G | A |
| NC 016112.1 | 284404 | C | T |
| NC 016112.1 | 284407 | G | A |
| NC 016112.1 | 284534 | A | C |
| NC 016112.1 | 284560 | C | A |
| NC 016112.1 | 284571 | G | C |
| NC 016112.1 | 284605 | G | T |
| NC 016112.1 | 284710 | C | T |
| NC 016112.1 | 284748 | C | T |
| NC 016112.1 | 284829 | A | G |
| NC 016112.1 | 284833 | A | G |
| NC 016112.1 | 284857 | G | A |
| NC 016112.1 | 284860 | C | T |
| NC 016112.1 | 284866 | C | T |
| NC 016112.1 | 284869 | A | G |
| NC 016112.1 | 284870 | A | C |
| NC 016112.1 | 284872 | G | A |
| NC 016112.1 | 284909 | G | A |
| NC 016112.1 | 284912 | G | A |
| NC 016112.1 | 284924 | C | T |
| NC 016112.1 | 284926 | G | T |
| NC 016112.1 | 284935 | G | A |
| NC 016112.1 | 284943 | G | A |
| NC 016112.1 | 284983 | A | C |
| NC 016112.1 | 284987 | C | T |
| NC 016112.1 | 284989 | A | G |
| NC 016112.1 | 285002 | C | T |
| NC 016112.1 | 285006 | A | G |
| NC 016112.1 | 285007 | A | C |
| NC 016112.1 | 285010 | T | G |
| NC 016112.1 | 285011 | C | T |
| NC 016112.1 | 285019 | T | G |
| NC 016112.1 | 285020 | A | G |
| NC 016112.1 | 285023 | A | G |
| NC 016112.1 | 285033 | G | A |
| NC 016112.1 | 285053 | T | A |
| NC 016112.1 | 285058 | G | C |
| NC 016112.1 | 285062 | C | T |
| NC 016112.1 | 285068 | T | G |
| NC 016112.1 | 285069 | C | T |
| NC 016112.1 | 285076 | G | A |
| NC 016112.1 | 285088 | T | C |
| NC 016112.1 | 285091 | A | G |
| NC 016112.1 | 285092 | C | T |
| NC 016112.1 | 285095 | A | G |
| NC 016112.1 | 285100 | T | A |
| NC 016112.1 | 285109 | G | T |
| NC 016112.1 | 285114 | T | C |

-continued

| #CHROM | POS | REF | ALT |
|---|---|---|---|
| NC 016112.1 | 285115 | T | C |
| NC 016112.1 | 285118 | A | G |
| NC 016112.1 | 285153 | G | A |
| NC 016112.1 | 503932 | A | G |
| NC 016112.1 | 503936 | T | C |
| NC 016112.1 | 503940 | G | A |
| NC 016112.1 | 503945 | A | G |
| NC 016112.1 | 503949 | A | C |
| NC 016112.1 | 503970 | C | T |
| NC 016112.1 | 503972 | G | A |
| NC 016112.1 | 503979 | A | G |
| NC 016112.1 | 504062 | C | A |
| NC 016112.1 | 504071 | A | G |
| NC 016112.1 | 504073 | T | A |
| NC 016112.1 | 504091 | C | G |
| NC 016112.1 | 504109 | T | C |
| NC 016112.1 | 504856 | A | T |
| NC 016112.1 | 504907 | C | T |
| NC 016112.1 | 538607 | G | C |
| NC 016112.1 | 705301 | C | G |
| NC 016112.1 | 790204 | G | A |
| NC 016112.1 | 1075721 | C | A |
| NC 016112.1 | 1116663 | C | G |
| NC 016112.1 | 1116664 | G | C |
| NC 016112.1 | 1330008 | G | T |
| NC 016112.1 | 1330095 | A | G |
| NC 016112.1 | 1393728 | C | T |
| NC 016112.1 | 1419041 | T | C |
| NC 016112.1 | 1439362 | C | A |
| NC 016112.1 | 1479855 | T | C |
| NC 016112.1 | 1480356 | C | T |
| NC 016112.1 | 1593190 | T | A |
| NC 016112.1 | 1593227 | A | G |
| NC 016112.1 | 1593247 | G | A |
| NC 016112.1 | 1593316 | G | A |
| NC 016112.1 | 1593337 | T | C |
| NC 016112.1 | 1593340 | G | A |
| NC 016112.1 | 1593353 | T | C |
| NC 016112.1 | 1593360 | C | T |
| NC 016112.1 | 1593364 | C | T |
| NC 016112.1 | 1593444 | T | G |
| NC 016112.1 | 1593445 | T | G |
| NC 016112.1 | 1593520 | G | A |
| NC 016112.1 | 1593525 | G | A |
| NC 016112.1 | 1593540 | T | G |
| NC 016112.1 | 1593565 | G | A |
| NC 016112.1 | 1593577 | T | C |
| NC 016112.1 | 1593583 | T | C |
| NC 016112.1 | 1593586 | C | T |
| NC 016112.1 | 1593589 | C | G |
| NC 016112.1 | 1593595 | G | A |
| NC 016112.1 | 1593598 | A | G |
| NC 016112.1 | 1593612 | T | C |
| NC 016112.1 | 1593613 | G | A |
| NC 016112.1 | 1593633 | A | G |
| NC 016112.1 | 1593634 | T | C |
| NC 016112.1 | 1593639 | A | T |
| NC 016112.1 | 1593641 | A | G |
| NC 016112.1 | 1593644 | C | A |
| NC 016112.1 | 1593645 | G | A |
| NC 016112.1 | 1593652 | C | A |
| NC 016112.1 | 1593669 | G | A |
| NC 016112.1 | 1593683 | C | T |
| NC 016112.1 | 1594017 | A | G |
| NC 016112.1 | 1594020 | G | A |
| NC 016112.1 | 1594023 | A | G |
| NC 016112.1 | 1594053 | G | T |
| NC 016112.1 | 1594054 | T | G |
| NC 016112.1 | 1594125 | C | T |
| NC 016112.1 | 1594206 | C | T |
| NC 016112.1 | 1594314 | C | T |
| NC 016112.1 | 1594377 | C | A |
| NC 016112.1 | 1594425 | C | T |
| NC 016112.1 | 1594428 | C | A |
| NC 016112.1 | 1594434 | G | T |
| NC 016112.1 | 1594479 | T | G |
| NC 016112.1 | 1594518 | C | T |

-continued

| #CHROM | POS | REF | ALT |
|---|---|---|---|
| NC 016112.1 | 1594520 | T | G |
| NC 016112.1 | 1594524 | A | G |
| NC 016112.1 | 1594549 | T | C |
| NC 016112.1 | 1594575 | C | T |
| NC 016112.1 | 1594578 | G | A |
| NC 016112.1 | 1594602 | T | C |
| NC 016112.1 | 1594612 | C | G |
| NC 016112.1 | 1594656 | C | G |
| NC 016112.1 | 1594662 | C | T |
| NC 016112.1 | 1594683 | A | T |
| NC 016112.1 | 1594701 | G | C |
| NC 016112.1 | 1594704 | A | C |
| NC 016112.1 | 1594710 | T | C |
| NC 016112.1 | 1594713 | C | T |
| NC 016112.1 | 1594728 | A | G |
| NC 016112.1 | 1594732 | G | A |
| NC 016112.1 | 1594734 | G | C |
| NC 016112.1 | 1594769 | T | C |
| NC 016112.1 | 1594793 | A | G |
| NC 016112.1 | 1594809 | G | A |
| NC 016112.1 | 1594815 | G | A |
| NC 016112.1 | 1594819 | C | T |
| NC 016112.1 | 1594821 | G | C |
| NC 016112.1 | 1594830 | T | A |
| NC 016112.1 | 1594863 | C | T |
| NC 016112.1 | 1594870 | G | A |
| NC 016112.1 | 1595111 | G | A |
| NC 016112.1 | 1595177 | G | A |
| NC 016112.1 | 1595180 | A | G |
| NC 016112.1 | 1595273 | T | C |
| NC 016112.1 | 1595315 | A | C |
| NC 016112.1 | 1595342 | A | C |
| NC 016112.1 | 1595354 | G | A |
| NC 016112.1 | 1595360 | T | C |
| NC 016112.1 | 1595384 | A | G |
| NC 016112.1 | 1595426 | C | T |
| NC 016112.1 | 1595429 | G | A |
| NC 016112.1 | 1595432 | C | T |
| NC 016112.1 | 1595435 | A | G |
| NC 016112.1 | 1595453 | G | A |
| NC 016112.1 | 1595454 | C | A |
| NC 016112.1 | 1595504 | T | A |
| NC 016112.1 | 1595546 | G | A |
| NC 016112.1 | 1595567 | G | A |
| NC 016112.1 | 1595627 | C | T |
| NC 016112.1 | 1595651 | C | T |
| NC 016112.1 | 1598357 | T | C |
| NC 016112.1 | 1598396 | G | A |
| NC 016112.1 | 1598399 | A | G |
| NC 016112.1 | 1598434 | G | T |
| NC 016112.1 | 1598435 | G | A |
| NC 016112.1 | 1598477 | A | G |
| NC 016112.1 | 1598486 | A | G |
| NC 016112.1 | 1598507 | C | T |
| NC 016112.1 | 1598528 | C | T |
| NC 016112.1 | 1598531 | T | C |
| NC 016112.1 | 1598567 | G | A |
| NC 016112.1 | 1598579 | G | C |
| NC 016112.1 | 1598582 | C | A |
| NC 016112.1 | 1598606 | T | C |
| NC 016112.1 | 1598618 | G | T |
| NC 016112.1 | 1598627 | G | A |
| NC 016112.1 | 1598639 | A | G |
| NC 016112.1 | 1598642 | G | A |
| NC 016112.1 | 1598645 | G | A |
| NC 016112.1 | 1598657 | G | A |
| NC 016112.1 | 1598689 | A | G |
| NC 016112.1 | 1598696 | A | C |
| NC 016112.1 | 1598702 | G | A |
| NC 016112.1 | 1598717 | C | T |
| NC 016112.1 | 1598780 | T | C |
| NC 016112.1 | 1598789 | A | G |
| NC 016112.1 | 1598852 | A | G |
| NC 016112.1 | 1598870 | A | T |
| NC 016112.1 | 1598939 | G | C |
| NC 016112.1 | 1599023 | G | T |
| NC 016112.1 | 1599026 | T | C |

-continued

| #CHROM | POS | REF | ALT |
|---|---|---|---|
| NC 016112.1 | 1599035 | G | A |
| NC 016112.1 | 1599038 | C | G |
| NC 016112.1 | 1599053 | G | A |
| NC 016112.1 | 1599104 | C | T |
| NC 016112.1 | 1599140 | A | G |
| NC 016112.1 | 1599181 | T | C |
| NC 016112.1 | 1599182 | T | G |
| NC 016112.1 | 1599201 | A | G |
| NC 016112.1 | 1599206 | C | T |
| NC 016112.1 | 1599210 | G | C |
| NC 016112.1 | 1599216 | A | C |
| NC 016112.1 | 1599217 | T | C |
| NC 016112.1 | 1599227 | A | T |
| NC 016112.1 | 1815912 | G | C |
| NC 016112.1 | 2028111 | C | T |
| NC 016112.1 | 2637141 | T | C |
| NC 016112.1 | 2637145 | C | T |
| NC 016112.1 | 2637153 | G | A |
| NC 016112.1 | 2674948 | A | G |
| NC 016112.1 | 2674956 | A | G |
| NC 016112.1 | 2674965 | T | G |
| NC 016112.1 | 2674967 | A | G |
| NC 016112.1 | 2674973 | T | C |
| NC 016112.1 | 2675002 | A | G |
| NC 016112.1 | 2675003 | T | G |
| NC 016112.1 | 2675021 | A | G |
| NC 016112.1 | 2675077 | A | G |
| NC 016112.1 | 2675094 | G | A |
| NC 016112.1 | 2703406 | C | G |
| NC 016112.1 | 2703409 | A | G |
| NC 016112.1 | 3190412 | T | C |
| NC 016112.1 | 3190432 | G | A |
| NC 016112.1 | 3190464 | T | C |
| NC 016112.1 | 3797919 | C | T |
| NC 016112.1 | 3798246 | T | C |
| NC 016112.1 | 3798385 | A | G |
| NC 016112.1 | 3798455 | C | G |
| NC 016112.1 | 3798478 | A | C |
| NC 016112.1 | 3798479 | T | C |
| NC 016112.1 | 3798503 | T | C |
| NC 016112.1 | 4222340 | T | G |
| NC 016112.1 | 4222349 | A | C |
| NC 016112.1 | 4233436 | G | T |
| NC 016112.1 | 4233466 | G | A |
| NC 016112.1 | 4233475 | A | G |
| NC 016112.1 | 4233780 | C | T |
| NC 016112.1 | 4233854 | T | C |
| NC 016112.1 | 4239364 | A | G |
| NC 016112.1 | 4239375 | T | G |
| NC 016112.1 | 4239378 | A | G |
| NC 016112.1 | 4249077 | T | C |
| NC 016112.1 | 4249101 | A | T |
| NC 016112.1 | 4249149 | T | C |
| NC 016112.1 | 4249152 | A | G |
| NC 016112.1 | 4249185 | A | G |
| NC 016112.1 | 4249212 | C | T |
| NC 016112.1 | 4249287 | A | T |
| NC 016112.1 | 4249322 | C | T |
| NC 016112.1 | 4249335 | A | G |
| NC 016112.1 | 4249392 | G | A |
| NC 016112.1 | 4249608 | T | C |
| NC 016112.1 | 4249620 | G | T |
| NC 016112.1 | 4249623 | T | C |
| NC 016112.1 | 4249634 | A | G |
| NC 016112.1 | 4249635 | A | G |
| NC 016112.1 | 4249670 | A | G |
| NC 016112.1 | 4249692 | C | T |
| NC 016112.1 | 4249695 | C | T |
| NC 016112.1 | 4249717 | C | T |
| NC 016112.1 | 4249809 | T | C |
| NC 016112.1 | 4249824 | G | A |
| NC 016112.1 | 4249842 | T | C |
| NC 016112.1 | 4249845 | C | G |
| NC 016112.1 | 4249860 | T | C |
| NC 016112.1 | 4249874 | T | C |
| NC 016112.1 | 4249883 | A | G |
| NC 016112.1 | 4249893 | C | T |

-continued

| #CHROM | POS | REF | ALT |
|---|---|---|---|
| NC 016112.1 | 4249902 | T | C |
| NC 016112.1 | 4249908 | A | G |
| NC 016112.1 | 4249911 | A | G |
| NC 016112.1 | 4249912 | A | C |
| NC 016112.1 | 4249914 | C | T |
| NC 016112.1 | 4249917 | A | G |
| NC 016112.1 | 4249926 | T | C |
| NC 016112.1 | 4249986 | A | G |
| NC 016112.1 | 4250010 | T | C |
| NC 016112.1 | 4250103 | G | A |
| NC 016112.1 | 4250110 | A | C |
| NC 016112.1 | 4250113 | C | T |
| NC 016112.1 | 4250115 | T | C |
| NC 016112.1 | 4250119 | T | A |
| NC 016112.1 | 4250142 | A | G |
| NC 016112.1 | 4250148 | T | C |
| NC 016112.1 | 4250154 | G | A |
| NC 016112.1 | 4250157 | G | A |
| NC 016112.1 | 4250166 | C | T |
| NC 016112.1 | 4250169 | C | T |
| NC 016112.1 | 4250172 | G | A |
| NC 016112.1 | 4250199 | T | C |
| NC 016112.1 | 4250200 | T | G |
| NC 016112.1 | 4250205 | T | C |
| NC 016112.1 | 4250235 | G | A |
| NC 016112.1 | 4250253 | T | G |
| NC 016112.1 | 4250319 | G | A |
| NC 016112.1 | 4250546 | G | A |
| NC 016112.1 | 4250584 | T | C |
| NC 016112.1 | 4250678 | C | T |
| NC 016112.1 | 4250712 | A | T |
| NC 016112.1 | 4250808 | A | G |
| NC 016112.1 | 4250821 | C | T |
| NC 016112.1 | 4250837 | G | C |
| NC 016112.1 | 4250863 | T | A |
| NC 016112.1 | 4250879 | A | G |
| NC 016112.1 | 4250924 | A | G |
| NC 016112.1 | 4255137 | C | T |
| NC 016112.1 | 4255200 | C | T |
| NC 016112.1 | 4258918 | T | A |
| NC 016112.1 | 4258932 | A | G |
| NC 016112.1 | 4258938 | G | A |
| NC 016112.1 | 4258963 | A | T |
| NC 016112.1 | 4258972 | C | T |
| NC 016112.1 | 4259013 | A | G |
| NC 016112.1 | 4259401 | C | T |
| NC 016112.1 | 4259421 | T | C |
| NC 016112.1 | 4259727 | T | C |
| NC 016112.1 | 4262921 | A | G |
| NC 016112.1 | 4262948 | A | G |
| NC 016112.1 | 4263098 | C | T |
| NC 016112.1 | 4263149 | G | T |
| NC 016112.1 | 4263405 | T | G |
| NC 016112.1 | 4263776 | T | A |
| NC 016112.1 | 4263947 | C | G |
| NC 016112.1 | 4263958 | T | C |
| NC 016112.1 | 4263968 | C | T |
| NC 016112.1 | 4263979 | A | G |
| NC 016112.1 | 4270962 | C | T |
| NC 016112.1 | 4270965 | A | G |
| NC 016112.1 | 4270968 | T | C |
| NC 016112.1 | 4271667 | C | A |
| NC 016112.1 | 4271679 | C | G |
| NC 016112.1 | 4271701 | T | A |
| NC 016112.1 | 4428308 | G | C |
| NC 016112.1 | 4552963 | T | C |
| NC 016112.1 | 4553104 | G | A |
| NC 016112.1 | 4553506 | C | T |
| NC 016112.1 | 4553743 | A | G |
| NC 016112.1 | 4554354 | T | C |
| NC 016108.1 | 128058 | G | C; |

wherein the genetically modified methanotroph is a Methylotuvimicrobium cell.

2. The genetically modified methanotroph of claim 1, wherein the Methylotuvimicrobium cell is Methylotuvimicrobium buryatense or Methylotuvimicrobium alcaliphilum (syn. Methylomicrobium alcaliphilum).

3. The genetically modified methanotroph of claim 2, wherein the methanotroph is Methylotuvimicrobium alcaliphilum (syn. Methylomicrobium alcaliphilum).

4. The genetically modified methanotroph of claim 1, wherein methanotroph comprises mutations in one or more of the following genes: fabG, murA, dxs, tssJ, and tkt.

5. The genetically modified methanotroph of claim 1, wherein methanotroph comprises mutations in the genes of one or more, or all, of the following: IS3 family transposase (gene-MEALZ_RS03460, gene-MEALZ_RS08615, gene-MEALZ_RS11580); autotransporter outer membrane beta-barrel domain-containing protein (gene-MEALZ_RS22650); Crp/Fnr family transcriptional regulator (gene-MEALZ_RS12360); multicopper oxidase domain-containing protein (gene-MEALZ_RS14455); type IV pilus secretin PilQ (pilQ; gene-MEALZ_RS15795); and, FAD-dependent oxidoreductase/hypothetical protein/NAD (P)/FAD-dependent oxidoreductase (gene-MEALZ_RS18045).

6. The genetically modified methanotroph of claim 1, wherein the host cell or methanotroph in its unmodified form is sensitive, or unable to grow, in a medium having rhamnolipid at a concentration equal to or more than about 0.05 g/L.

7. The genetically modified methanotroph of claim 1, wherein the genetically modified host cell or methanotroph is resistant, or able to grow, in a medium having rhamnolipid at a concentration equal to or less than about 5.0 g/L.

8. The genetically modified methanotroph of claim 1, wherein the genetically modified host cell or methanotroph is capable of producing more rhamnolipid or fatty acids than the host cell or methanotroph in its unmodified form.

9. The genetically modified methanotroph of claim 1, wherein the RhlY, RhlZ, RhlA, and RhlB are *Pseudomonas aeruginosa* RhlY, RhlZ, RhlA, and RhlB.

* * * * *

SEQUENCE LISTING

```
Sequence total quantity: 26
SEQ ID NO: 1           moltype = AA  length = 888
FEATURE                Location/Qualifiers
source                 1..888
                       mol_type = protein
                       organism = synthetic construct
SEQUENCE: 1
ATGAGAAGAG AATCGCTGCT TGTGAGTGTG TGCAAAGGAC TGAGAGTGCA CGTGGAGAGA  60
GTGGGACAGG ACCCTGGTAG ATCGACAGTG ATGCTGGTGA ACGGTGCTAT GGCGACAACG  120
GCTAGTTTTG CGAGAACGTG CAAATGCCTG GCTGAACACT TTAACGTGGT GCTGTTTGAT  180
CTGCCTTTTG CGGGACAGTC GAGACAGCAT AACCCGCAGA GAGGTCTGAT AACAAAGGAC  240
GATGAAGTGG AGATACTGCT GGCCCTGATA GAAAGATTTG AGGTGAACCA TCTGGTGTCG  300
GCGAGTTGGG GAGGGATAAG TACGCTGCTG GCCCTGAGTA GAAACCCTAG AGGGATAAGA  360
TCGAGTGTGG TGATGGCCTT TGCTCCGGGG CTGAACCAGG CTATGCTGGA CTACGTGGGA  420
AGAGCGCAGG CCCTGATAGA ACTGGACGAT AAGAGTGCGA TAGGTCACCT GCTGAACGAG  480
ACAGTGGGGA AATACCTGCC TCAGAGACTG AAGGCGTCGA ACCACCAGCA CATGGCCAGT  540
CTGGCTACGG GAGAATACGA GCAGGCCAGA TTTCATATAG ACCAGGTGCT GGCCCTGAAC  600
GATAGAGGTT ACCTGGCTTG CCTGGAGAGA ATACAGTCGC ACGTGCATTT TATAAACGGG  660
AGTTGGGACG AATACACAAC GGCGGAGGAC GCCAGACAGT TTAGAGATTA CCTGCCGCAC  720
TGCTCGTTTA GTAGAGTGGA AGGTACAGGG CATTTTCTGG ATCTGGAGTC GAAACTGGCC  780
GCTGTGAGAG TGCACAGAGC CCTGCTGGAA CATCTGCTGA AGCAGCCTGA ACCGCAGAGA  840
GCTGAGAGAG CGGCCGGGTT TCACGAGATG GCTATAGGAT ACGCGTAA               888

SEQ ID NO: 2           moltype = AA  length = 1281
FEATURE                Location/Qualifiers
source                 1..1281
                       mol_type = protein
                       organism = synthetic construct
SEQUENCE: 2
ATGCACGCGA TACTGATAGC CATAGGGTCG GCTGGAGACG TGTTTCCTTT TATAGGGCTG  60
GCTAGAACAC TGAAACTGAG AGGACACAGA GTGAGTCTGT GCACGATACC TGTGTTTAGA  120
GACGCTGTGG AGCAGCATGG GATAGCGTTT GTGCCGCTGT CGGATGAACT GACATACAGA  180
AGAACGATGG GAGACCCTAG ACTGTGGGAC CCTAAGACAA GTTTTGGAGT GCTGTGGCAG  240
GCCATAGCTG GTATGATAGA ACCTGTGTAC GAGTACGTGT CGGCGCAGAG ACACGACGAT  300
ATAGTGGTGG TGGGGAGTCT GTGGGCTCTG GGAGCTAGAA TAGCGCATGA AAAATACGGG  360
ATACCTTACC TGTCGGCTCA GGTGTCGCCG AGTACACTGC TGAGTGCGCA CCTGCCTCCG  420
GTGCATCCTA AGTTTAACGT GCCTGAGCAG ATGCCGCTGG CCATGAGAAA ACTGCTGTGG  480
AGATGCATAG AAAGATTTAA GCTGGATAGA ACGTGCGCTC CTGAGATAAA CGCTGTGAGA  540
AGAAAAGTGG GTCTGGAAAC ACCGGTGAAG AGAATATTTA CGCAGTGGAT GCACTCGCCT  600
CAGGGGGTGG TGTGCCTGTT TCCGGCCTGG TTTGCTCCTC CGCAGCAGGA CTGGCCTCAG  660
CCTCTGCACA TGACAGGATT TCCTCTGTTT GATGGAAGTA TACCTGGTAC GCCGCTGGAC  720
GATGAACTGC AGAGATTTCT GGACCAGGGT TCGAGACCGC TGGTGTTTAC ACAGGGTAGT  780
ACGGAGCACC TGCAGGGGGA TTTTTACGCG ATGGCCCTGA GAGCCCTGGA AAGACTGGGT  840
GCTAGAGGGA TATTTCTGAC AGGTGCTGGT CAGGAGCCTC TGAGAGGACT GCCTAACCAC  900
GTGCTGCAGA GAGCTTACGC GCCTCTGGGT GCTCTGCTGC CTAGTTGCGC TGGACTGGTG  960
CATCCTGGGG GAATAGGAGC TATGAGTCTG GCCCTGGCCG CTGGGGTGCC TCAGGTGCTG  1020
CTGCCGTGCG CCCATGACCA GTTTGATAAC GCTGAGAGAC TTGTGAGACT GGGATGCGGT  1080
ATGAGACTGG GTGTGCCGCT GAGAGAACAG GAGCTGAGAG GGGCGCTGTG GAGACTGCTG  1140
GAGGACCCTG CTATGGCCGC CGCCTGCAGA AGATTTATGG AACTGTCGCA GCCGCACAGT  1200
ATAGCCTGCG GAAAAGCGGC CCAGGTGGTG GAAAGATGCC ATAGAGAGGG TGATGCTAGA  1260
TGGCTGAAGG CTGCGTCGTA A                                           1281

SEQ ID NO: 3           moltype = AA  length = 819
FEATURE                Location/Qualifiers
source                 1..819
                       mol_type = protein
                       organism = synthetic construct
SEQUENCE: 3
ATGAACACAG CCGTGGAACC TTACAAAGCC TCGTCGTTTG ACCTGACACA CAAACTGACG  60
```

-continued

```
GTGGAGAAGC ACGGGCATAC AGCTCTGATA ACGATAAACC ATCCTCCGGC GAACACATGG  120
GATAGAGACT CGCTGATAGG ACTGAGACAG CTGATAGAAC ACCTGAACAG AGACGATGAC  180
ATATACGCTC TGGTGGTGAC AGGACAGGGT CCTAAATTTT TCTCGGCGGG AGCCGATCTG  240
AACATGTTTG CGGATGGTGA CAAGGCTAGA GCGAGAGAAA TGGCCAGAAG ATTTGGAGAA  300
GCGTTTGAGG CCCTGAGAGA CTTTAGAGGT GTGTCGATAG CCGCTATAAA CGGGTACGCT  360
ATGGGAGGGG GACTGGAATG CGCCCTGGCT TGCGATATAA GAATAGCGGA AAGACAGGCT  420
CAGATGGCGC TGCCTGAAGC TGCTGTGGGA CTGCTGCCTT GCGCTGGGGG AACACAGGCG  480
CTGCCTTGGC TGGTGGGAGA GGGTTGGGCC AAGAGAATGA TACTGTGCAA CGAAAGAGTG  540
GACGCCGAGA CGGCTCTGAG AATAGGTCTG GTGGAACAGG TGGTGGATAG TGGTGAAGCT  600
AGAGGAGCTG CTCTGCTGCT GGCCGCTAAA GTGGCGAGAC AGAGTCCTGT GGCCATAAGA  660
ACAATAAAGC CGCTGATACA GGGTGCGAGA GAAAGAGCCC CTAACACGTG GCTGCCGGAA  720
GAGAGAGAGA GATTTGTGGA TCTGTTTGAC GCCCAGGATA CGAGAGAAGG GGTGAACGCT  780
TTTCTGGAGA AAAGAGACCC GAAGTGGAGA AACTGCTAA                         819

SEQ ID NO: 4           moltype = AA  length = 1104
FEATURE                Location/Qualifiers
source                 1..1104
                       mol_type = protein
                       organism = synthetic construct
SEQUENCE: 4
ATGAACGTGC TGTTTGAAGA GAGACCTTCG CTGCACGGAT TTAGAATAGG TATAGCTACA  60
CTGGACGCGG AAAAATCGCT GAACGCCCTG AGTCTGCCGA TGATAGAAGC TCTGGCCGCT  120
AAGCTGGACG CTTGGGCGGA GGATGCCGGA ATAGCTTGCG TGCTGCTGCG TGGTAACGGG  180
GCCAAAGCCT TTTGCGCCGG GGGAGACGTG AGAAAGCTGG TGGATGCCTG CAGGGAGCAG  240
CCTGGAGAGG TGCCGGCGCT GGCCAGAAGA TTTTTCGCGG ACGAATACAG ACTGGATTAC  300
AGAATACACA CATACCCTAA ACCGTTTATA TGCTGGGCCC ACGGGTACGT GATGGGTGGG  360
GGAATGGGTC TGATGCAGGG AGCCGGTATA AGAATAGTGA CGCCTTCGAG TAGACTGGCT  420
ATGCCGGAGA TAGGGATAGG ACTGTACCCT GACGTGGGGG CGTCGTGGTT TCTGGCCAGA  480
CTGCCGGGTA GACTGGGGCT GTTTCTGGGA CTGAGTGCGG CCCAGATGAA CGCGAGAGAC  540
GCCCTGGACC TGGATCTGGC CGATAGATTT CTGCTGGACG ATCAGCAGGA TGCTCTGCTG  600
GCGGGTCTGG TGCAGATGAA CTGGAACGAG TCGCCTCAGG TGCAGCTGCA CAGTCTGCTG  660
AGAGCTCTGG AACATGAGGC GAGAGGGGAA CTGCCTGAGG CTCAGCTGCT GCCTAGAAGA  720
CCGAGACTGG ACGCTCTGCT GGACCAGCCT GATCTGGCTT CGGCTTGGCA GGCCCTGGTG  780
GCTCTGAGAG ACGATGCTGA TCCTCTGCTG GCGAGAGGTG CCAAGACACT GGCTGAAGGG  840
TGCCCGATGA CGGCGCATCT GGTGTGGCAG CAGATAGAGA GAGCGAGATA CCTGTCGCTG  900
GCCGAAGTGT TTAGACTGGA GTACGCTATG AGTCTGAACT GCACAAGACA CCCTGACTTT  960
GCCGAAGGAG TGAGAGCTAG ACTGATAGAC AGAGATAACG CGCCTAACTG GCATTGGCCG  1020
CAGGTGGAGA GTATACCGCA GGCCGTGATA GAAGCTCACT TTGAGCCTAC ATGGGAAGGA  1080
GAGCATCCGC TGGCCGGACT GTAA                                         1104

SEQ ID NO: 5           moltype = DNA  length = 28
FEATURE                Location/Qualifiers
source                 1..28
                       mol_type = other DNA
                       organism = synthetic construct
SEQUENCE: 5
cgcacatatg agaagagaat cgctgctt                                     28

SEQ ID NO: 6           moltype = DNA  length = 39
FEATURE                Location/Qualifiers
source                 1..39
                       mol_type = other DNA
                       organism = synthetic construct
SEQUENCE: 6
ttacggatcc gctagcttac gcgtatccta tagccatct                         39

SEQ ID NO: 7           moltype = DNA  length = 31
FEATURE                Location/Qualifiers
source                 1..31
                       mol_type = other DNA
                       organism = synthetic construct
SEQUENCE: 7
ggcacatatg cacgcgatac tgatagccat a                                 31

SEQ ID NO: 8           moltype = DNA  length = 38
FEATURE                Location/Qualifiers
source                 1..38
                       mol_type = other DNA
                       organism = synthetic construct
SEQUENCE: 8
ctatggatcc gctagcttac gacgcagcct tcagccat                          38

SEQ ID NO: 9           moltype = DNA  length = 30
FEATURE                Location/Qualifiers
source                 1..30
                       mol_type = other DNA
                       organism = synthetic construct
SEQUENCE: 9
cgcacatatg aacacagccg tggaacctta                                   30
```

```
SEQ ID NO: 10          moltype = DNA  length = 42
FEATURE                Location/Qualifiers
source                 1..42
                       mol_type = other DNA
                       organism = synthetic construct
SEQUENCE: 10
ctatggatcc gctagcttag cagtttctcc acttcgggtc tc                          42

SEQ ID NO: 11          moltype = DNA  length = 29
FEATURE                Location/Qualifiers
source                 1..29
                       mol_type = other DNA
                       organism = synthetic construct
SEQUENCE: 11
ggcacatatg aacgtgctgt ttgaagaga                                         29

SEQ ID NO: 12          moltype = DNA  length = 39
FEATURE                Location/Qualifiers
source                 1..39
                       mol_type = other DNA
                       organism = synthetic construct
SEQUENCE: 12
ctatggatcc gctagcttac agtccggcca gcggatgct                              39

SEQ ID NO: 13          moltype = DNA  length = 21
FEATURE                Location/Qualifiers
source                 1..21
                       mol_type = other DNA
                       organism = synthetic construct
SEQUENCE: 13
cggatatagt tcctcctttc a                                                 21

SEQ ID NO: 14          moltype = DNA  length = 22
FEATURE                Location/Qualifiers
source                 1..22
                       mol_type = other DNA
                       organism = synthetic construct
SEQUENCE: 14
ggataacaat tcccctctag aa                                                22

SEQ ID NO: 15          moltype = DNA  length = 19
FEATURE                Location/Qualifiers
source                 1..19
                       mol_type = other DNA
                       organism = synthetic construct
SEQUENCE: 15
aagcttgacc tgtgaagtg                                                    19

SEQ ID NO: 16          moltype = DNA  length = 24
FEATURE                Location/Qualifiers
source                 1..24
                       mol_type = other DNA
                       organism = synthetic construct
SEQUENCE: 16
ttcacttttc tctatcactg atag                                              24

SEQ ID NO: 17          moltype = DNA  length = 43
FEATURE                Location/Qualifiers
source                 1..43
                       mol_type = other DNA
                       organism = synthetic construct
SEQUENCE: 17
cctatcagtg atagagaaaa gtgaatgaac acagccgtgg aac                         43

SEQ ID NO: 18          moltype = DNA  length = 44
FEATURE                Location/Qualifiers
source                 1..44
                       mol_type = other DNA
                       organism = synthetic construct
SEQUENCE: 18
atttttcact tcacaggtca agcttcttac gacgcagcct tcag                        44

SEQ ID NO: 19          moltype = DNA  length = 22
FEATURE                Location/Qualifiers
source                 1..22
                       mol_type = other DNA
                       organism = synthetic construct
SEQUENCE: 19
```

-continued

```
catgttcttt cctgcgttat cc                                            22

SEQ ID NO: 20          moltype = DNA  length = 18
FEATURE                Location/Qualifiers
source                 1..18
                       mol_type = other DNA
                       organism = synthetic construct
SEQUENCE: 20
agatccgtga cgcagtag                                                 18

SEQ ID NO: 21          moltype = DNA  length = 19
FEATURE                Location/Qualifiers
source                 1..19
                       mol_type = other DNA
                       organism = synthetic construct
SEQUENCE: 21
tggtgtcggg tcatgtgag                                                19

SEQ ID NO: 22          moltype = DNA  length = 20
FEATURE                Location/Qualifiers
source                 1..20
                       mol_type = other DNA
                       organism = synthetic construct
SEQUENCE: 22
gaaaattgtc gggaagatgc                                               20

SEQ ID NO: 23          moltype = DNA  length = 49
FEATURE                Location/Qualifiers
source                 1..49
                       mol_type = other DNA
                       organism = synthetic construct
SEQUENCE: 23
ctggcctttt gctcacatga cccgacacca ggtactcaaa aagccggtc              49

SEQ ID NO: 24          moltype = DNA  length = 35
FEATURE                Location/Qualifiers
source                 1..35
                       mol_type = other DNA
                       organism = synthetic construct
SEQUENCE: 24
ccacggctgt gttcatcacg aacaactatc tcaag                              35

SEQ ID NO: 25          moltype = DNA  length = 33
FEATURE                Location/Qualifiers
source                 1..33
                       mol_type = other DNA
                       organism = synthetic construct
SEQUENCE: 25
gatagttgtt cgtgatgaac acagccgtgg aac                                33

SEQ ID NO: 26          moltype = DNA  length = 48
FEATURE                Location/Qualifiers
source                 1..48
                       mol_type = other DNA
                       organism = synthetic construct
SEQUENCE: 26
atcagatcac gcatcttccc gacaattttc ttacgacgca gccttcag               48
```